United States Patent [19]
Frederick et al.

[11] Patent Number: 6,112,502
[45] Date of Patent: Sep. 5, 2000

[54] RESTOCKING METHOD FOR MEDICAL ITEM DISPENSING SYSTEM

[75] Inventors: David T. Frederick, North Huntingdon; R. Michael McGrady, Baden; R. Barrie Slaymaker, Jr., Pittsburgh, all of Pa.; Greg Kroah-Hartman, Eugene, Oreg.; Eser Sukan, Pittsburgh, Pa.

[73] Assignee: Diebold, Incorporated, North Canton, Ohio

[21] Appl. No.: 09/021,606

[22] Filed: Feb. 10, 1998

[51] Int. Cl.⁷ .............................. B65B 7/28; B65B 57/00
[52] U.S. Cl. .................. 53/411; 53/77; 53/168; 221/10; 364/479.07
[58] Field of Search .............. 364/479.07, 479.06, 364/479.02, 479.01, 479.11, 479.12, 479.19; 53/168, 473, 475, 411, 77, 508, 507, 501, 500, 493; 221/10, 13

[56] References Cited

U.S. PATENT DOCUMENTS

| | | |
|---|---|---|
| 4,546,901 | 10/1985 | Buttarazzi .................................. 221/10 |
| 5,502,944 | 4/1996 | Kraft et al. ........................... 53/168 X |
| 5,671,592 | 9/1997 | Yuyama et al. ............................ 53/493 |
| 5,720,154 | 2/1998 | Lasher et al. .............................. 53/411 |
| 5,852,911 | 12/1998 | Yuyama et al. ............................ 53/168 |

*Primary Examiner*—James F. Coan
*Attorney, Agent, or Firm*—Ralph E. Jocke; Daniel D. Wasil

[57] ABSTRACT

A system for monitoring and dispensing medical items which are dispensed for administration to patients includes a data terminal (76, 338, 538) which is connected through a network (82, 328, 536) to at least one computer (84, 324, 532) having a processor and a data store. The system also includes a reading device (348, 538) which is operatively connected to the network. A user of the data terminal or the reading device is enabled to select a patient for whom medical items will be used, and responsive to a request to dispense items the requested items are dispensed from dispensing devices (96, 100, 344, 346, 450, 527, 540) connected to the data terminal. Storage locations in dispensing devices may be restocked using removable liners. The removable liners are stocked with medical items in a stocking location (550) and transported in a secure condition to the storage locations. The storage locations are accessed by an authorized restocking user. The previously installed liners removed and the new liners installed. The previously installed liners are thereafter returned to the stocking location for reuse.

45 Claims, 51 Drawing Sheets

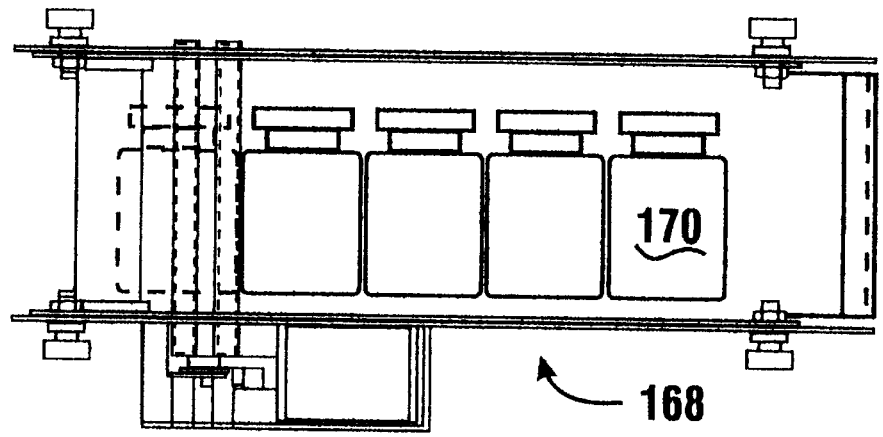
FIG. 14
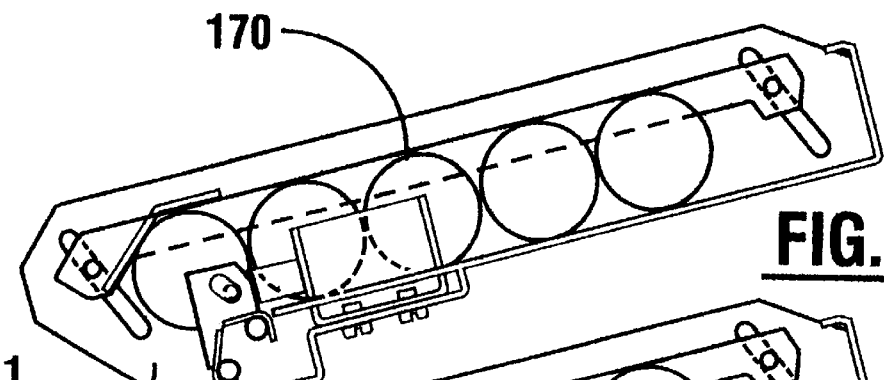
FIG. 15
FIG. 16
FIG. 17

Side View

FIG. 28

Patient Window:

Patient Browser - (Edith, Jennifer (263) Room: ER, Bed: P1) — 222

| Room | Bed | Sex | Patient Name | ID |
|---|---|---|---|---|
| ER | L2 | M | Ellison, Richard | 202 |
| ER | P1 | F | Edith, Jennifer | 263 |
| ER | 5 | M | Orsen, James | 10000 |
| OR | 03 | F | Oliver, Nancy | 103 |
| PACU | 02 | F | Ott, Alice | 101 |
| PostPart | 13 | F | Parker, Arlene | 503 |
| PostPart | 19 | F | Paul, Patricia | 501 |
| 3 North | 30 | F | Martin, Betty | 301 |
| 3 North | 30 | F | McHenry, Ida | 302 |
| 3 North | 31 | M | Mars, William | 304 |

- 228 Find / Add
- 234 Patient Info
- 242 Patient Usage
- 230 Sort by Name
- 240 Help
- 232 Logout
- 254 Dispense by:
- 284 Kit
- 262 Supply
- 294 Retrieve
- 292 Restock
- Inventory Functions
- 224/226 Prev Page / Next Page
- Med Ord

FIG. 29

Patient Info Window:

Patient Information - (Edith, Jennifer (203) Room: ER, Bed: P1) — 236

Patient ID: 203
Med Rec #: 06

Admitted
Date: 8/20/96
Time:

Patient Name: Edith, Jennifer J.
Sex: F
Height: 3.10
Weight: 95 lbs
Date of Birth: 2/25/79

Location
Room: ER
Bed: P1

Physician: Doctor MD., Dr. Emil Richard
Allergies: Penicillin/Cephalosporin

Help — 240

Close — 238

FIG. 30

Patient Usage Browser:

| Date/Time | Status | Generic Name | Qty | Size |
|---|---|---|---|---|
| 20-Aug 07:35 | Taken | Tetanus & Diptheria Toxoids | 1 | 0.5ml |
| 20-Aug 06:02 | Taken | Alprazolam | 1 | 0.25mg |
| 20-Aug 06:02 | Taken | Erythromycin | 1 | 2 tablets |
| 20-Aug 06:01 | Taken | Albuterol | 1 | 17gram |
| 20-Aug 04:45 | Taken | Diphenhydramine | 1 | 50mg |
| 20-Aug 04:45 | Taken | Dexamethasone | 1 | 4mg |

Patient Usage Browser - (Edith, Jennifer (203) Room: ER, Bed: P1) — 244

Trade Name — 252
Discrepancy — 250
Return — 246
Help — 240
Waste — 248
Close — 238
Prev Page / Next Page — 224 / 226

FIG. 31

Med Order Window:

MedOrder Browser - ( Miller, Robert (383) Room: 3North, Bed: 310A )

| Generic Name<br>Route | CR | Order<br>Freq | Qty | Ordered Dose<br>Unit Dose | Start Time<br>End Time | Review<br>Check |
|---|---|---|---|---|---|---|
| Warfarin | | 222920 | | 7.5 mg | 08/18/96 00:00 | |
| Oral | | q6pm | 1 | 7.5 mg | | C |
| Prochlorperazine | | 222900 | | 10 mg | 08/15/96 00:00 | |
| Intramuscular | | q8hprn | 1 | 10 mg | | C |
| Ibuprofen | | 222934 | | 800 mg | 08/20/96 00:00 | |
| Oral | | q4prn | 1 | 800 mg | | C |
| Lisinopril | | 222899 | | 15 mg | 08/15/96 00:00 | |
| Oral | | qam | 2 | 10 mg | | R |
| | | | | | | C |
| Allopurinol | | 222933 | | 300 mg | 08/20/96 00:00 | |
| Oral | | qam | 1 | 300 mg | | C |

[Prev Page] [Next Page] [Trade Name] [Info] [Dispense] [Help] [Close]

FIG. 32

Supply Browser:

Supply Browser - (Edith, Jennifer (263) Room: ER, Bed: P1)

| Generic Name | Size | Strength | Qty | CR |
|---|---|---|---|---|
| Morphine | 10mg | 10mg/1ml | 1 | * |
| Naloxone | 0.4mg | 0.4mg/1ml | | |
| Nifedipine | 10mg | 10 mg | | |
| Nifedipine | 30mg | 30 mg | | |
| Nitroglycerine | 50mg | 50mg/500ml | | |
| Omeprazole | 20mg | 20mg | | |
| Oxycodone/Acetaminophen | 5/325mg/ | 5/325mg | | |
| Prednisone | 5mg | 5 mg | | |
| Prochlorperazine | 10mg | 10mg/2ml | | |
| promethazine | 25mg | 25mg/1ml | | |

Select Quantity
1
2
3
4
5
6
7
8
9
10

Trade Name
Info
Dispense
Help

Phys/Route/Site

Prev Page
Next Page
Close

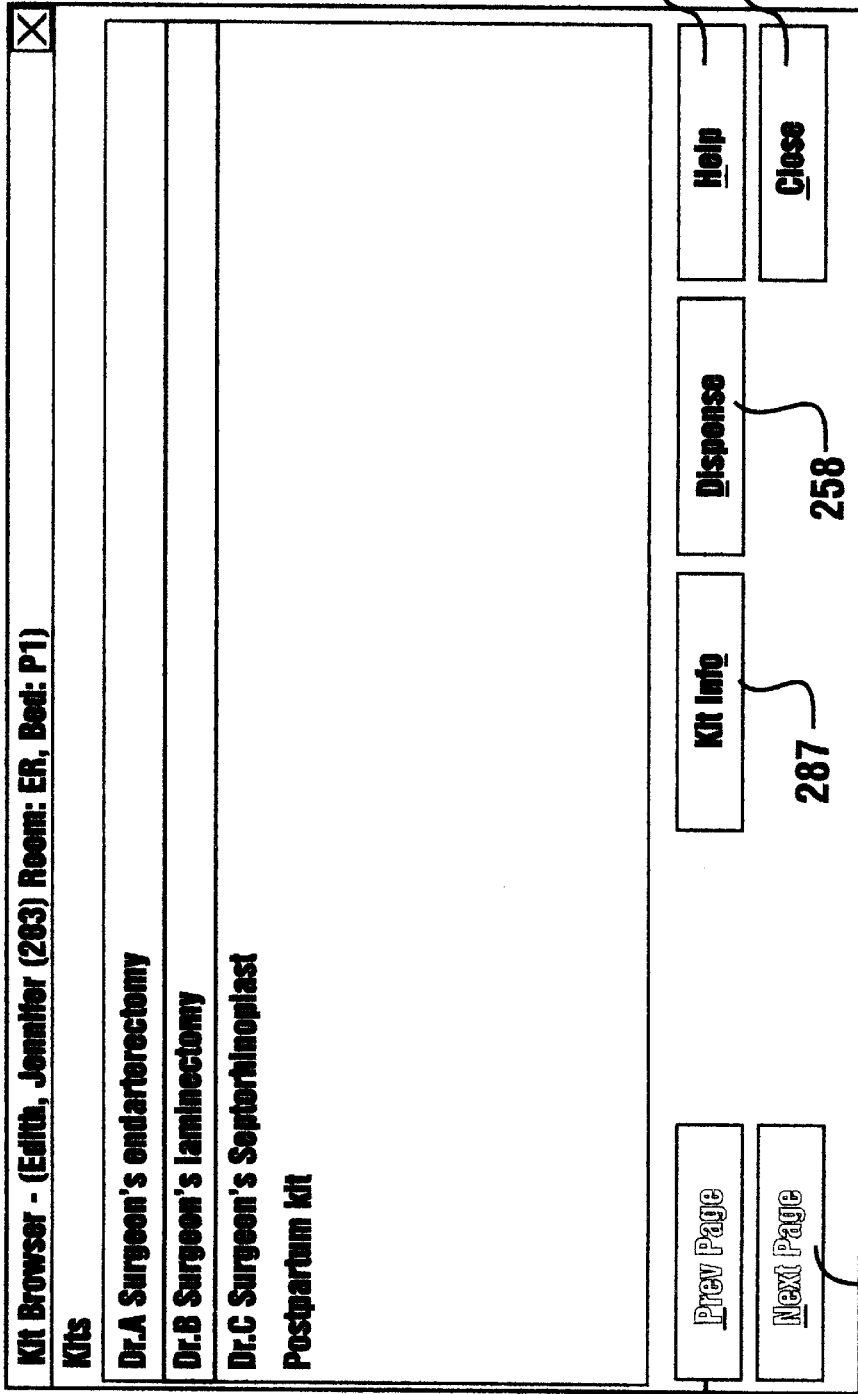

FIG. 34

Kit Info Window:

Kit Information - (Edith, Jennifer (203) Room: ER, Bed: P1)

Kit: Dr.B Surgeon's laminectomy

| Generic Name | Size | Strength | Kit Qty | DT Qty | CR |
|---|---|---|---|---|---|
| Bacitracin | 50,00 | 50,000 un | 1 | 13 | |
| Gelfoam sponge | 1 spon | large | 1 | 9 | |
| Lidocaine w/ Epinephrine | 30ml | 1% 30ml | 1 | 0 | |
| Methylprednisolone Sodium Succinate | 125m | 125mg/2 | 1 | 0 | |
| Thrombin, topical | 1000u | 1000 unit | 1 | 9 | |

[Prev Page] [Next Page]    [Trade Name]    [Help] [Close]

Supply Browser - (Shakespeare, William (0120902) Room: KDCUBE, Bed: 2)

| Generic Name | Size | Strength | Qty | CR | Select Quantity |
|---|---|---|---|---|---|
| BRETYLIUM | 1AMP | 500MG A | | | 1 |
| | | | | | 2 |
| | | | | | 3 |
| | | | | | 4 |
| | | | | | 5 |
| | | | | | 6 |
| | | | | | 7 |
| | | | | | 8 |
| | | | | | 9 |
| | | | | | 10 |

Trade Name — 252

Info  Dispense  Help

Prev Page  Phys/Route/Site  Close

Next Page

270

Login Window showing Non-Itemized button

| Non-Itemized Supply Inventory Window - [ERDT1 / in Emergency] | | | | |
|---|---|---|---|---|
| Position Description | Generic Name | Size | Strength | Status |
| ER ADC Cabinet1 Shelf 1-8 | ACETAMINOPHEN | 12SUP | 120MG | OStck |
| ER ADC Cabinet1 Shelf 1-9 | ACETIC ACID/HYDR | 1BTL | OTSOL | OStck |
| ER ADC Cabinet1 Shelf 1-10 | ACETYLCYSTEINE/2 | 1VIAL | 20% 30 | BMin |
| ER ADC Cabinet1 Shelf 1-1 | ASCORBIC ACID | 2ML | 500MG | Rstkd |
| ER ADC Cabinet1 Shelf 1-2 | ASPIRIN | 12SUP | 600MG | BMin |
| ER ADC Cabinet1 Shelf 1-3 | ASPIRIN CHILDREN | 36TAB | 81MG T | Rstkd |
| ER ADC Cabinet1 Shelf 1-4 | ASPIRIN EC | 100TAB | 325MG | OStck |
| ER ADC Cabinet1 Shelf 1-5 | CLINITEST SET | 1KIT | KIT | OStck |
| ER ADC Cabinet1 Shelf 1-6 | CLINITEST-REFILL | 1BTL | 36TAB | Rstkd |
| ER ADC Cabinet1 Shelf 1-7 | FAMOTIDINE | 100TAB | 40MG T | Rstkd |

Trade Name   Below Min.   Restocked   Help

Supply Position   Out of Stock   Max All   Close

Prev Page

Next Page

Non-Itemized Supply Inventory Window

FIG. 39

ASPIRIN
12 SUPP 600MG SUPP

HF4351521 1B

↗ 360

ER ADC Cabinet1
Shelf 1-2

Position Only

ASPIRIN
12 SUPP 600MG SUPP

HF430152116

↗ 368

ER ADC Cabinet1
Shelf 1-2

Out of Stock

ASPIRIN

12 SUPP 600MG SUPP

HF432152118

↗ 372

ER ADC Cabinet1
Shelf 1-2

Restocked

ASPIRIN

12 SUPP 600MG SUPP

HF431152117

↗ 374

ER ADC Cabinet1
Shelf 1-2

Below Min

ASPIRIN EC
100 TAB 325MG EC TAB
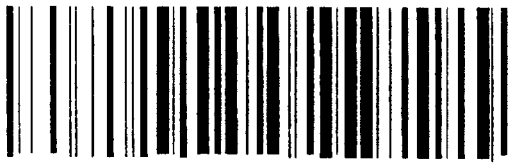
HF43215213A
ER ADC Cabinet1
Shelf 1-4
Restocked
CLINITEST SET
1 KIT KIT
HF43215214B
ER ADC Cabinet1
Shelf 1-5
Restocked
CLINITEST-REFILL
1 BTL 36TAB BTL
HF43215215C
ER ADC Cabinet1
Shelf 1-6
Restocked
↙ 398
FIG. 46

RESTOCKING METHOD FOR MEDICAL ITEM DISPENSING SYSTEM

TECHNICAL FIELD

This invention relates to medical inventory monitoring and dispensing devices and systems. Particularly this invention relates to apparatus and methods for dispensing and tracking an inventory of medical items used to treat patients in a hospital, clinic or other healthcare setting, and a method for restocking such a system using removable liners which may be replenished with stocks of medical items and placed in storage locations from which medical items are provided.

BACKGROUND ART

The treatment of patients in hospitals and clinics usually involves the receipt by the patient of medical items. These items may include consumable items such as medications. Medical treatment may also involve other disposable items such as dressings and bandages or other medical equipment. Items implanted into the patient or used in conjunction with surgical procedures may also be used and consumed during the course of a patient's medical treatment. Examples of such items include splints, catheters or guide wires which are normally used during cardiac catheterization or angioplasty. To serve the needs of its patients, a clinic or hospital must always maintain sufficient stocks of these items on hand. Further, as medical items are often expensive, the charges associated with their use must be accurately billed to the patient.

Currently most systems for tracking inventory and use of medical equipment items in a hospital or clinic environment are largely manual systems. The persons responsible for maintaining an inventory of particular items must monitor the use of the items in each storage location within the hospital and order additional supplies when it is noted that the available stocks are running low. Often personnel are only familiar with the stocks available in a particular storage location and as a result, additional stocks may be ordered even though ample supplies are available elsewhere in the same facility.

Certain drugs used in the course of medical treatment are regulated narcotics. Supplies of such drugs must be kept in secure cabinets. Items may be dispensed from the secure cabinets only by two (2) authorized users accessing the material and certifying the manner in which it is used. The use of such narcotics also may require considerable paperwork which takes away valuable time that could be used for treating patients.

Some types of medical items must be maintained in refrigerated storage. Often such refrigerated storage must be maintained until almost the time of use. Keeping track of items that require refrigerated storage and assuring that adequate inventories of such items are always available presents additional challenges compared to medical items which do not require such special conditions. Due to the diverse types of medical items that may require storage in refrigerated conditions it is also difficult to selectively restrict access to such items.

The recording of medical items so that the patient may be billed for their use in the course of treatment is also largely a manual operation. The fact of use by the patient must be recorded in the patient's chart. In some cases items have peel-off labels that include a bar code that can be scanned and used for billing purposes. However, this still requires that the nurse or medical technician transfer the correct coding to the proper location for later billing.

Complications in billing become even greater when items are removed from inventory to accomplish a planned surgical procedure and then the items are not used. A patient may be charged for use of a particular item which is removed from inventory in anticipation of surgery. If during the surgery the item is not needed, a corresponding credit must be issued when the item is returned to stock. All of these activities take time away from persons who could otherwise devote their time to the treatment of patients. Such tracking and billing practices are also prone to inaccuracies which may cause the hospital or clinic to lose money or which may result in overbilling of the patient.

Thus there exists a need for an apparatus and system for monitoring and dispensing medical items in hospital or clinic environments that can more accurately monitor inventories, dispense medical items and correlate the use of medical items with the patient whose treatment has included their use. There further exists a need for a method and system for the restocking of medical items in such a system that provides more accurate, convenient and secure movement of medical items from a pharmacy or other location where medical items are prepared, to the locations where the medical items are taken for use by patients.

DISCLOSURE OF INVENTION

It is an object of the present invention to provide a system for monitoring an inventory of medical use items to provide an indication of what items have been used.

It is a further object of the present invention to provide a system for monitoring the use of medical use items so that supplies may be replenished before depletion.

It is a further object of the present invention to provide a system for monitoring an inventory of medical use items that monitors a plurality of items in real time.

It is a further object of the present invention to provide a system for monitoring an inventory of medical use items that minimizes the processing of paper forms.

It is a further object of the present invention to provide a system for monitoring and dispensing medical use items that indicates the patient whose treatment has involved the medical use items.

It is a further object of the present invention to provide a system for monitoring and dispensing medical use items that can be used to indicate the technician or physician who has used such medical use items.

It is a further object of the present invention to provide a system for monitoring and dispensing medical use items that provides for crediting of a patient's account upon return of an unused item to inventory.

It is a further object of the present invention to provide a system for monitoring and dispensing medical use items that is used to store and dispense restricted items in a secure manner.

It is a further object of the present invention to provide a system for monitoring and dispensing medical use items that are stored in a refrigerator or other compartment having controlled environmental conditions.

It is a further object of the present invention to provide a system for monitoring and dispensing medical use items that can guide a user to select the items that will be used in a particular medical procedure.

It is a further object of the present invention to provide a system for monitoring and dispensing medical use items that may be used to track and dispense a wide variety of various items and to record their use in a clinical or hospital environment.

It is a further object of the present invention to provide a system for monitoring and dispensing medical use items that enables a user in the course of a dispensing sequence to selectively review and dispense medications by either the generic name or the brand name.

It is a further object of the present invention to provide a system for monitoring and dispensing medications that enables a user to dispense together predetermined medical items that are used as a kit in the conduct of a medical procedure.

It is a further object of the present invention to provide a dispensing mechanism that reliably dispenses medicines to a user in response to the user's selection of items.

It is a further object of the present invention to provide a method for monitoring and dispensing medical use items.

It is a further object of the present invention to provide a method for monitoring an inventory of medical use items that are not tracked to a patient.

It is a further object of the present invention to provide a method for dispensing medical use items that can be carried out more rapidly and efficiently.

It is a further object of the present invention to provide a method for more efficiently restocking storage locations with medical use items.

It is a further object of the present invention to provide a method for restocking storage locations with medical use items that provides enhanced security.

It is a further object of the present invention to provide a method for restocking storage locations with medical use items that reduces errors in the restocking of storage locations.

It is a further object of the present invention to provide a method for restocking storage locations with medical use items that employs removable liners in a storage location which liners can be transported between a stocking location and a storage location from which medical use items are taken for patients and which subsequently can be removed from storage locations and returned to the stocking location.

It is a further object of the present invention to provide a method for restocking storage locations with medical use items that includes a liner configuration that can be handled more efficiently during transport.

It is a further object of the present invention to provide a method for restocking storage locations with medical use items that provides a tamper indicating container for transporting the medical use items.

It is a further object of the present invention to provide a method for monitoring and dispensing medical use items stored in a refrigerator or other environmentally controlled storage area.

It is a further object of the present invention to provide a system for monitoring and dispensing medical use items that enables monitoring and dispensing of medications when portions of the system are not operational.

It is a further object of the present invention to provide a method for operating a system for monitoring and dispensing medical use items that selectively updates stored information to maximize accuracy.

Further objects of the present invention will be made apparent in the following Best Modes for Carrying Out Invention and the appended claims.

The foregoing objects are accomplished in a preferred embodiment of the invention by a system for monitoring and dispensing medical items in a clinical or hospital environment. This system includes a plurality of item storage locations. A particular type of medical item may be stored in each location. For example, one type of medical item may include a particular type of catheter. Another may be a particular type of medication packaged in a particular dosage. Each location in the system includes at least one unit of the particular type of medical item.

A sensor is positioned adjacent to certain storage locations. The sensor is particularly adapted to sense the addition or subtraction of a unit of the particular type of medical item that is stored in the location. As a result, each time a unit of the particular item is added or removed from storage in the location, the sensor senses this and generates a signal.

A counter is connected to each such sensor and records the number of units added or removed from each location. The counter holds a count of the change in the number of units at the location since the last time the counter was read.

The counters associated with each location are connected to at least one processor and at least one memory or data store. The data store includes a total of the number of items that are located in storage at the location. Periodically, the processor polls each of the counters and reads the change in the number of units stored therein. Thereafter the processor is operative to update the total number stored in the memory to reflect the number of items currently stored at the location.

Embodiments of the invention include a data terminal which includes a user interface and which terminal is connected to the processing system and the counters. The data store includes records concerning patients, procedures, authorized users of the system and each of the products stored in each of the locations, including pricing information. The data store further preferably includes data representative of medical items prescribed for patients as well as the medical items that have been taken by users of the system for patients. The data store further preferably includes data representative of the function the user usually performs and the activities the user has performed. The data store further preferably includes data representative of whether each particular medical type item is tracked to patients, whether each type of medical item is billed to patients, and the quantity or level of medical items stored in each storage location.

The data store preferably includes data in correlated relation concerning the brand names and generic names for medications and other medical items stored in the locations of the system. The data store further preferably includes information on "kits" which are groups of medical items that are used together. Such kits may be groups of items which are used together repeatedly, such as in doing a diagnostic test. Alternatively, a kit may comprise items that are to be used on a one-time basis, such as for a particular patient's operative procedure. The data on items in each kit are stored in correlated relation with the kit designation in the database.

A system user, such as a technician or nurse, may use the interface of the data terminal to identify the particular patient who is to receive the medical items taken by the user. Upon removal or dispense of the items from the storage locations, the use of such items is recorded in correlated relation with the patient record in the data store so that the patient's chart may be automatically updated and the item charged. In addition, a user using the data terminal may review information in the data store concerning procedures and physicians to determine what medical items are required by a physician to conduct a procedure and may remove such items for delivery to an operating room. This information may include kits which relate to particular procedures. The user is enabled to take or cause medical items to be dispensed through inputs to the data terminal.

The user may also use the interface of the data terminal to check stocks of medications which are available as well as medications which have been prescribed for a patient. The user is enabled to use the interface to check the brand name for medical items designated by generic name, and vice versa. This is done by the user interface interfacing with the drug information stored in the data store. This enables a user to check for the availability of medications by either brand or generic name. This also enables a user to check the appropriate character of an item prescribed by checking its other name. This also enables a user to determine the availability and use a brand name or generic name equivalent to the medical item prescribed, when the brand or generic type prescribed is not available.

In embodiments of the invention, controlled substances such as narcotics, may be dispensed using the system from a dispenser mechanism or an electronic lock drawer. In some embodiments, the user is required to identify himself at the display terminal. This information is processed and compared to authorized user records in the data store to verify that the user is an authorized user. In some embodiments the identifying information on the user may be placed on an encoded object or article such as a card, and the user may be assigned a personal identification number (PIN) that is memorized by the user. The data terminal preferably includes a reader for reading the coded object and for receiving the user's PIN number which has a predetermined relationship to the data on the encoded object. The proper input of the PIN with the corresponding user's coded object verifies that a proper user is requesting to gain access to the items. For some strictly controlled substances two (2) authorized users may be required to input their coded objects and PIN numbers in order to gain access to the controlled items. In alternative embodiments biometric type identification devices may be used, such as those that identify a user by fingerprints, hand scans, retina scans, iris scans, voice prints or other body features.

In embodiments of the invention medical items may be stored in an interior area of a refrigerator. The refrigerator may be of a conventional or unconventional type having a door for accessing the interior area. The refrigerator may preferably be fitted with a lock module which enables selectively enabling access to the interior area in response to signals from the display terminal. A lock module enables the refrigerator to operate in a manner similar to an electronic lock drawer. Varying levels of security for refrigerated items may be provided by using several refrigerators each of which includes its own lock module. Alternatively subcompartments within the refrigerator, each with individual lock modules may be provided.

In the preferred embodiment the lock modules are readily attached to exterior surfaces of the refrigerator.

As with the previously described embodiments, once the authorized user has provided the necessary identification, the processor operates to cause the desired substance to be dispensed or made accessible to the user. The user is also required to input the corresponding patient data so that the patient's chart and billing may be updated.

In an alternative embodiment a user is enabled to access the system using a scanner or similar reading device. Instead of inputting data into the display terminal to identify himself, the user scans a machine readable code on a badge, identification card or other article or body feature corresponding to the user. For the dispensing of narcotics, which requires two authorized users, two users may scan their respective identification item using the reading device. The reading device preferably includes an output device, such as a small screen, which provides messages to prompt users on the steps to be taken in a manner similar to that done when the user operates a display terminal. The reading device also preferably has an input device thereon, such as an alphanumeric keypad and/or function keys, which provides additional ways for a user to provide inputs to the reading device in addition to scanning machine readable indicia.

In the alternative embodiment, storage locations such as shelves, drawers and/or refrigerator units preferably have machine readable indicia adjacent thereto. The machine readable indicia corresponds to the location designator for the storage location, and the data stored in the data store includes data representative of the type of medical item stored in each location. The storage locations also preferably include a further machine readable indicia thereon which is indicative that the quantity of medical items in the storage location is depleted. The further indicia is preferably positioned in or adjacent to the storage location so as to be accessible by the reading device when the last of the medical items in the storage location has been removed.

The alternative embodiment including the reading device is useful for indicating various types of quantity conditions which occur at storage locations. The preferred form of the reading device includes a processor and a local data store therein which enables it to perform operations in accordance with its programming, which is referred to herein as its configuration. The reading device also produces transaction messages which are sent to other components of the system.

Certain types of medical items are not tracked or billed to patients. Such items may include aspirin, cotton swabs or bandages. Items of this type may be stored in an open storage location such as open shelving and are available for any user to take. The storage locations for items that are not tracked to patients are preferably marked with machine readable indicia of a type that is visibly distinguishable to a user from indicia for storage locations holding items that must be tracked and billed to patients. The storage locations for items that are not tracked to patients are preferably marked to show a desired level or quantity (a "par value") of medical items that should be kept in the storage location. If the level of medical items in the location drops and a user observes that it is below par value, the user may scan the indicia with the reading device. The reading device is preferably configured to treat the scanning of indicia corresponding to a storage location, absent previously inputting data related to a user or a patient, as indicative of a quantity condition at the location which corresponds to the storage location being below par value.

Alternatively, when all the medical items have been removed from the storage location the user may operate the reading device to read the further indicia adjacent the storage location representative of the condition that all the medical items in the location have been depleted. Such a condition is an alternative quantity condition which causes different signals to be generated by the system from those corresponding the first quantity condition. Transaction messages comprised of signals are produced by the reading device corresponding to the different quantity conditions. These transaction messages are sent to other components of the system, and in the case of messages which indicate that a storage location is below par value or depleted, are responded to by restocking the storage location with an additional quantity of medical items.

In the alternative embodiment the reading device can be used for tracking medical items taken for use by patients. A user may log into the system using the display terminal or by using the reading device to read their identification card, badge, other identifying article or feature. Most users of the system who are nurses or medical technicians perform activities which are primarily the dispense of medications for use by patients. The data store preferably includes data representative of the dispense function as the function associated with such users. The user will be considered by the system as performing this function unless the user provides an input to the reading device that indicates that he or she is going to perform a different function.

In one form of the system, once the user has logged onto the system he or she may select a patient at the display terminal and may scan or read the indicia at the locations from which medications are taken for the patient. This will cause the information concerning the taking of the medications for the patient to be stored in the data store. If access to the desired medication or medical item is controlled by an access control device, such as an electrical lock on a cabinet, a lock module on a refrigerator, or an electronic lock drawer, the reader can be used to gain access to the medical items controlled by the access control device. The storage location or locations to which access is controlled by the access control device preferably includes machine readable indicia on its exterior. In operation of the described form of the system, when an authorized user is logged on the system, scanning the indicia associated with the access control device enables the user to access the medical items, such as by unlocking a lock or opening a drawer. The indicia corresponding to the locations from which the medical items are taken may then be read with the reading device. A transaction message is generated which is used to update the information in the data store. The transaction message preferably updates the data concerning medications taken for the patient, as well as the inventory status for medical items at the various storage locations from which the items have been removed. The user can then select another patient at the display terminal and repeat the process.

The system of the alternative embodiment of the invention also preferably has available in the data store not only data representative of the patients who may receive medical items but also the medical items that have been prescribed for use by such patients. This enables printing reports with a report generating device. Such reports may include both human readable as well as machine readable indicia representative of patients and their prescribed medications. In an alternative form of the invention a user may use the reading device to select a patient by reading the indicia corresponding to that patient from a report rather than selecting the patient using the display terminal. The user may then scan the indicia from the storage locations to indicate the medical items taken for the patient in the manner previously described. Alternatively, the indicia corresponding to a medical item may be scanned from the report if access to such medical item is controlled by an access control device. For example, if the item is stored in the interior of an electronic lock drawer, refrigerator or a dispenser, scanning the indicia on the report causes the system to operate to make the item accessible to the user by opening the access control device to the storage location or by causing the item to be dispensed from the dispenser.

A user may select several patients and their associated medical items in a sequence using the indicia on a report. The reading device preferably holds the information until the user indicates that they are done by "logging off" the system. This avoids slowing the system operation by trying to send messages to other components of the system while the user is operating the reading device. After the user has logged off, the transaction messages may be sent as a batch to the other components of the system. A user may log off the system by inputting a command through the input device such as the keypad on the reading device. Alternatively, a user may log off by scanning machine readable indicia which indicates that the user is logging off the system, or by a new user scanning indicia associated with the new user. Alternatively, or in addition, the reading device may be provided with a storage location referred to herein as a cradle, and a log off signal may be generated whenever the reading device is returned to its cradle. Of course in alternative forms of the system the reading device may send its transaction messages as events are occurring rather than waiting until after a user logs off.

The reading device may in various embodiments be connected to the remainder of the system by a data line or may communicate its messages through forms of wireless communication. Dispensers, drawers and other types of storage locations which incorporate access control devices in the described embodiment are connected to the system by data lines. However in alternative forms of the system such devices may be connected to the remainder of the system through wireless communication methods. Such dispensing devices may in further alternative embodiments include a processor and a memory which enables them to operate in an off line mode of operation. Such devices may then communicate with the rest of the system to periodically deliver information on dispensing or restocking activities. This communication may be accomplished by data line, wireless communication methods or through an intermediate device which can receive data from the dispensers, store the received data, and deliver it to the rest of the system. The intermediate device may have various portable or stationary forms, and in certain embodiments may be the reading device or a device functionally similar thereto.

The alternative embodiments which include the reading device may also be used to facilitate restocking of the system. Labels may be provided on storage locations to indicate a restocked condition. Alternatively, or in addition, reports can be generated based on the data in the data store which shows the storage locations which require restocking with additional items. Such reports may include human as well as machine readable indicia showing the item to be restocked, the storage location, the number of units to be added, as well as an indication that a restock function is to be performed. Users who primarily perform restocking functions may be provided identification cards, badges or other associated articles or features with machine readable indicia that identifies them, and the data store includes data which indicates that the activity normally carried out by such users will be a restock function unless otherwise specifically indicated.

Users who restock storage locations may identify themselves to the system using the display terminal, or alternatively by reading the indicia from their identification card, badge, article or feature with the reading device. Such users may indicate that storage locations have been restocked by scanning the machine readable indicia for a location from a report or from the storage locations, or both, in accordance with the configuration of the reading device. Numerical data concerning the number of items in inventory can be counted and input through the keypad on the reading device. The reading device is also preferably configured to provide prompt messages on a screen or other output device, to guide a user through the restocking process.

In embodiments of the invention the dispensing and restocking processes may also be accomplished through the interface of the display terminal, as well as by using the reading device. This enables users of the system to accomplish their functions using either the display terminal or the reading device, and in the event one malfunctions, required activities can still be carried out. This ability to carry out functions through the reading device, the display terminal, or both working cooperatively increases flexibility and reliability of system operation.

In alternative forms of the system dispenser devices such as electronic lock drawers, refrigerators, cabinets and other types of dispensers may accept removable liners in the storage locations therein. The liners hold the type of medical item that is dispensed from the storage location and are configured to enable removal of medical items from the liner either manually or mechanically in accordance with the normal operation of the dispenser device. Open storage locations for medical items may also include removable liners in the open storage locations.

The use of the removable liners facilitates restocking the storage locations. Each liner is preferably stocked with a first type of medical item in a stocking location such as in a pharmacy. Once the liner has been filled a removable lid is installed to restrict access to the medical items held in the liner. Preferably a locking mechanism such as a tamper indicating lock is used to hold the lid in engagement with the liner.

In one preferred embodiment machine readable indicia is applied to each liner. The machine readable indicia includes information representative of the storage location in which the liner is to be installed. This indicia may include data representative of a particular storage locaiton. Alternatively the indicia may include only the type of medical item housed in the liner. The location in which the liner will be installed may then later be determined based on information stored in the data store. The indicia applied in associated relation with the liner may be in the form of a bar code label applied to the liner or the lid. Alternatively the indicia may be applied in connection with a tamper indicating seal which is part of the locking mechanism which holds the lid and the liner together.

In one preferred form of the invention the indicia which is applied in associated relation with the liners comprises a bar code. The bar code is preferably produced using a printer in the restocking location. The bar code indicia is preferably in the form of labels that may be transferred to the liners or tamper indicating tags associated therewith. A restock report may also be produced at the stocking location to indicate where the liners or the type medical item held therein are to be installed. This information is produced based on information stored in the data store which indicates where restocking is required.

In one preferred form of the invention the liners and lids are configured to be stacked in nested relation. One preferred configuration provides for releasible engagement which restricts shifting of the liners as they are transported from the restocking location to the storage locations in which the liners are installed.

Once the filled liners reach the area adjacent to the dispenser device or other location in which they are to be installed, the restocking user accesses an interior area of the dispenser device, cabinet, refrigerator or other storage location. This is done by the restocking user in the established manner for the system. This may include the restocking user logging onto an appropriate device such as a data terminal or scanning device, which is done using indicia identifying the user.

In one preferred method of operation of the system a restocking user may access storage locations by reading the machine readable indicia associated with the liner. Upon reading the indicia, information stored in the data store is used to determine the location corresponding to the indicia. For example if the indicia indicates the type of medical item in the liner, the stored data is used to determine the storage location in which that particular type medical item is stored in that particular dispensing area. The information in the data store may then be used by the computer to provide the restocking user with access to that particular location. This may be done such as by unlocking the drawer in an electronic drawer module where that particular type of medical item is stored. In alternative embodiments a user may gain access by scanning information off of the restock report which indicates where the liners are to be installed. In further alternative embodiments other approaches may be used.

Once a restocker has gained access to the storage location where the liner is to be installed, the user generally must remove a previously installed liner from the storage location. This previously installed liner may contain medical items. The user unlocks the locking device for the liner that is to be installed and removes the lid therefrom. This may be done either before or after the liner is installed in the storage location depending on the particular situation.

In some embodiments the restocking user may transfer medical items from the previously installed liner to the new liner. When this is done information concerning the number and type of units transferred is input to the system through an input device such as the display terminal or a scanner. Alternatively the previously installed liner may be secured with the lid from the liner that has now been installed in the storage location. If the previously installed liner includes medical items that are to be returned to the stocking location, the lid is preferably secured to the liner with a locking device such as a tamper indicating seal. The previously installed liners are then preferably returned to the stocking location. If medical items were returned with the previously installed liners, the type and number thereof is checked against the data stored in the data store to verify that no improper activity has occurred.

In one preferred embodiment of the invention proper installation of the liners in the storage locations is verified electronically. This is accomplished by labeling the storage locations with identifying indicia. This indicia may be representative of the location or alternatively may include the type of medical item that is stored therein. To verify that the liners are properly installed once access to the storage location has been obtained, a restocking user reads the location identifying indicia from the location with a scanner. A computer then determines based on the information stored in the data store whether the location in which the restocking user is installing the liner is a proper location for the liner to be installed. If a possible error is detected, an appropriate signal is given so that the user is alerted that they may be installing the liner improperly. This feature may be particularly valuable when liners are being installed in cabinets or refrigerator units where access to several storage locations is controlled by a single locking mechanism. Likewise this feature is useful when liners are being installed in open storage locations.

In embodiments of the invention, the system may interface with other computer systems such as the admission-discharge-transfer (ADT) computer system that the hospital uses to track patients. This is a computer system which is used in a hospital or clinic to track patient location and activity. In addition, the system of the present invention may also be connected to the hospital information system (HIS) which is the record storage facility of the hospital which maintains computerized records concerning patients. The system may be interfaced to the pharmacy system which keeps records of medications prescribed for each patient. As a result, patient activity, record keeping, and billing may be automated through the system of the present invention, along with inventory monitoring. The system of the present invention may also be used to produce a wide variety of reports from the data store related to patients, authorized users, physicians and various types of items used in inventory. Such a system may also be integrated with an automatic ordering system so as to transfer supplies from one location to another where they are needed and/or to automatically place orders for additional supplies with vendors when supply levels reach a limit.

BRIEF DESCRIPTION OF DRAWINGS

FIG. 14 is a top plan view of a dispenser mechanism for vials containing medications.

FIG. 15 is a cut-away side view of the dispenser shown in FIG. 14 with the gate members thereof in a first position.

FIG. 16 is a view similar to FIG. 15 with the gate members of the dispenser in a second position.

FIG. 17 is a side view similar to FIG. 16 with the gate members in a third position wherein a vial is dispensed from the mechanism.

FIGS. 28 through 39 are windows displayed on the touch screen of the data terminal in an embodiment of the invention, with FIG. 28 being a patient browser window.

FIG. 29 is a patient information window.

FIG. 30 is a patient usage browser window.

FIG. 31 is a med order browser window.

FIG. 32 is a supply browser window.

FIG. 33 is a kit browser window.

FIG. 34 is a kit information window.

FIG. 35 is a supply browser window selected to display trade name information for the displayed medical items.

FIG. 36 is a supply browser window like FIG. 35 selected to display generic name information for the displayed medical items.

FIG. 37 is a physician/route/site browser window selected to display route information for a medication.

FIG. 38 is a window through which a user may log into a display terminal.

FIG. 39 is a non-itemized supply inventory window which is used to review and input information concerning non-itemized medical items which are not tracked to patients.

FIG. 46 is a view of machine readable indicia which may be included in a restock report.

BEST MODES FOR CARRYING OUT INVENTION

Figure 1:
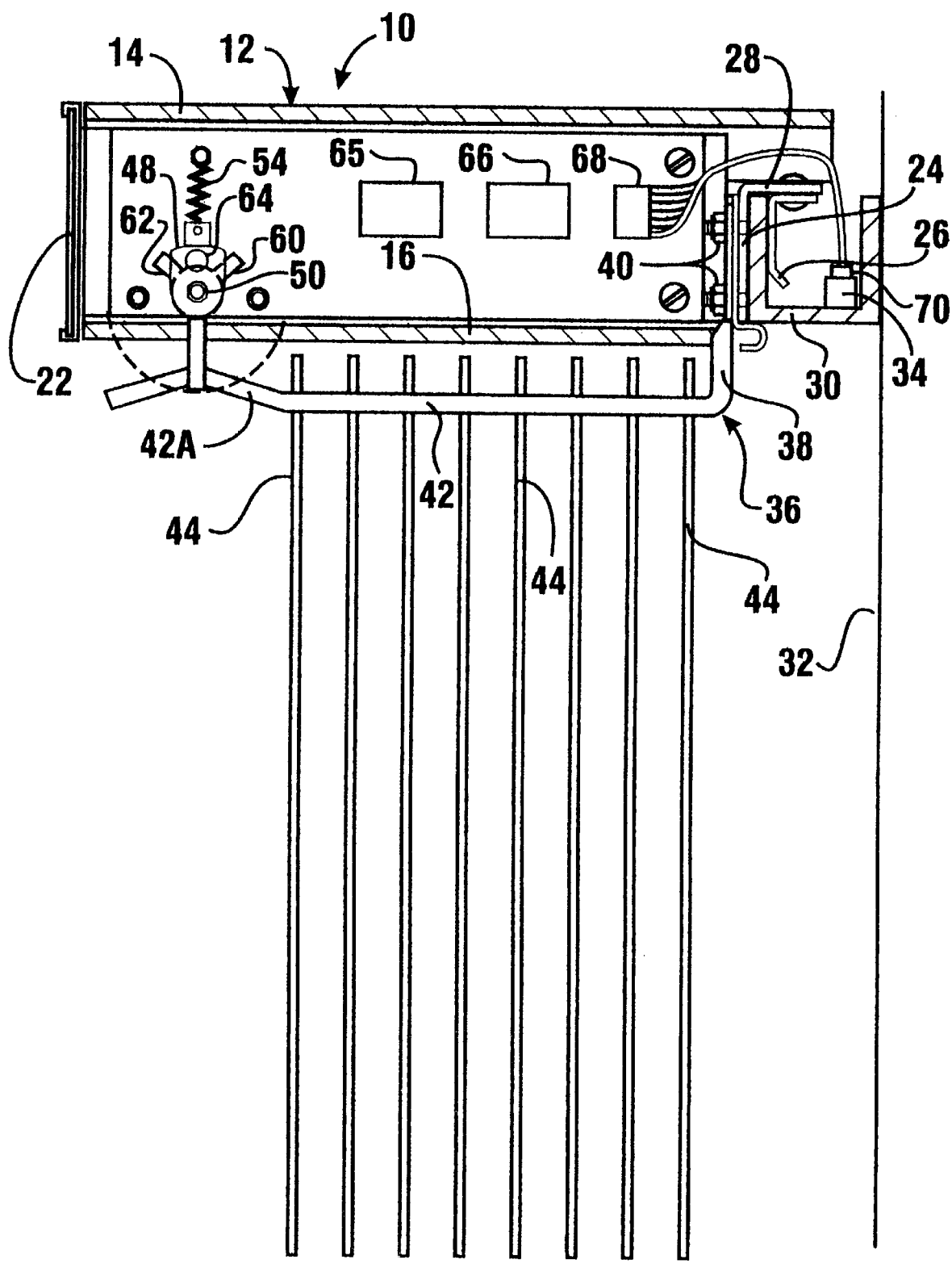
FIG. 1 is a side cross sectional view of an inventory monitoring apparatus called a hook register used in the system of the present invention.
Figure 2:
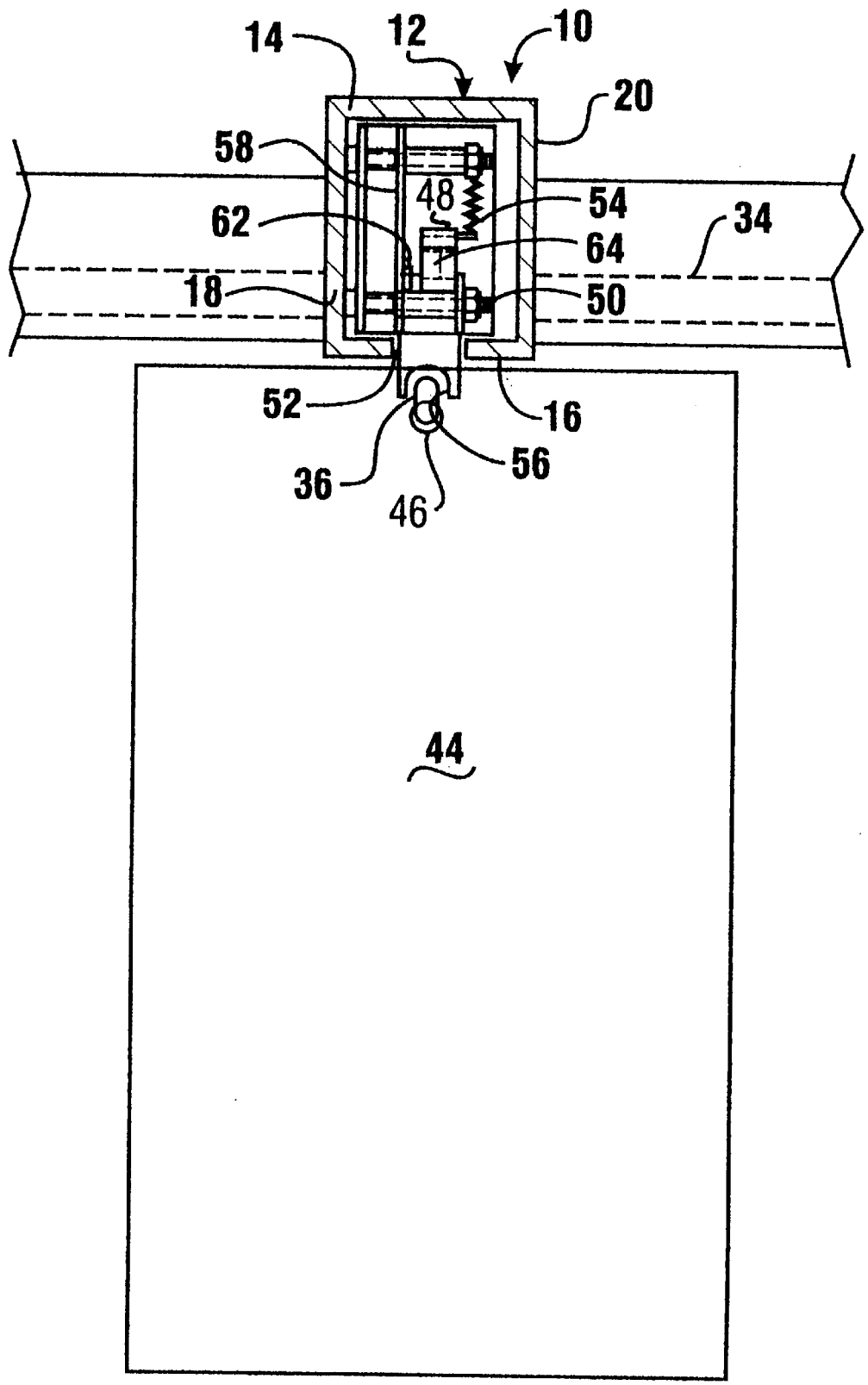
FIG. 2 is a front cross sectional view of the hook register shown in FIG. 1.

Referring now to the drawings and particularly to FIGS. 1 and 2, there is shown therein a first embodiment of an inventory monitoring apparatus for use in the present invention referred to as a hook register and generally designated by reference numeral 10. Apparatus 10 includes an elongated housing 12 including an upper wall 14, a lower wall 16, side walls 18 and 20, a front wall 22 and a rear wall 24. Housing 12 may be formed of any suitable durable material such as plastic or metal. A clip assembly 26 or similar attachment mechanism is desirably carried by a flange 28 of rear wall 24 whereby the housing may be detachably fastened to a rail or similar support structure 30 affixed to a wall 32 or like surface. As will be discussed in greater detail hereafter, rail 30 may also carry a communications bus 34 or other suitable means for electrically connecting the apparatus 10 to a similar apparatus and to a remote computer and data terminal.

An object support means is designated by reference numeral 36. As illustrated, the object support may assume the form of an elongated rigid or angled rod which may be suitably formed of metal or plastic. A shorter leg 38 of the object support means is affixed such as by threaded fasteners 40 to the rear wall 24 of housing 12. A longer leg 42 of the object support means extends generally longitudinally of the housing 12 and is capable of supporting a plurality of objects 44. Thus, according to the first embodiment, object support means 36 resembles an elongated peg or rod which suspends objects 44 from holes or perforations 46 provided therein (see FIG. 2). The longer leg 42 of support means 36 also desirably is formed with a raised portion 42A to prevent the objects from unintentionally sliding off the object support means.

It will be appreciated that hook register 10 finds beneficial usage with articles or objects which are suitable for suspension and whose inventory it is desirable to monitor. Typical items may include packages containing medical items such as drugs, medical equipment, supplies, including for example, catheters and guide wires for angioplasty or other medical items which should be strictly and accurately monitored because of theft, safety, critical need or other concerns. For this reason, the object support means may assume any form necessary or desirable to support the objects supported thereby. That is, the object support means may be configured as a rack, multiple hooks or pegs or similar cantilevered members, a tee bar or other such equivalent constructions.

A switch actuating means 48 desirably configured as a pivotable lever is mounted generally at its midpoint to housing 12 by a pivot pin 50. In the preferred embodiment, a first end of lever 48 projects through an opening 52 in lower housing wall 16. It is also contemplated that lever 48 may be adapted to project through an opening similar to opening 52 and may be provided in any other wall of housing 12 so long as those components necessary for the proper functioning of the apparatus 10 are correspondingly repositioned to accommodate the desired orientation and operation of lever.

A second end of lever 48 is connected to suitable biasing means 54 which in the preferred embodiment is a spring. In the preferred embodiment, the biasing means is a tension spring, however in other embodiments biasing means such as torsion springs, compression springs, elastomeric means or the like may be used. The biasing means normally biases the lever to an "inoperative" position in which the lever extends generally traverse to the longer leg 42 of the object support means 36 of the hook register as depicted in FIG. 1.

It is important that the first end of lever 48 sufficiently project from housing 12 whereby it may be contacted and displaced by a medical item 44 which may be either added to or removed from the object support means. To assure that the lever will interfere with the passage of an object, either into or out of a location on the object support means, a first end of lever 48 is provided with a notch 56. Notch 56 is configured to receive the longer leg 42 of the object support means 36 therein. As a result, when a medical item is removed from its storage location on the object support means, the object contacts and then displaces the lever so as to rotate it outward. The object then passes the lever and once this occurs the biasing means 54 returns the lever to the inoperative position.

A printed circuit board 58 is mounted in the interior of housing 12. Apart from certain circuitry components specifically identified below which are essential to provide an adequate appreciation of the operation of the hook register, it will be understood that circuit board 58 includes printed circuitry and other circuitry components.

Electrical switch means are supported by and electrically connected to the circuit board 58. During operation the switch means serve as part of a sensor that generates signals indicative of the placement of objects into the storage location on object support means 36 or removal of such objects from the storage location. The preferred embodiment of the hook register utilizes a pair of switch elements 60 and 62 as the electrical switch means. In the preferred embodiment, the switch elements are Hall-effect sensors which change states (off-to-on) when a magnetic field is detected within close proximity. Lever 48 carries a compact permanent magnet 64 which serves as an actuator means. The magnetic field produced by magnet 64 is capable of being sensed by switches 60 and 62 to affect changes in their status. The signals indicating changes in the status of the switches are detected by a signal processing circuit 65 which converts the signals to an appropriate form to be received and counted by a microprocessor 66. The microprocessor 66 in the hook register serves as a counter which stores a count therein as later described.

Figure 3:
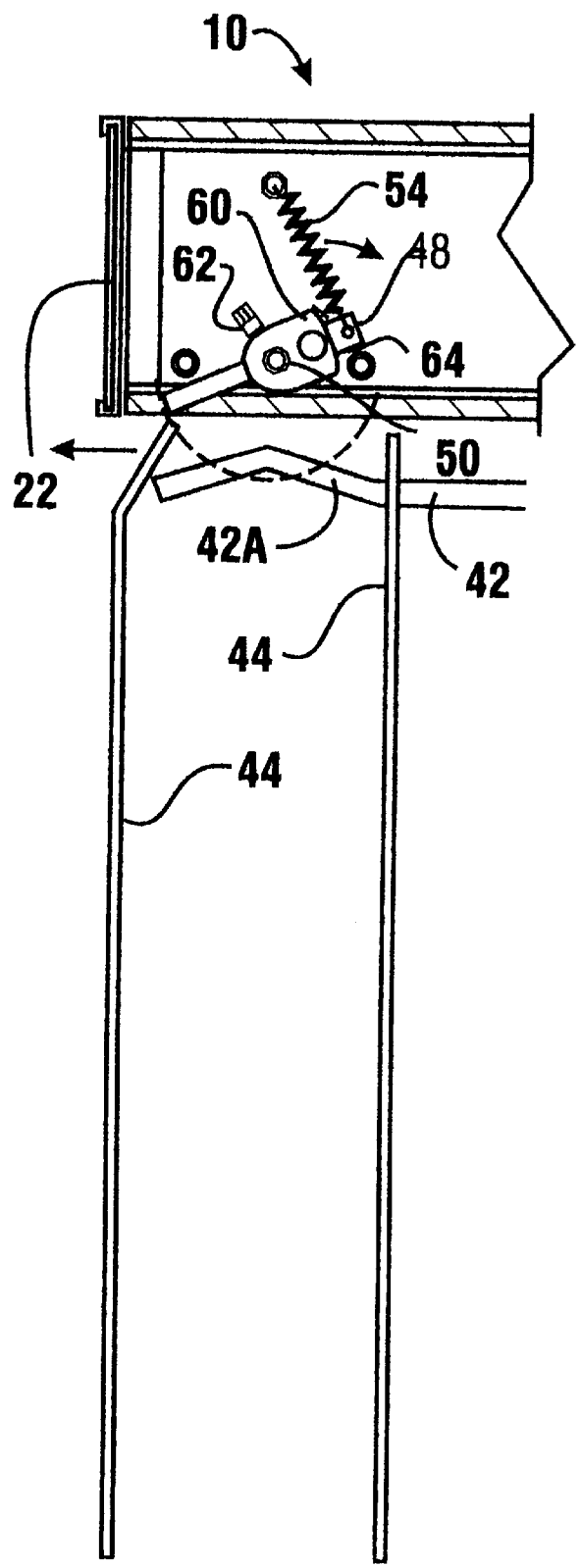
FIG. 3 is similar to FIG. 1 depicting a medical item being removed from the hook register.

Operation of the hook register 10 is graphically represented in FIG. 3. Specifically, the object 44, which is preferably a medical item, is shown at the instant in time when it has fully deflected the lever 48 against the force of the biasing means 54 and has just passed the first end of the lever. At this moment, the permanent magnet 64 is pivoted into a substantially facing relationship with magnetic field detector switch 60. Switch 60 is triggered upon detection of the magnetic field in proximity to the switch element and generates a signal indicating that one object unit has been removed from the object support means 36. Once the medical item has passed off the object support means, the biasing means returns the lever to the inoperative position.

Similarly when a medical item is placed on to the object support means 36, the lever 48 is pivoted in an opposite direction. This causes the permanent magnet to trigger the magnetic field detection switch element 62. This generates a signal indicating that one object unit has been added to the storage location on the object support means. Although in the preferred embodiment magnetic field detection switches are used, other suitable switches such as three-way toggle switches, photo sensors, optical encoders, capacitive or inductance sensors and the like may be employed as sensors to achieve and generate the additive and subtractive article registration signals. Likewise, the switch actuating means may assume forms other than a pivotable lever depending on the type of medical item and storage location involved. For example, a linearly reciprocal lever, a flexible flap or non-contact type sensors may be used in other embodiments.

The microprocessor 66 receives through signal processing circuit 65 the signals generated by switches 60 and 62. The microprocessor contains software programs which record and count the state of the switches each time a change is detected. The number and direction of the changes are counted and stored as a count in the microprocessor. In addition, the microprocessor includes a computer program that enables it to be reset upon receipt of signals from a remote location. In the preferred embodiment, the microprocessor also has stored in association therewith a location identifying indicator that is representative of a number and/or other data uniquely associated with the particular hook register. Each hook register and other dispensing apparatus in the system of the preferred embodiment has a location identifying indicator associated therewith.

The electronic circuitry of the inventory monitoring apparatus also has the ability to communicate its count information to other components of the system of the present invention. In each hook register, the processor 66 is connected through a ribbon cable 68 which is connected with an electrical coupling 70. Coupling 70 electronically couples with a communication bus 34. In this manner, circuit board 58 is enabled to receive power from a remote power source and is enabled to transmit and receive data through communication bus 34.

Figure 9:
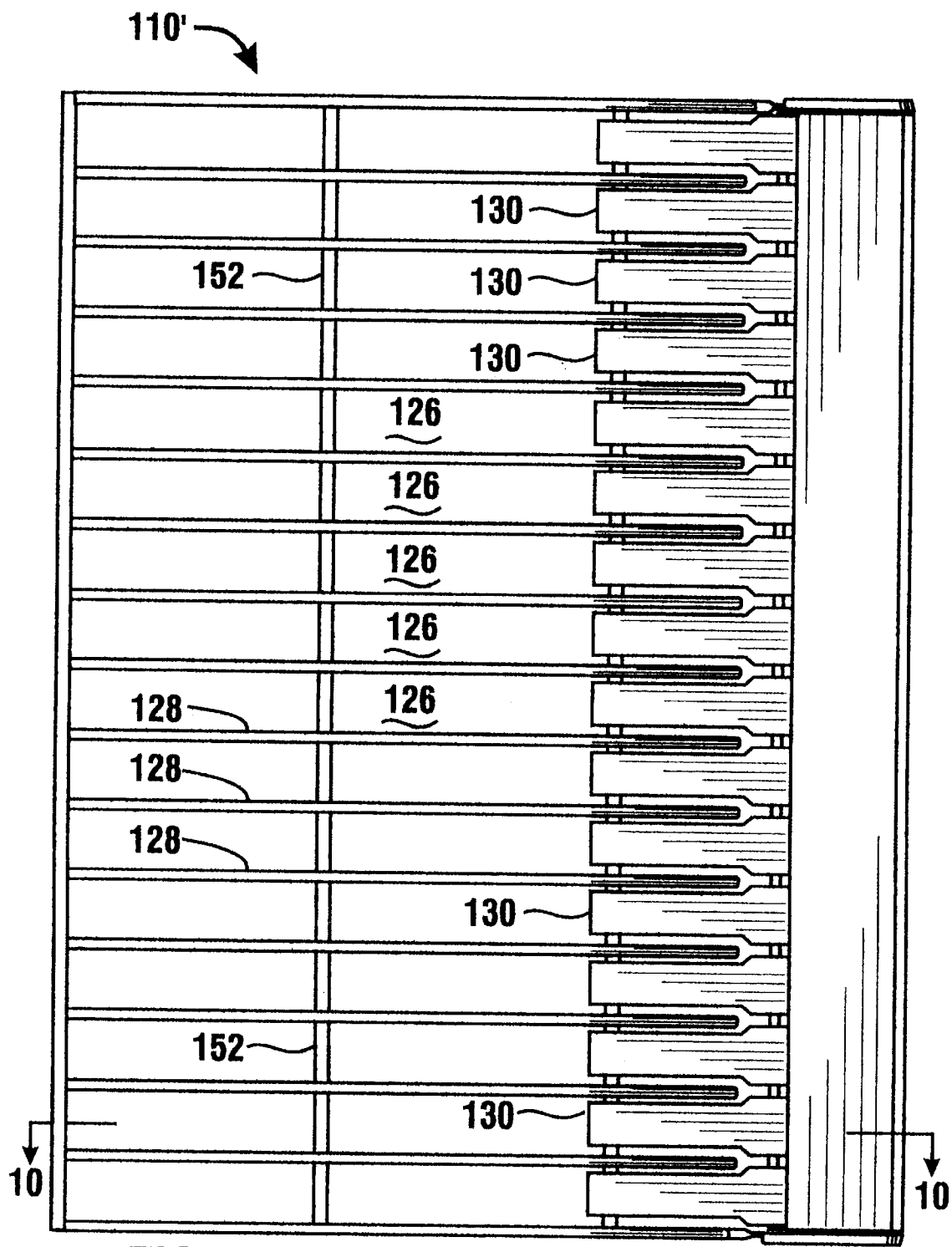
FIG. 9 is a front view of an alternative box register.
Figure 10:
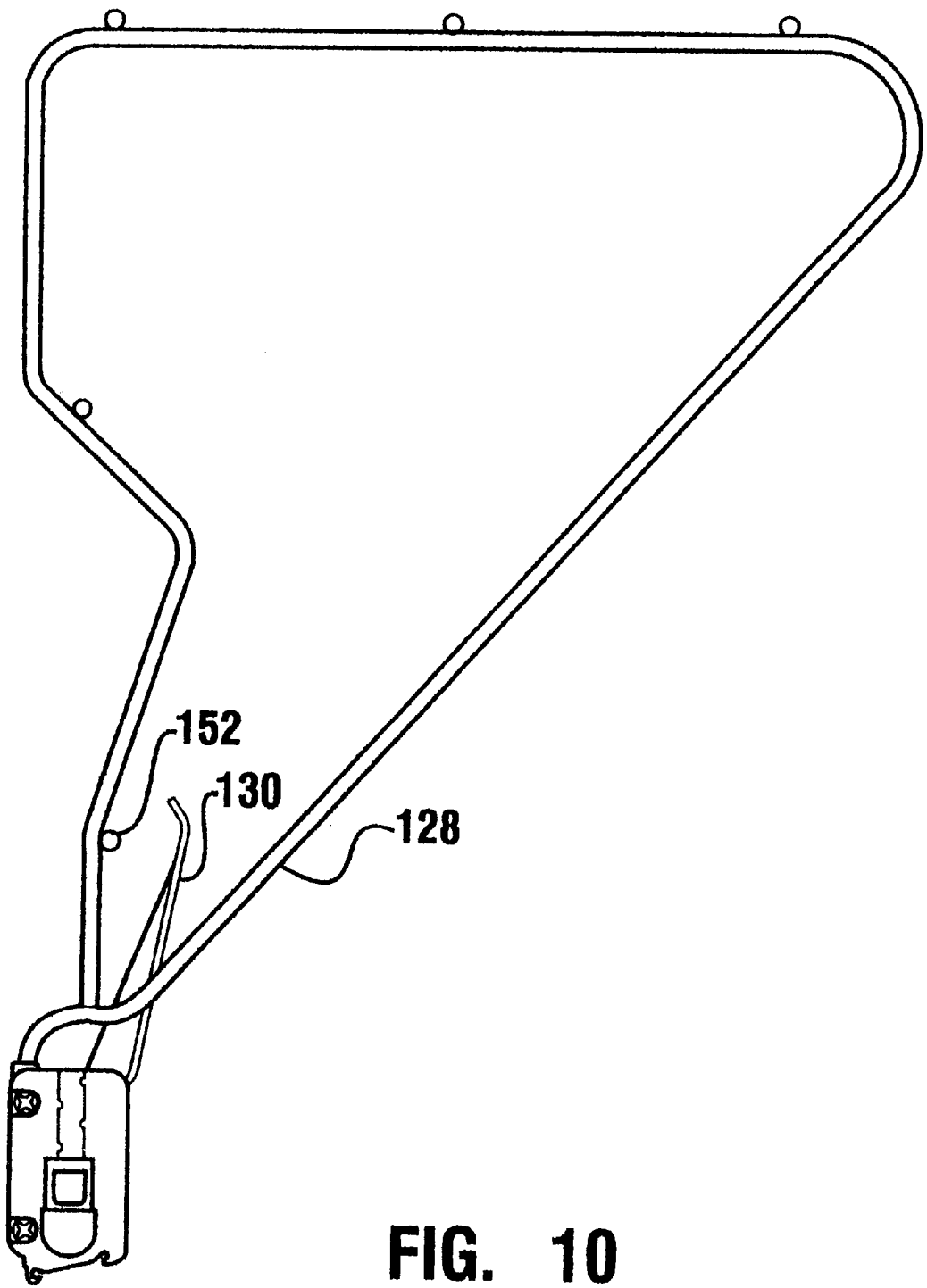
FIG. 10 is a partial side view of the box register along line 10—10 in FIG. 9.
Figure 11:
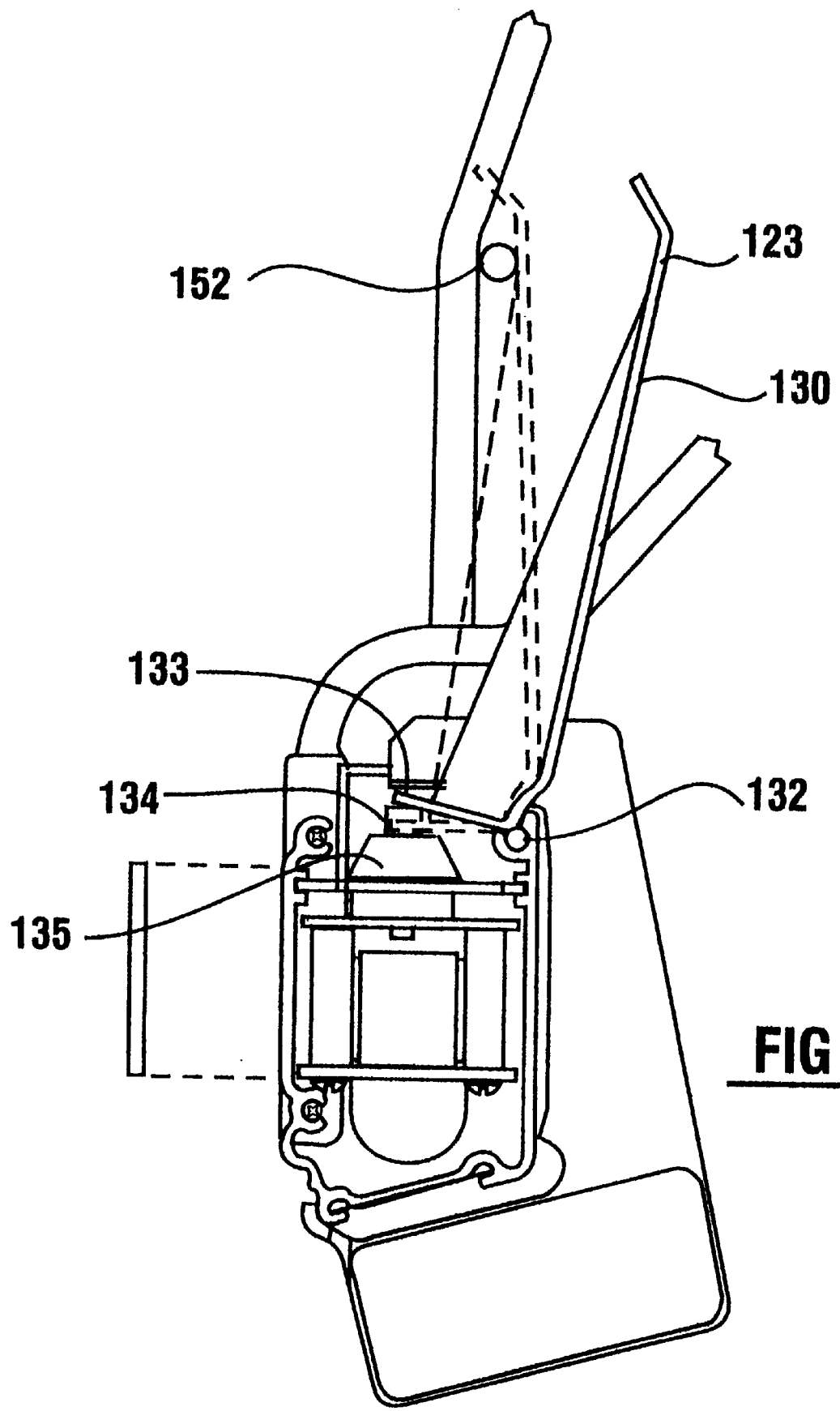
FIG. 11 is an enlarged side view of a switch and lever of the box register shown in FIG. 9.
Figure 12:
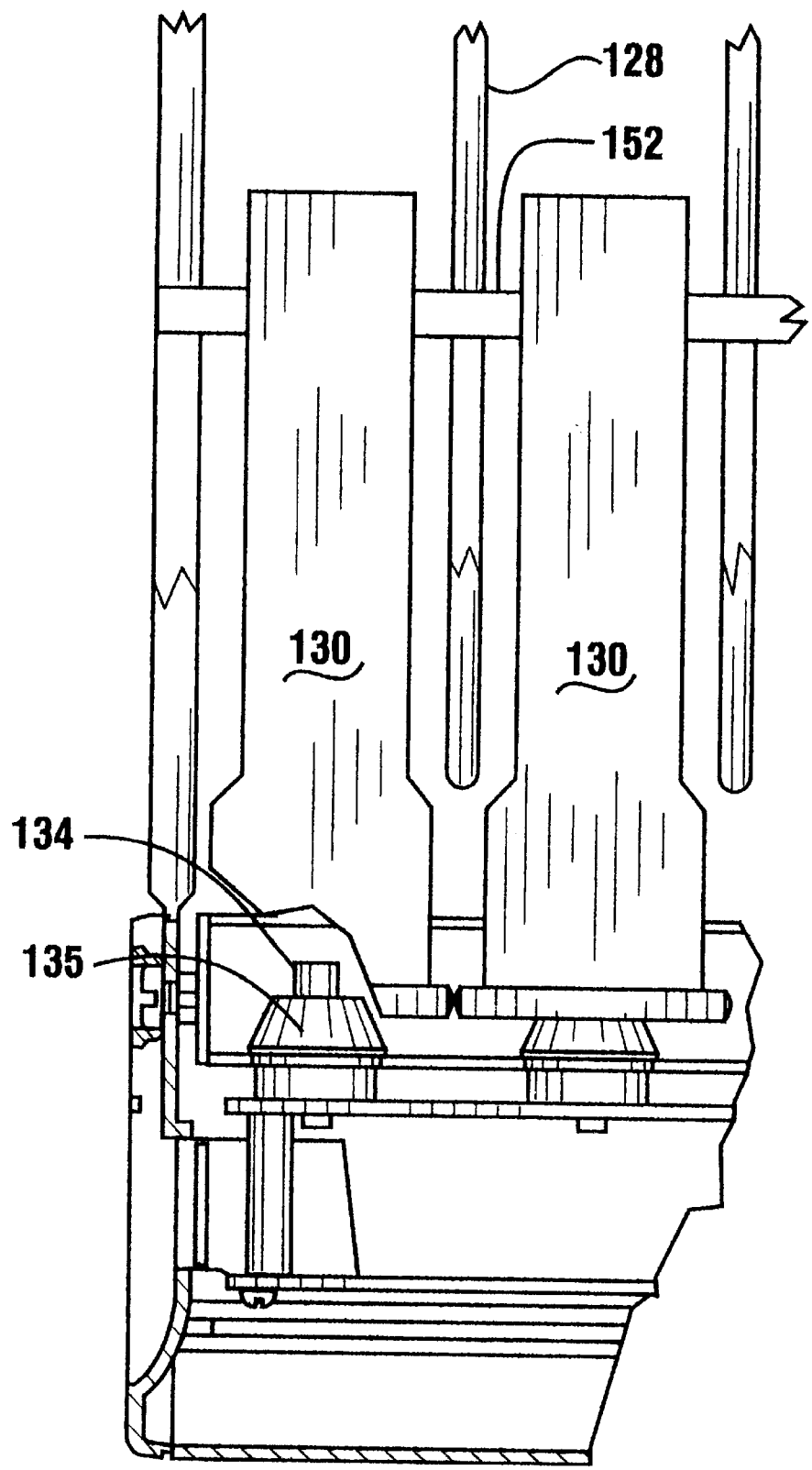
FIG. 12 is a front, partial cut-away view of the lever and switch of the box register shown in FIG. 9.
Figure 13:
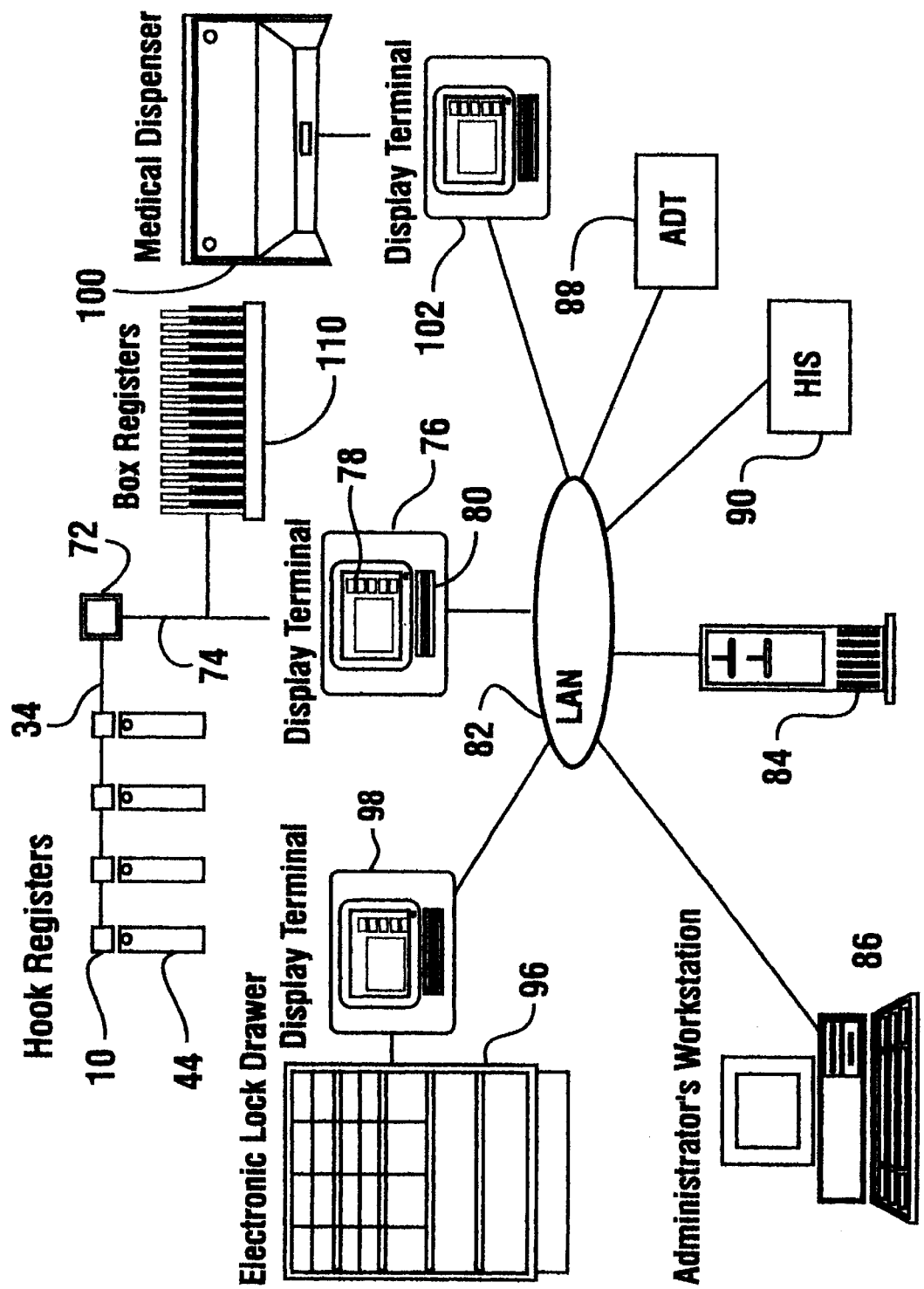
FIG. 13 is a schematic view of the system for monitoring and dispensing medical items including the hook registers and box registers.

The operation of the hook registers 10 in the inventory monitoring and dispensing system of the present invention is best shown with respect to FIG. 9. Each of the hook registers is connected to the data bus 34. Each of the hook registers is connected to the data bus 34, which is connected to a hook controller shown schematically as 72. Hook controller 72 includes a processor and a data store therein which are operable to communicate with each of the hook registers 10. The hook controller 72 is operable to periodically poll each of the hook registers 10 on the data bus. The hook controller reads and receives the count information in each of the hook registers and stores it in conjunction with the location identifying information associated with the particular hook register from which the count was received. After the reading of the count information in the register and transmission of the data to the hook controller 72, the count information in the microprocessor 66 may be erased so a new count can be started. Alternatively, the microprocessor 66 in the hook register may be programmed to store the count information and the time each such count was generated for a period of time while generating new count information. This can be done to assure that usage of items from any hook register can be recovered even in the event of the failure of a hook controller. While FIG. 13 shows only four (4) hook registers connected to controller 72, it will be understood by those skilled in the art that many more hook registers may be so connected on the data bus.

As a result of polling each of the hook registers 10, the hook controller 72 has in its associated processor and data store the count of units taken or added in conjunction with the identifying information associated with each hook register. The hook controller 72 is connected by a further data bus 74 to a data terminal 76 sometimes referred to hereafter as a display terminal. Of course other hook controllers and controllers connected to other types of registers may also be connected to data bus 74. The data bus 74 is used to transmit and receive information from the connected controllers to the data terminal 76.

Data terminal 76 includes a display screen 78 which serves as a data output device. In the preferred embodiment, screen 78 is a "touch screen" of the type known in the prior art wherein a user may input data by placing a finger adjacent to icons displayed on the screen. Sensors overlying the screen sense the position of the finger and convert it to input data. As a result, touch screen 78 serves as a graphical user interface which includes a data input device as well as a data output device. In other embodiments other types of input devices and output devices may be used. Data terminal 76 in the preferred embodiment further includes a card reader 80. Card reader 80 may be used to read data encoded on a magnetic stripe of a user's identification card. Of course in other embodiments of the invention other equivalent reader means for reading coded objects or for reading a user's features such as fingerprints or retina pattern may be used depending on the level of security desired.

In the operation of this embodiment of the invention, a medical technician who wishes to operate the system and remove medical items from the hook registers 10 operates the display terminal. The terminal screen outputs a visual prompt for the user to identify himself or herself to the system by input of identifying data. In certain embodiments, the identification may be accomplished by the user inputting an identification number assigned to the user by touching the appropriate numbers on a graphical keypad presented on the screen of the display terminal such as shown in the user log-in screen in FIG. 38. In other embodiments, the user may be requested to swipe their card in the card reader so that the magnetic stripe thereon may identify the user to the terminal. In embodiments where high security is required, a user may be requested to input both their card and a personnel identification number (PIN) into the display terminal. The PIN has a predetermined relationship to the data on the card, and the data terminal may be operated further only if a proper card and PIN are input.

When a user enters their identifying information at the display terminal, the display terminal communicates through a local area network (LAN) 82 to a remote computer 84 which includes a processor and a data store therein schematically indicated 85. Computer 84 may have greater and faster processing capabilities and more memory than a display terminal. The computer 84 has stored therein or in another computer operatively connected therewith, information records associated with authorized users. If the data input by the user at the display terminal corresponds to a record for an authorized user, then the display terminal will enable the user to operate the system. In alternative embodiments of the system, one or more display terminals may have the additional processing capabilities and the additional memory to perform the functions of computer 84. In such cases the functions performed by the computer 84 may be distributed among the display terminals, or among a network of numerous display terminals and computers, each of which has an associated data store. It should be understood that unless otherwise indicated, for purposes of the invention a network of operatively connected computers and data stores is the equivalent of a single computer with a data store operatively connected thereto.

Upon further use of the display terminal, the user may access certain information about patients, procedures or physicians which is stored in records in the data store of the computer 84 or other computers connected to computer 84 through a local or wide-area network. In the preferred embodiment, the stored records include information about patients. The user may select a particular patient at the display terminal. This is preferably done by the user scrolling through a displayed list of patient names using "keys" presented graphically on the touch screen. The preferred embodiment of the input device includes appropriate programming of the display terminal to include a highlighting device responsive to a user bringing a finger adjacent to an area of the touch screen indicating the patient or other data selected. The selected item is highlighted to indicate it has been selected and further processing will use the highlighted data. However, other input devices for selecting a patient name and other input data may also be used.

In a preferred embodiment, the display terminal displays a patient browser window 222 shown in FIG. 28. The patient browser window includes a list of patients. These patients are preferably patients that are assigned to patient rooms or other areas assigned to the display terminal through programming in the display terminal or the computer 84. Alternatively, the display terminal or connected computer may be programmed to display a list of all patients in an institution at the display terminal.

The patient browser window includes a previous page button 224 and a next page button 226 that enables a user to review or "scroll" through the stored list of patient names which covers several "screens." Of course, the "buttons" are preferably areas on the touch screen produced by the display to direct the user to touch an area which causes the display terminal and/or connected computer to execute a particular function.

Patient browser window 222 further includes an add/find button 228. The add/find button 228 enables a user to either add a patient to the system or to find a patient already in the system. Upon pushing the add/find button 228 the user is presented with another screen which prompts the user to indicate whether they wish to add a patient or look for a patient who is already in the system, perhaps in another area of the institution. Further screens are presented based on the selection input by the user. For example if the user wishes to find a patient, a screen will request the user to input information about the patient such as the last name. The user may be provided with a representation of a keyboard on the touch screen for this purpose or the display terminal may be connected to an alternative input device such as a keyboard. Upon completion of the input of information, the user indicates that the input is complete through the input device. The connected computers are then operative to attempt to find records related to such a patient and display the information on the touch screen.

Alternatively a user may press a sort button 230 to attempt to find a patient. The display terminal and connected computers are operative to sort the list of patients by name and display the sorted list on the touch screen of the display terminal as shown in FIG. 28. Touching the sort button changes the manner in which patients are displayed on the touch screen. For example, touching the sort button may cause it to change the screen so that patients are displayed sequentially by room. The designation on the sort button 230 correspondingly changes as it is togged to indicate how patients are being displayed.

Alternative displays may also be provided in connection with the sort button 230 by programming the computer and the display terminal to sort and display patient data from various patient records in different ways. These may include for example sorting patients by area or ward, by physician, by gender and in other ways that are useful to users of the system. Each time the sort button 230 is touched or "toggled" a new sorted display of patients or information is provided on the touch screen and the designation on the sort button changes to correspond with the method of sorting. The sort button repeats the sequence after it has been toggled through all the sort options.

Returning to a discussion the functions associated with add/find button 228, after first pressing this button the user is presented with another screen where they may indicate that they wish to add a patient. By providing this indication to the display terminal through an input, the user is prompted by screens presented on the display terminal to input the information needed concerning the new patient. The user can input the information through an input device such as a representation of a keyboard on the touch screen of the display terminal, or through an input device such as a keyboard attached to the display terminal.

The display terminal and connected computers are programmed to prompt the user to input the necessary information to add at least one record for the patient to the database of the system. The inputs may also include optional information about the patient as may be available. After inputting the information the display terminal prompts a user to institute an "enter" command which adds the patient and associated information to the system.

In response to the patient information being entered, the connected computers are operative to establish records for the patient in accordance with their programming. They are also operative to establish programmed correlated relationships among records and/or items of stored data related to the new patient. Further in accordance with programming of the system, the system may prompt users of other types of terminals or other data input stations to generate records or input data into records concerning this new patient.

Upon finding the desired patient name in a patient window such as window 222, the user designates that patient's record by touching the patient's name on the screen. Thereafter, the user may remove medical items from the hook registers that are needed by that patient. When this occurs, the number of units of each item removed from a particular hook register is stored as a count in the microprocessor in each hook register. This information is then transferred to the hook controller 72 when the hook register is polled, and is thereafter transferred to the data terminal 76 when the hook controller 72 is accessed through the data bus 74 by the data terminal. As a result, data representative of both the patient and the location and number of units of medical items used for that patient is available in the data terminal.

When the user signs off the data terminal which is done by pushing a log-out button 232, or selects another patient (indicating that the items for the prior patient have been taken), the data terminal preferably transmits the information corresponding to the counts and location numbers of the items used for the selected patient through the LAN 82 to the data store in the computer 84 or another operatively connected computer or data store. Alternatively the data terminal may be sending the data while the user is logged on. The computer 84 functions to correlate the count and location numbers with a medical item record which indicates the types of items stored and the location. This provides an indication of what was used for the patient. In addition, the processor and memory in the computer 84 serve to update the record related to the patient to indicate that the items taken were used for the patient so that the patient may be charged therefore. The location records related to medical items preferably includes or may be referenced to pricing information so that patient may be automatically billed. In addition, the computer 84 also updates its records concerning the number of medical items remaining in storage in each location.

The computer 84 is operable in this embodiment to maintain a continuous real time record of how many units of medical items are stored in each of the locations. If the number remaining in any location has reached a lower limit, the computer 84 is programmed to provide a warning of the need to replenish the supplies at that location to an administrator terminal or workstation 86. The administrator's workstation 86 is also a computer with a processor and data store and is connected through the LAN. It has input devices such as the keyboard and mouse shown and an output device such as the screen shown. The terminal 86 may also have other input and output means such as a touch screen, spoken word recognition, audio output or signal outputs connected to printers or other devices. Of course, the need to replenish the supplies may be indicated on the screen at the administrator's workstation or in other output locations including the data terminals in the area where the hook registers need to be replenished.

In other embodiments, the data terminal may be used to help medical technicians or nurses select medical items for patients. The computer 84 or other connected computers have associated data stores which include records which contain information on medications prescribed for patients. The computer 84 also preferably includes records related to medical procedures as well as physicians in its data store. This information may be accessed at the display terminal by the medical technician or nurse who is obtaining supplies for use in such a procedure. By accessing the stored data records related to the procedure, the technician can read a record which includes information such as the items that are normally used in such a procedure. As a result, the technician may note these items and may remove them from the hook registers while viewing the procedure record to ensure that everything normally needed is transferred to the operating room. In addition, the procedure records may be accessed in connection with a physician record related to a physician who will perform the procedure. Such records may include additional medical items that the particular physician requires to have present in an operating room when conducting a particular procedure. This may include additional medical items or particular types of medical items that the physician prefers. It may also include convenience information such as the particular type of music the physician prefers to have played in the operating room during a procedure or other items that the particular physician prefers to have available.

In other embodiments of the invention, computer 84 or other connected computers may be programmed to have in its data store, and may provide in response to a request at a display terminal, a schedule of procedures in a particular hospital operating theater. This enables the medical technician or nurse participating in the procedure to locate the patient scheduled for a procedure using the display terminal, and to access therewith the records related to the physician and the medical items that will be needed for the procedure. As a result, the technician or nurse may go to the hook registers, obtain the necessary medical items and have them immediately charged to the patient's account. Alternatively, if medical items which are dispensed are involved, the items may be simultaneously dispensed together. If after the procedure not all of the items that were originally taken were used, the items may be returned to inventory and credited to the patient's account if appropriate. Alternatively, such items that are partially used may need to be wasted. This is generally done by the user identifying himself or herself to the display terminal 76 and again identifying the patient to the system using the touch screen 78 in the manner previously described. Replacing the unused items back on the hook registers 10 automatically creates a record that such items were returned and the patient's account will be credited in the computer 84. Alternatively returned medications and wasted items are returned to designated areas and records thereof are generated and stored.

Because of the large number of records that are stored in the data store of the computer 84 and other connected computers, a large number of reports related to inventory usage may be generated. This can be accomplished by using database software such as Paradox® in computer 84. Alternatively, relational database software such as Oracle® is preferably used. Further, because the inventory at each location is monitored, messages requesting transfers of inventory from areas where there are excess units to areas where there is a need can be automatically generated by the computer and displayed at the administrator's workstation. The computer 84 also operates to keep a running tally in the data store of what has been used by each patient as well as what has been taken by each user and used by patients of each physician. This further allows monitoring of usage and allow potential abuses to be uncovered. The computer 84 is ideally programmed to look for patterns of dispensing activity that have been programmed into the computer's memory as potential abuses and to display a report thereof at the administrator's workstation. Such potential abuses may include taking particular items at abnormally frequent intervals. The computer 84 may also be programmed to provide reports from the database concerning what particular users have dispensed during a given time period and what particular physicians have used or prescribed for patients.

In the described embodiment of the system of the present invention, the administrator's workstation 86 is used as a primary tool for the monitoring of inventory. The administrator's workstation is used to program the particular type of medical item stored in the location at each of the hook registers and in other types of registers in the system. This is done by creating a record for each location in the data store. The administrator's workstation is also used to set the level of the minimum acceptable number of units of each item at each location so that an indication may be given of a need to replenish or transfer stock. This is programmed as a minimum for each location, and an indication is given when the minimum is reached. Further, the administrator's workstation preferably includes electronic ordering capability so that when supplies of a particular item are reduced to a particular level, a purchase order to replenish the stock is sent automatically to the manufacturer. The ordering and source information is also optimally part of or referenced with the associated record with the item in the data store. As a result, the administrator's workstation is programmed so that when the quantity of an item on hand falls to a particular level, an order is communicated to the manufacturer of the needed item directly over a telephone or other data line via a modem, indicating electronically the item needed, an order quantity and a date by which the items must be received. The order quantity data may be preprogrammed or may be calculated automatically by the computer using a program that generates the order quantity based on rate of use. Likewise, the delivery date may be a programmed time period after issuance of the order, but may also be programmed to be a rush order if the "on hand" quantity has fallen to a second lower level or if the use rate is above a programmed level.

The administrator's workstation may also be used to establish records for authorized users and to set varying levels of security for authorized users at different types of display terminals. Although in the described embodiment, the administrator's workstation is the primary control for the system of the present invention as shown in FIG. 13, the hospital's other computer systems including the admission-discharge-transfer (ADT) system 88 and the hospital information system (HIS) 90 are also connected to the local area network 82. This enables the patient data in the computer 84 to be input and output to the ADT system 88 and records relating to patient activity or other activities to be received from or stored in the HIS, which is typically the long term data storage facility related to patients. The system is also preferably connected to other computer systems in the institution such as a pharmacy system 89 which provides information on medications prescribed for such patients. The system may also be connected systems in dietary and food services and in other institution areas. Each of these systems may contain multiple processors and data stores which transmit selected data to and from the LAN 82. This enables the exchange of data throughout the hospital's computers which facilitates both record keeping, patient billing and monitoring of its inventory.

Figure 4:
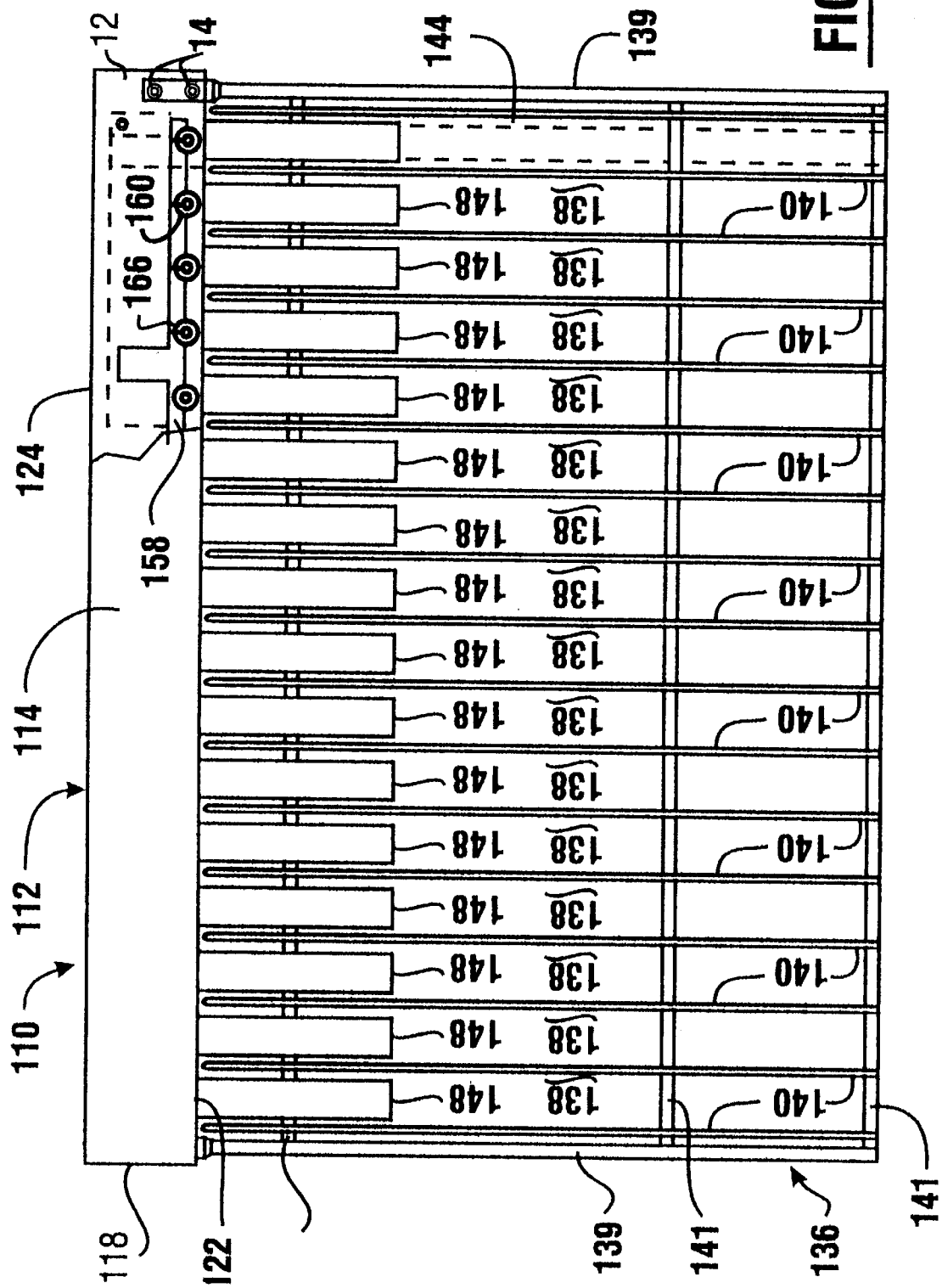
FIG. 4 is a partial cut-away top plan view of a further inventory monitoring apparatus of the present invention called a box register.
Figure 5:
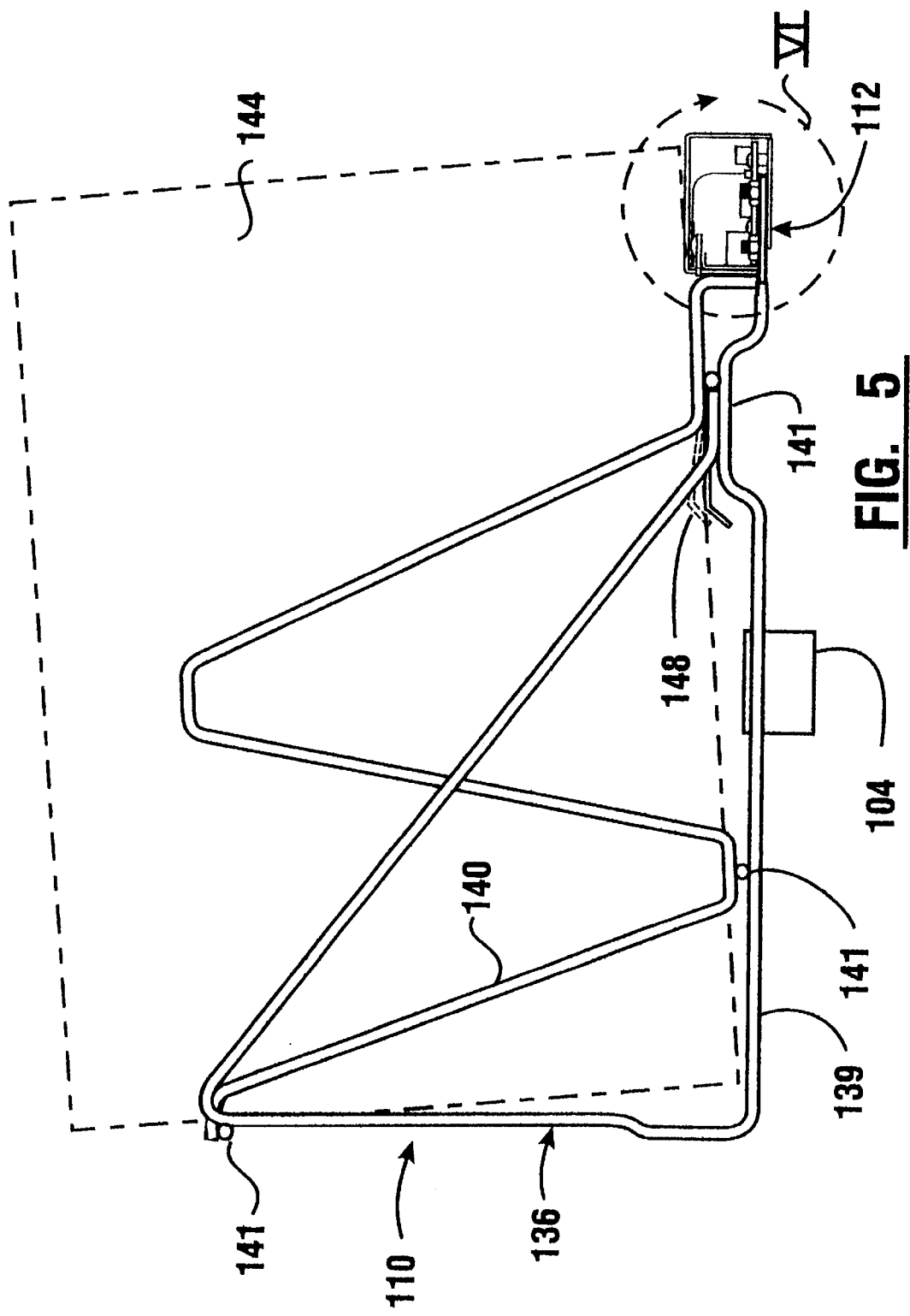
FIG. 5 is a side elevation view of the box register shown in FIG. 4 as seen along line v—v of FIG. 4.
Figure 6:
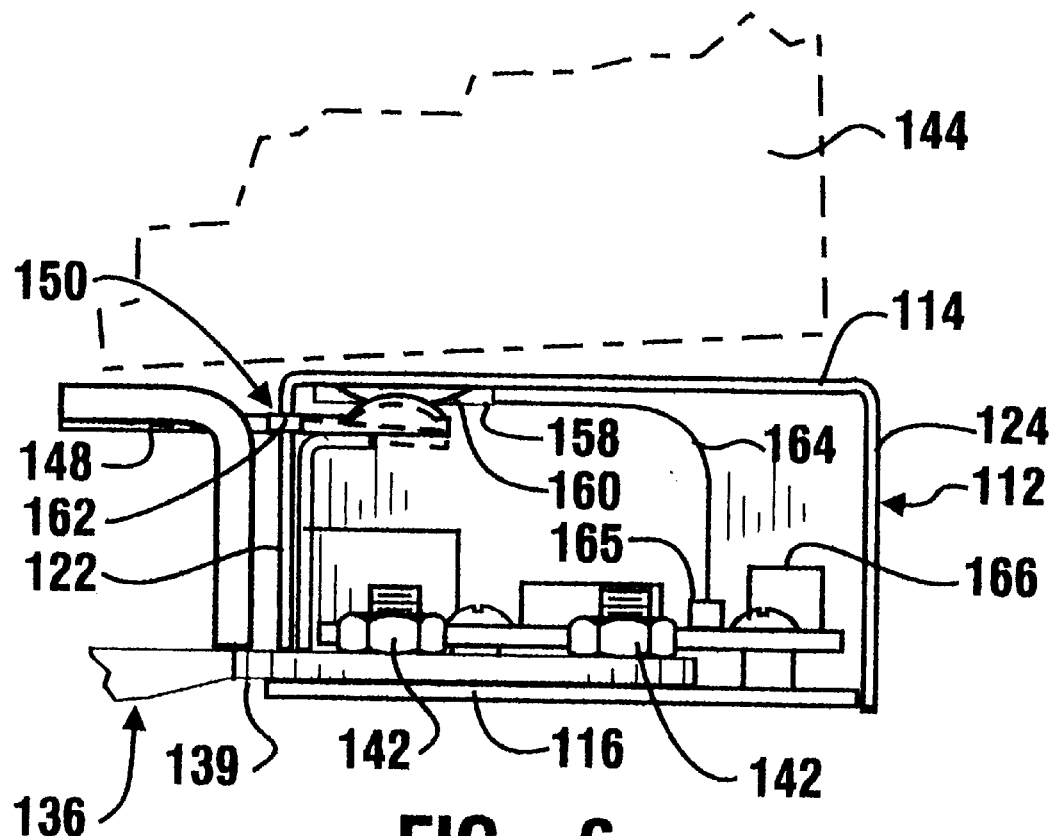
FIG. 6 is an enlarged view of the circled portion VI shown in FIG. 5.

The hook registers 10 which are optimally constructed for supporting hanging items are only one type of dispensing device that can be used with the present invention. FIGS. 4 through 6 reflect a further embodiment of an inventory monitoring apparatus designated by the numeral 110. Apparatus 110 is called a box register as it is optimally adapted to include storage locations for holding boxes or box-like articles. Box register 110 includes an elongated housing 112 including an upper wall 115, a lower wall 116, end walls 118 and 120, a front wall 122 and a rear wall 124. Like housing 12 of hook register 10, housing 122 may be fabricated from any durable material such as plastic or metal. Although not shown, it will be understood that a clip assembly similar to clip assembly 26 of FIGS. 1 and 2 or a similar attachment mechanism may be used to detachably fasten the housing to a wall. Alternatively, apparatus 110 may rest on a level shelf, tabletop or reside in a cabinet. Each box register 110 is connected to a communication bus 74 (see FIG. 13).

With regard to the box register, in this embodiment, an object support means is represented by reference numeral 136 which support means may assume the form of a receptacle having at least one or preferably a plurality of compartments or object storage sites 138 which are locations wherein medical items may be stored. In this embodiment, object support means 136 is constructed as a multiple compartment, heavy gage, stiff metal wire rack including a pair of upright truss-like end walls 139, a plurality of spaced apart storage site divider walls 140 situated between and generally parallel to the end walls 139 and a plurality of transverse members 141 affixed to the end walls 139 and divider walls 140. The end walls 139 are desirably secured by suitable mechanical fastening means 142, such as nuts and bolts or the like to lower wall 116 (as shown) or any other wall of the housing 112.

As shown in the figures, the object support means 136 is adapted to support objects 144 of substantially uniform dimensions (one of which is shown in phantom in FIGS. 4 through 6) in a substantially upright orientation. For example, objects 144 may be generally uniformly sized relatively thin boxes or similar packages which may contain various designated types of medical products. The object support means as illustrated is thus capable of supporting an object on four sides thereof, i.e., the bottom, back and both lateral sides of the object (see FIGS. 4 and 5). In this fashion, an object 144 may be removed from the object support means 136 by lifting it forward (to the right as shown in FIG. 5) and/or upward. The bases of the divider walls 140 are situated at a lower elevation than the upper wall 114 of housing 12 (FIG. 5) whereby the objects 144 are caused to be tilted slightly rearwardly such that the back sides of the objects maintain contact with the rear of the object support means 136.

Although the described embodiment of the object support means 136 supports the objects 144 such as boxes in substantially upright or vertical position, the present invention also contemplates rack geometries whereby objects may be supported substantially horizontally, at acute angles or in a staggered array incorporating one or more angular support orientations. Further, the spacing between the divider walls 140 need not be uniform in which case storage sites 138 of variable dimensions may be provided in the same object support means 136. Of course the object support means 136, like housing 112, may be fabricated of metal or from any high strength substantially rigid plastic or other suitable material.

Box register 110 includes switch activating means 148. The switch activating means 148 includes one or more levers pivotally mounted at 150 (see FIG. 6) to housing 112 in a manner described hereafter. The levers 148 correspond in number to the number of compartments 138 which are the storage locations provided in the object support means 136. A first end of each lever 148 projects from the housing 112 into a respective one of the storage sites 138 and a second end of each lever extends into the housing as most clearly seen in FIG. 6. The first end of each lever protrudes from the housing for a distance sufficient to be contacted and displaced by an object 144 when such object is added to the object support means 136. Biasing means later discussed return the levers to inoperative positions upon removal of an object from the corresponding storage site.

Referring to FIGS. 4 and 6, as is the case with the hook registers described above, the box registers likewise have printed circuit boards therein designated 158 one of which is shown. Circuit boards 158 are mounted in the interior of housing 112. Circuit boards 158 include printed circuitry and other circuitry components which are not illustrated or described in detail except to the extent necessary for a proper understanding of the present invention.

Electrical sensor means are supported by and electrically connected to circuit board 158. The sensor means generate signals indicative of the placement of an object onto and the removal of an object from the object support member 136. According to the preferred embodiment, the sensor means comprises one or more discrete force actuatable switches 160 such as snap-type internally resilient dome switches or other type electrical switches. Switches 160 are spaced apart along the length of circuit board 158 and correspond in number to the levers 148 whereby the second end of each lever operates a separate switch.

The switches 160 generate real time counting signals indicative of the total inventory of objects 144 carried by the object support sites which are occupied and those which are unoccupied at any instant in time. Thus when a lever 148 is caused to pivot in one direction by an object that is placed into a storage location, the second end of the lever closes its respective switch 160. This is reflected by the solid line image of lever 148 depicted in FIGS. 5 and 6. Switch 160 in turn generates a registration signal indicating that an object has been placed into the storage location and at which storage site the object has been added.

Conversely, when an object is removed from the object support means, the biasing force from the internal resilience of the dome switch 160 returns the lever to its inoperative position as is reflected by the dash line image of lever 148 illustrated in FIGS. 5 and 6 whereby the switch is open. In this position, the switch generates a registration signal which reflects that an object has been removed from the storage location. Additionally, if mechanical switches other than dome type or other similar switches possessing internal resiliency are employed as the electrical switch means, then biasing means such as springs or elastomeric means may be provided to assure that the switches change electrical condition upon removal of objects from the object support means 136. Alternatively, certain switch types have built-in springs which provide the biasing force. Although dome type switches are used in embodiments of the box registers, other suitable sensor means such as two-way toggle switches, momentary contact switches, photo sensitive switches, capacitive or inductance sensors and the like may be employed to affect the generation of additive, subtractive and object locating registration symbols.

Figure 7:
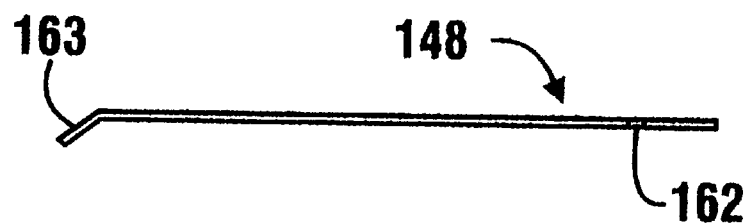
FIG. 7 is a side view of a lever used in the box register shown in FIGS. 4 and 5.
Figure 8:
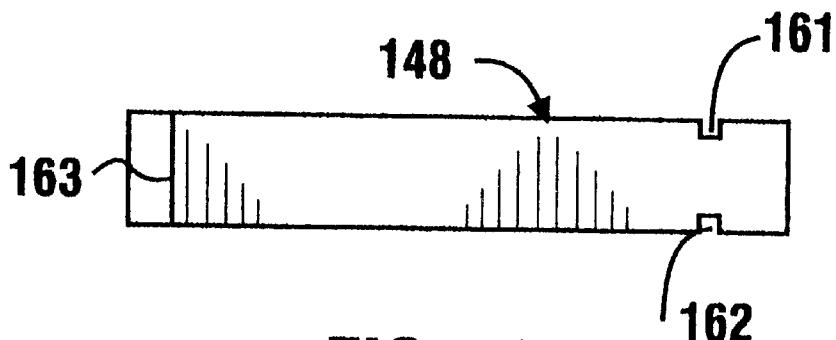
FIG. 8 is a top plan view of the lever shown in FIG. 7.

FIGS. 7 to 8 show on an enlarged scale a lever 148. The lever desirably includes a pair of opposed notches 161, 162 which generally separate the lever into its first and second ends and, in cooperation with mating slots provided in the front wall 122 of housing 112, establish the pivotal connection 150 of the lever relative to the housing. Further, each lever 148 is preferably provided with a downwardly sloping lip 163 at the leading edge of its first end to facilitate insertion of the objects 144 into the storage sites 138.

The signals indicating changes in the status of the switches 160 are transmitted by wire or other acceptable signal conducting means 164 whereupon they are detected by a signal processing circuit 165 which converts the signals to an appropriate form to be received and counted by a microprocessor 166. The microprocessor 166, like microprocessor 66 of the hook registers 10 described above, contains software programs which record the state of the switches each time a change is detected. The microprocessor 166 also counts and stores a count indicative of the number and direction of changes in state as they occur. Further, the microprocessor 166 includes the unique location identifying indicator associated with each of the storage locations in which any changes in the presence of a medical item have occurred. Alternatively, the microprocessor 166 may keep track of the times such changes have occurred.

While not illustrated it will be appreciated that the hook and box registers are preferably remotely powered through the associated bus connections. In other embodiments they may be locally powered. Further, in other embodiments the registers may include LED or LCD displays on the registers for indicating the powered condition of the particular register or the fact of a change in the status of inventory items at the location. Of course suitable LED or LCD indicators may also be used for other purposes such as indicating the particular type of item to be stored, that the register is in a restocking mode, or that the amount of inventory stored in the location has fallen below a critical level. This is accomplished by programming in computer 84, or programming in the other processors connected to LAN 82 to output such an indication under such conditions.

An alternative embodiment of a box register 110' is shown in FIGS. 9 through 12. Box register 110' is similar to the previously described box register 110 except as expressly noted herein. The box register 110' includes a plurality of compartments 126 which are separated by divider walls 128. Each compartment has located therein a lever 130, which is movable about a pivot 132 (see FIGS. 11 and 12). The lever includes an object engaging leg 123 and a switch actuating leg 133. The leg 133 is engageable with an actuating projection 134 of a switch 135. The switch 135 includes an internal spring which biases the actuating projection outward from the switch. The switch operates to change its electrical condition when the actuating projection is depressed.

Objects or items such as boxes holding medical supplies are stored in the compartments 126. The presence of an object in the compartment engages the object engaging leg 123 and moves the associated lever 130 to the position shown in phantom in FIG. 11. In this position lever 130 is in abutting relation with a stop member 152 which bounds the rear of the compartment. The stop 152 prevents the object engaging leg of lever 130 from being rotated rearward beyond the position shown in phantom. When object engaging leg 123 is in engagement with stop 152, switch actuating leg 133 depresses actuating projection 134 of switch 135 resulting in the switch having a first electrical condition.

Upon removal of the box or other object from the compartment, actuating projection 134 moves outward in response to the biasing force of the internal spring as the object disengages lever 130. Outward movement of actuating projection 134 causes switch 135 to change its electrical condition. As in the earlier described embodiment of the box register this change is noted in conjunction with the location information in the box register's associated microprocessor, similar to microprocessor 166.

Although the box registers shown are a single tiered rack, the object support means may comprise a multi-tiered rack or a plurality of rows and/or columns of cubicals whereby each of the storage sites or cubicals may be appropriately fitted with a switch actuating means such as a lever.

In the preferred form of the invention, the box registers are connected through bus 74 with the display terminal 76. The display terminal periodically reads the count information in the microprocessor 166 associated with each of the box registers and receives changes in the count information associated with each of the storage locations in the box registers.

A user may operate display terminal 76 to indicate the appropriate patient for which material taken from the box registers will be used in the manner previously described with regard to the hook registers. In addition, the administrator's workstation is used in the setup of the system to assign the particular type of medical item to be stored in each location in the box registers which is stored in a record in computer 84. However, unlike the hook registers which may store a substantial number of units of the particular type of medical item in each location, a box register is adapted to store only one such item in each location. Therefore, in some embodiments several adjacent locations in the box register are designated for containing the same type of medical item.

As is also the case with the hook registers, a user of the system who is replenishing inventory to the box registers may operate the display terminal to so indicate using the touch screen data entry device that he or she is replenishing inventory. In this case, the records in computer 84 will be updated to indicate the units of inventory added in each of the storage locations. No patient is credited for the items stocked in the locations and a record in the data store concerning the number of such items on hand but not yet placed for use in a location is also updated. In alternative embodiments, a bar code is applied on the various items stored in the hook and box registers. A bar code reader or scanner shown schematically as 104 in FIG. 5 is positioned in the hook and box registers so that the code on the item is read as it is placed or removed from a location. The bar code scanner generates signals that are interpreted by software for reading bar codes which runs in computer 84 or another terminal in the LAN 82. A data store associated with the software includes information which correlates each bar code identifier with a particular medical item. This provides a check that the item actually stored or taken is the type that is recorded as stored in that location. If an error is made an alarm may be given, either at the register, display terminal and/or the administrator's workstation. Alternatively, the bar code on the medical items may be used to "set up" the system, so that the system records the fact that a particular medical item is stored in a particular location as a result of having read the bar code thereon as the item is placed therein. This avoids the need to program the administrator's workstation with this information. The bar code scanner can be provided in addition to the indicator which indicates an item is added or removed. Alternatively, the bar code may be read as each item is removed from a location on a hook or box register and the use for the patient of the item recorded directly in response to reading the bar code signals and identifying the patient at the display terminal.

The information included in the data store with respect to particular items may also include a date by which perishable items must be used. The user stocking such items in the locations can input such information using the input device of the data terminal. Items having a limited shelf life are preferably stored in the box registers where the "use by" date can be uniquely associated as part of the record for the only item in the location.

The system can also be used with other types of devices that are used to indicate that an item has been taken for a patient. One such device is a manual input register where a nurse or other medical technician manually indicates that an item has been taken.

In one embodiment a manual register is structurally similar to box register 110' except that it does not include compartments or levers. The actuating projections of the switches are connected to manually engageable buttons. The system is programmed so that the momentary change in electrical condition of a switch resulting from depression of a particular button represents the taking of one unit of a particular item from storage. Preferably each button is labeled with indicia representative of the item that it is associated with.

In the case of a manual register, the nurse or medical technician ques up the patient who will receive the items on the screen of the data terminal and touches the screen to select that patient. The user pushes each button on the manual register corresponding to the type of item taken. By pressing the button once for each unit of an item taken, data is stored in the micropressor associated with the manual register which is representative of the particular button location pushed and the corresponding count associated with that button. This information is correlated with the patient record in the same manner as occurs with the hook registers and box registers.

The system of the present invention may also be used in conjunction with other types of dispensing devices. An example of such a device is an electronic lock drawer 96. The electronic lock drawer may be used to store narcotics or other articles, the use of which is highly restricted and which are not suitable for storage in a hook or box type register of the type previously described. Alternatively, the electronic lock drawer may comprise a secure enclosure housing hook registers or box registers in its interior. The function of the electronic lock drawer is to hold the restricted items and provide access thereto by opening a locking mechanism of the unit only when a set of predetermined conditions are satisfied. The electronic lock drawer is but an example of one of many possible storage or dispensing devices which incorporate an access control device which selectively controls access to the storage locations for medical items or which makes medical items accessible by dispensing them to a user.

In one embodiment of the invention the electronic lock drawer is connected to and the opening thereof controlled through an adjacent data terminal 98. Data terminal 98 is similar to data terminal 76. Data terminal 98 is connected to the electronic lock drawer 96 and is operable to unlock the lock thereto upon receipt of appropriate signals from computer 84. Of course although only one electronic lock drawer is shown in connection with data terminal 98, additional electronic lock drawers may be connected thereto.

In the preferred form of the invention, information about each type of restricted material housed in each electronic lock drawer is stored in a record in the computer 84. To gain access to these materials a user may first identify himself or herself to the data terminal in the manner previously described. Preferably for highly restricted items, computer 84 requires not only a user to input an identification card and PIN number but also a second authorized user to input their coded card and PIN number. The purpose for requiring two (2) authorized users to be present to open the electronic lock drawer is so that the items removed and their disposition may be verified.

Preferably, the computer 84 has stored in the patient record, information about the medications that the patient has been prescribed or authorized to be given. As a result, the user may use the data terminal to select the patient name and to request the opening of the electronic lock drawer so the user may take the medication for the patient. This is done using the touch screen of the data terminal as an input/output device. Thereafter, upon proper input of a further authorized user's verification information, the electronic lock drawer will unlock in response to signals sent from the computer 84 to the data terminal 98 and from the data terminal 98 to the lock drawer 96. Thereafter, the user may remove the medication from the lock drawer in the presence of the verification user and reclose the unit. Upon the user inputting a verification input to the data terminal that the medication has been taken, the associated record of use and the charge therefore is automatically added to the patient's account by the computer 84.

It does not matter if a medication that is stored in the electronic lock drawer is not listed as one the patient is authorized to receive in the patient's records in the computer 84, the authorized user may still access the electronic lock drawer. A user may input a request through the data terminal for a listing of medications available. In response the computer 84 outputs to the data terminal a listing of the available medications and the dosages. The computer may also provide information on the location of each medication. The user may then select a particular type of medication and then input through the data terminal a request for a listing of patients which again is provided from the records in the data store of computer 84. By selecting the patient who is to receive the medication (and when appropriate providing the necessary verification from a co-authorized user) the appropriate electronic lock drawer will unlock and allow access to the medication. Upon verification input to the data terminal from the user that the medication has been removed, the computer will charge the patient's account therefore by updating the patient's record. Of course as is the case with the other medical item storage locations previously described, computer 84 also operates to keep track of the inventory of various items inside the electronic lock drawer 96 to assure adequate stock. The computer is also programmed to record the users and verification users who have removed items from the electronic lock drawer and the types of items taken so that any shortages or patterns of abuse may be automatically noted. Further, as discussed previously, data terminal 98 may be used to access information in the computer concerning procedures and physicians so that items in the electronic lock drawer 96 may be taken to an operating theater in advance of a surgical procedure.

Of course data terminal 98 may be used like data terminal 76 to credit a patient's account for items returned from inventory as well as to indicate replenishment of inventory in the electronic lock drawer. If a narcotic substance is to be returned the computer is programmed to have a verification user verify the returns. Returns are preferably made into special one way receptacles so that returned items can not be removed by unauthorized persons.

Another type of dispensing device used in embodiments of the invention are devices which provide storage for medical items under controlled environmental conditions. This is represented by a refrigerator 450 shown in FIG. 13. Refrigerator 450 has an interior area which holds medical items of one or more types therein. Access to the interior area of refrigerator 450 is controlled by a lock module 452. Lock module 452 controls access to the medical items in the interior area of the refrigerator. The lock module 452 is controlled from the display terminal 98. The operation of the refrigerator and the lock module is generally similar to that discussed for compartments in the electronic lock drawer 96. It should be understood that embodiments of the invention may include subcompartments within the interior area of the refrigerator, and access to each subcompartment may be controlled selectively from the display terminal or from other computers within the system. The system may also have a plurality of refrigerators or other environmentally controlled chambers, and access to each may be controlled individually. This enables providing various levels of security for the different types of medical items housed in each refrigerator.

Access to the interior areas of the refrigerators is obtained by one or more authorized users as required by the programming of the system. This is accomplished in the manner previously discussed in connection with the electronic lock drawer. A signal from the display terminal 98 or other connected computer is sent to the associated lock module so as to enable the user to access the interior area of the refrigerator and the medical items held therein.

Figure 50:
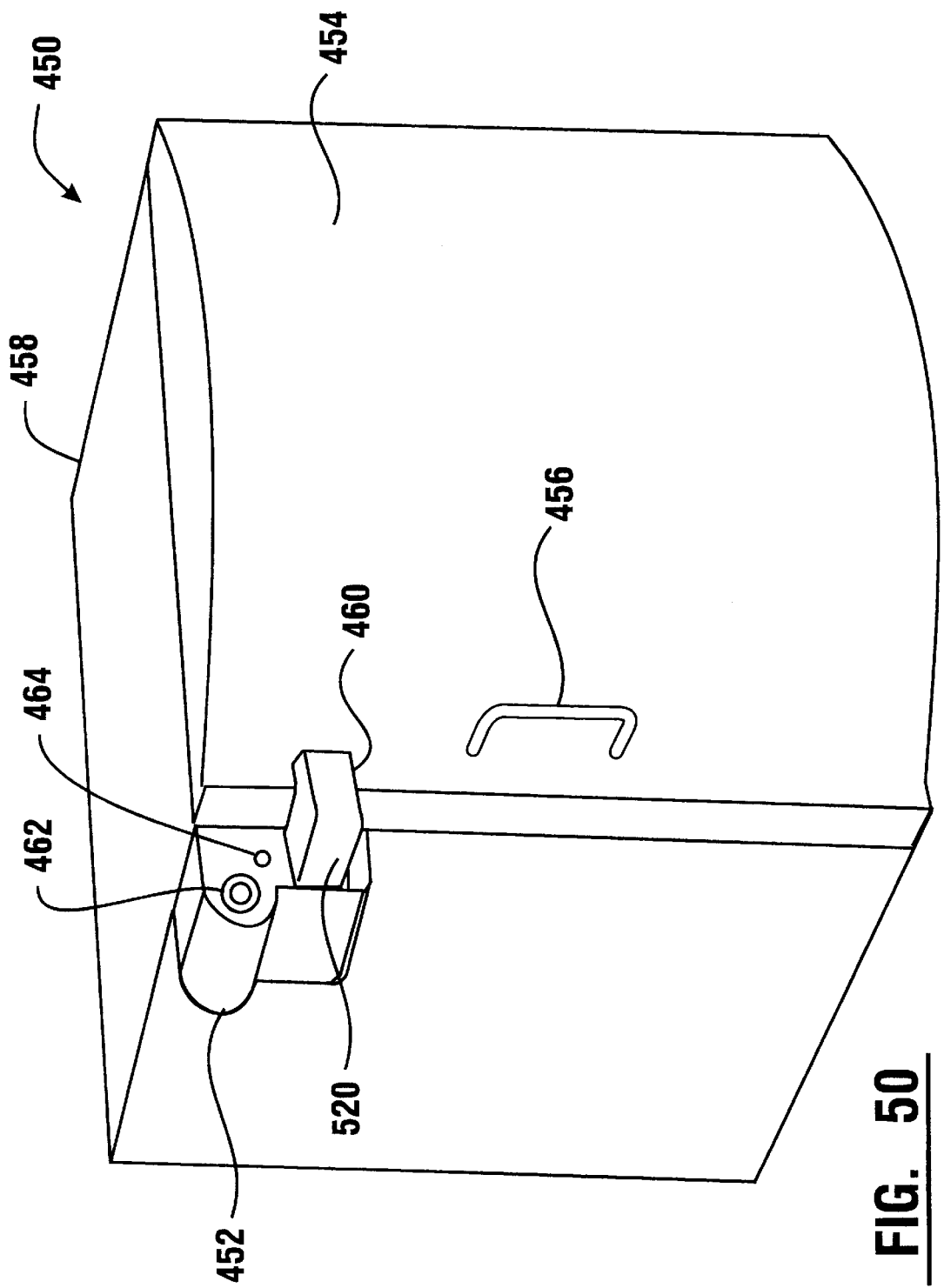
FIG. 50 is an isometric view of a refrigerator which holds medical items in an interior area, the refrigerator having a lock module mounted thereon.
Figure 51:
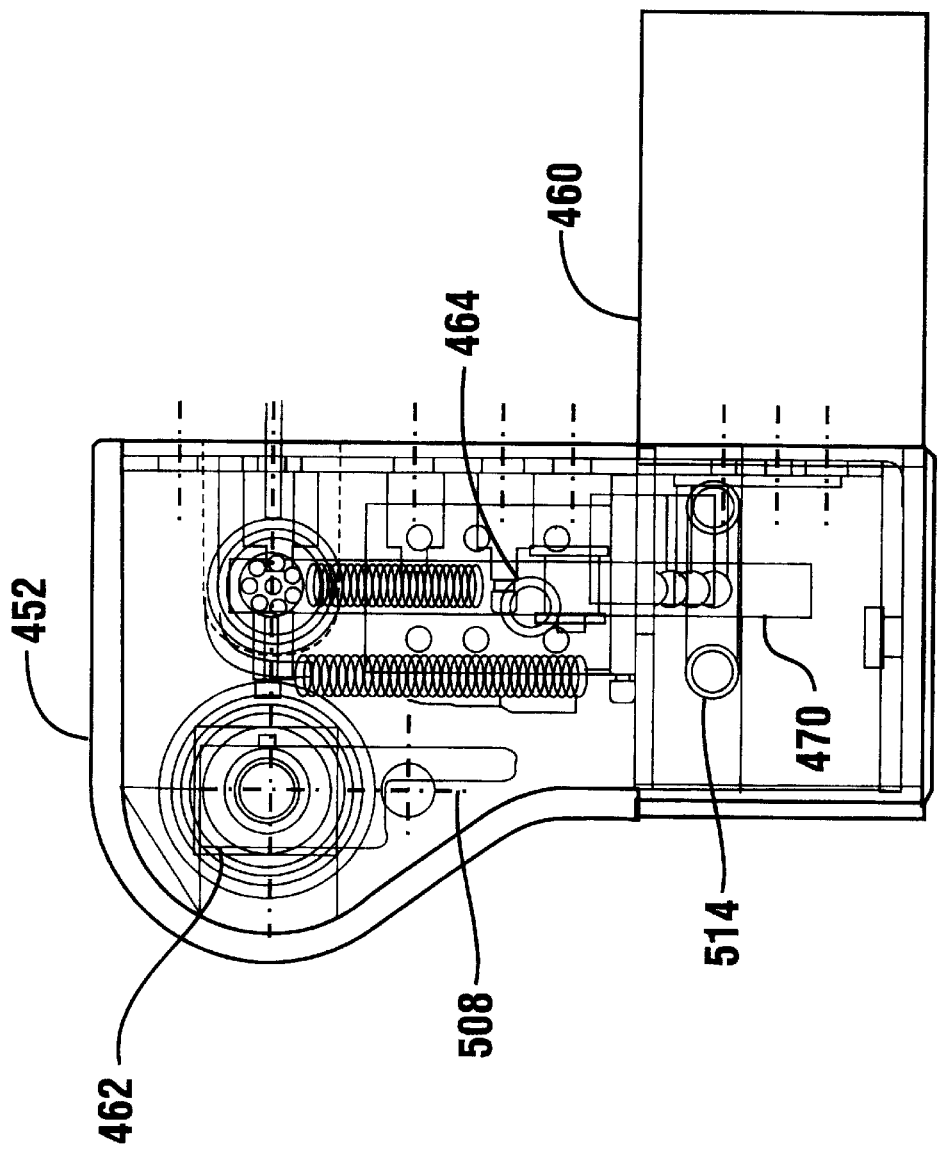
FIG. 51 is a front view of the lock module and bolt supporting bracket shown in FIG. 50.

The refrigerator 450 and lock module 452 of one preferred embodiment of the invention are shown in greater detail in FIGS. 50–54. As shown in FIG. 50 refrigerator 450 has a door 454. Door 454 is a conventional refrigerator type door that includes a handle 456 on an exterior area thereof. Refrigerator 450 also has a body 458. Body 458 has an interior area or compartment which is maintained at a temperature below ambient temperature suitable for the type of medical items intended to be housed therein. It should be understood that the interior area of the refrigerator 450 in some embodiments may be a single storage location in which one or more types of medical items are housed. Alternatively the interior area may be divided into several storage locations. These storage locations may be open storage locations or may be subcompartments to which access is further controlled by electronic or other types of locking mechanisms. The preferred embodiment of the invention provides for records to be maintained in the data store associated with the computer concerning the type and number of medical items stored in each storage location.

Door 454 in the embodiment shown may be swung open in the conventional manner so that authorized users may gain access to the interior area of the refrigerator. Access to the interior area is controlled by signals which are sent to the lock module 452. The lock module is mounted on an exterior surface of the body 458 in the embodiment shown. A bolt support bracket 460 is mounted to an exterior surface of the door 454. As later discussed bolt support bracket 460 is in connection with a bolt. The bolt is normally accepted and held by the lock module 452 so as to maintain the door 454 in a closed condition. The lock module 452 is operative to release the bolt in response to an appropriate signal so that an authorized user is enabled to access the interior area of the refrigerator.

The lock module 452 includes a key cylinder 462. Key cylinder 462 is part of a manual unlocking mechanism that enables opening the refrigerator door 454 using a key. This provides an alternative way for an authorized user to access the interior area of the refrigerator in the event of a failure which prevents the interior area from being accessed electronically or alternatively for emergency or restocking purposes. The lock module 452 also includes a visual indicator 464. The visual indicator 464 in the preferred embodiment is an LED type indicator which indicates that the lock module 452 has received the signal which enables the door 454 to be opened. In alternative embodiments other types of indicators or additional indicators may be used.

Figure 52:
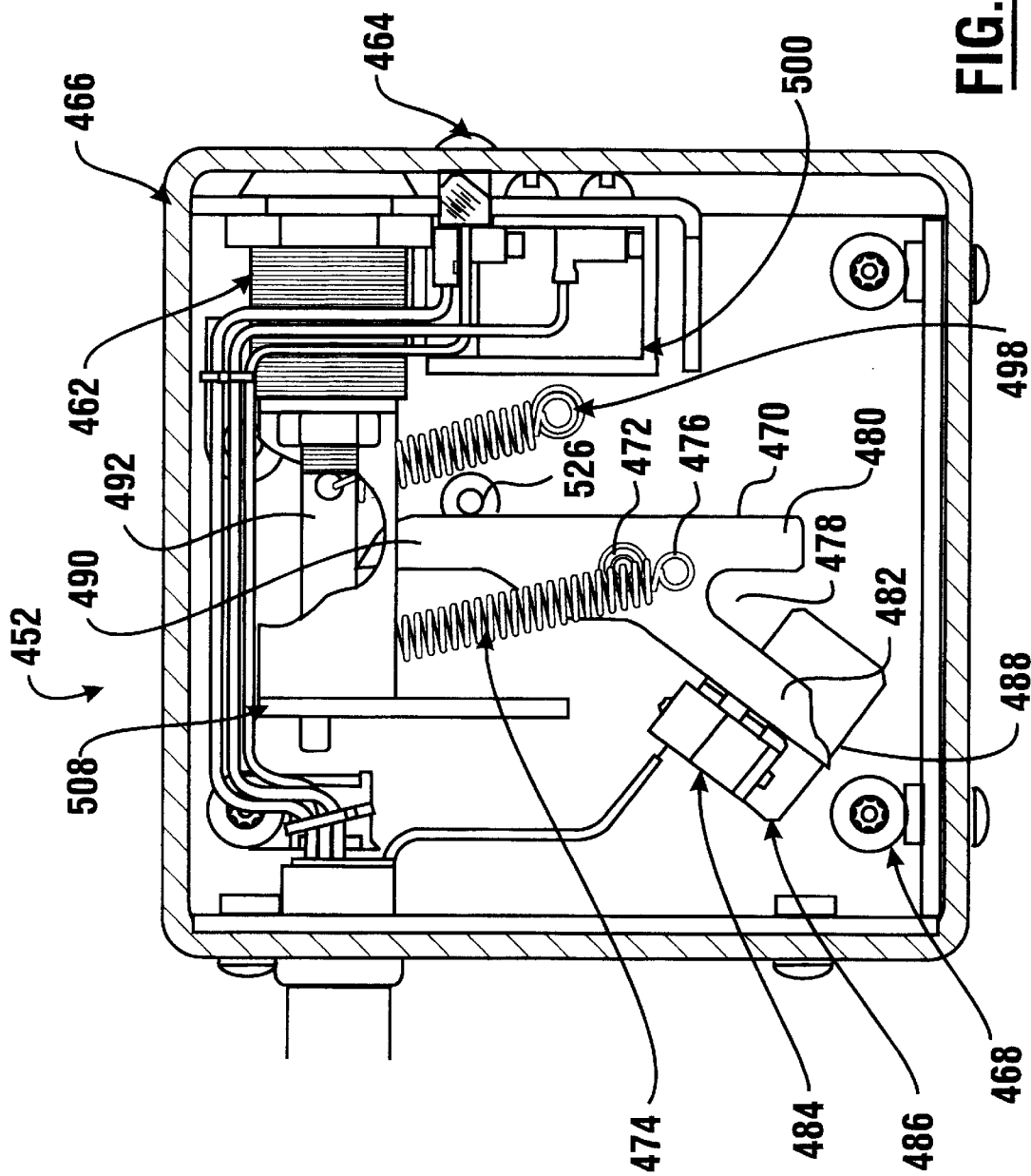
FIG. 52 is a partially sectioned view of the lock module.

As shown in FIG. 52 the lock module 452 includes an enclosure 466. The enclosure is secured to the exterior surface of the body 458 of the refrigerator by a plurality of fasteners 468. In the preferred form of the invention the enclosure 466 includes an exterior cover which restricts access to the fasteners after the enclosure 466 has been installed on the refrigerator. The preferred form of the invention is retrofit to an existing refrigerator or similar device by attaching the lock module 452 onto the exterior of the device and adjacent to the door thereof. Once installed using the fasteners 468 a cover is installed on the enclosure so as to minimize the risk of tampering.

As shown in FIG. 52 the lock module of the preferred embodiment includes a pawl 470. The pawl is mounted in rotatable relation about a pivot 472. A spring 474 is attached to the pawl by a pin 476. The pin and said spring are positioned relative to the pivot 472 so that the pawl 470 moves through an over center position during its operation. This enables the spring 474 to apply a force which biases the pawl to rotate about the pivot either in a first rotational direction or in an opposed rotational direction depending on the side of the pivot 472 on which the pin 476 is currently positioned.

The pawl 470 includes a recess 478 which receives a portion of the bolt therein in a manner later discussed. The recess 478 extends between a first leg 480 and a second leg 482 of the pawl 470. A sensor 484 is positioned to sense the position of second leg 482. Sensor 484 may be an optical or a magnetic type sensor that operates to sense leg 482 adjacent thereto. Sensor 484 is mounted on a bracket 486. Second leg 482 includes a tapered surface 488 the purpose of which is later discussed.

Figure 54:
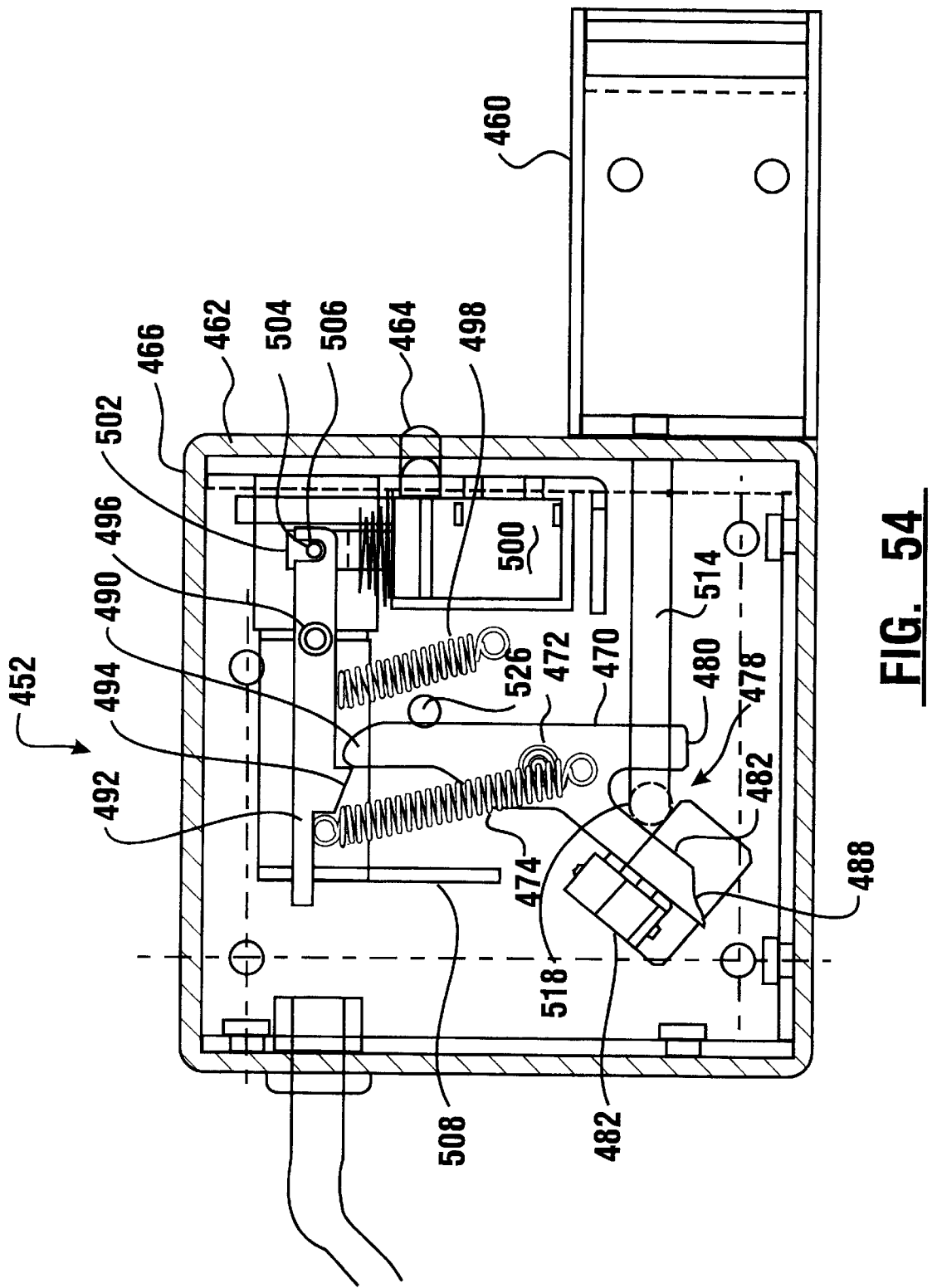
FIG. 54 is a sectional side view of the lock module and bolt supporting bracket with the bolt shown in engaged relation with the lock module.

As best shown in FIG. 54 pawl 470 includes a third leg 490. Leg 490 is bounded by a tapered surface as shown. A lever 492 includes a tapered step 494. Tapered step 494 is engageable with third leg 490 of the pawl 470 as shown. The tapered step 494 is part of a releasable catch for holding and releasing the lever and the pawl.

Lever 492 is rotationally mounted about a pivot 496. Lever 492 is biased to rotate about pivot 496 in a counter-clockwise direction as shown in FIG. 54 by a spring 498. A solenoid 500 is mounted in enclosure 466. Solenoid 500 includes an actuator rod 502 which is biased upwards as shown in FIG. 54 by a spring.

Actuator rod 502 is in connection with a pin 504. Pin 504 is engageable in a recess 506 in level 492. It will be appreciated that movement of the actuator rod 502 in a downward direction as shown in FIG. 54 rotates lever 492 in a clockwise direction. When the solenoid 500 deactivates, the actuator rod 502 rises and the lever 492 returns to the position shown in FIG. 54 due to the biasing force of spring 498. The arrangement of the pin 504 and the recess 506 enable the lever 492 to be movable other than by solenoid 500. As shown in FIG. 54 cylinder 462 has a projection 508 attached thereto. Projection 508 is rotatable when a proper key is inserted in the lock cylinder. Rotation of projection 508 enables the projection to engage lever 492 at the opposite end of the lever from recess 506. Moving lever 492 upward with projection 508 from the position shown in FIG. 54, moves the lever in a manner comparable to solenoid 500. This enables the lock module 452 to be changed from a locked condition to an unlocked condition in response to either a signal to the solenoid 500 or alternatively by a proper key inserted into cylinder 462.

Figure 53:
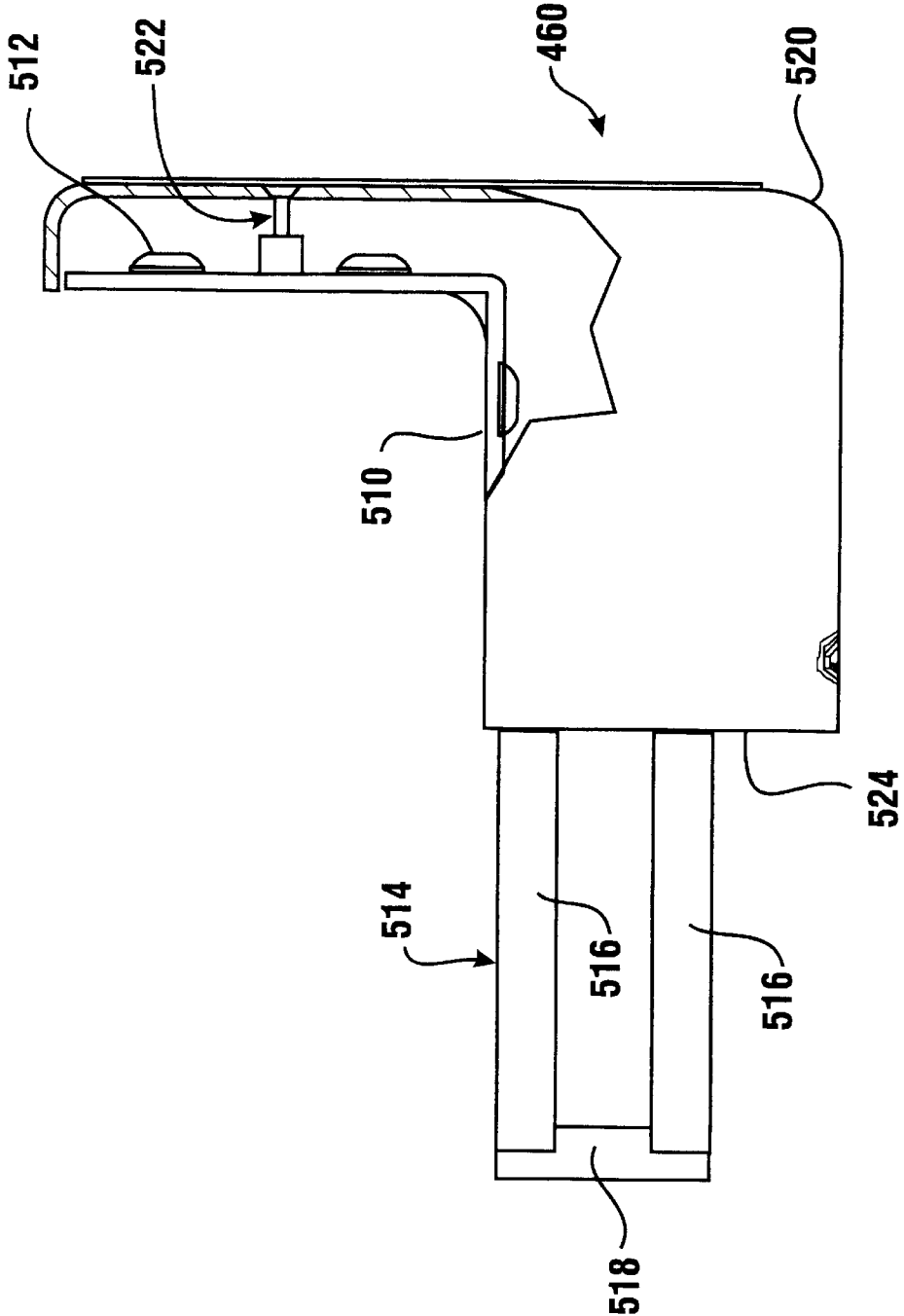
FIG. 53 is a partially sectioned top view of the bolt supporting bracket.

As shown in FIG. 53 bolt support bracket 460 includes an interior bracket portion 510. Interior bracket portion 510 is attached to an exterior surface of door 454 of refrigerator 450. The interior bracket 510 is attached to the door by fasteners 512 only the heads of which are shown. In the preferred form of the invention the interior bracket portion 510 extends adjacent and is attached by fasteners to both the front and side surfaces of the refrigerator door. Interior bracket portion 510 is attached to a bolt 514. Bolt 514 includes a pair of spaced legs 516 and a transverse rod 518 which extends between the legs.

A cover 520 is mounted in overlying relation to the fasteners 512 so as to restrict access thereto. Cover 520 is engaged to the underlying interior bracket portion 510 by fasteners 522 only one of which is shown. As best shown in FIG. 50 the cover 520 and the bracket 510 are constructed so that when the door 454 of the refrigerator 450 is closed, a surface 524 of the bolt support bracket is in close abutting relation with the lock module 452. This restricts access to the bolt 514 and minimizes the risk of tampering therewith.

As shown in FIG. 54 when the refrigerator door is closed the bolt 514 extends in the interior area of the enclosure 466 of the lock module 452. In the locked position the rod 518 of the bolt 514 is positioned in the recess 478 between the legs of the pawl 470. In this locked position the third leg 490 of the pawl is prevented from moving in a counterclockwise direction by engagement with the tapered step 494 on the lever 492. Likewise the pawl 470 is prevented in this position from moving in a clockwise direction by engagement with a pin 526 and the sensor 484 and its supporting bracket. This prevents the refrigerator door 454 from being opened.

When it is appropriate to open the door of the refrigerator a signal from the display terminal 98, or other operatively connected computer or device in the system, is transmitted to solenoid 500. The signal causes actuator rod 502 to move downward. This pivots level 492 in a clockwise direction about pivot 496. The movement of lever 492 disengages the catch holding third leg 490 of the pawl 470 engaged with the tapered step 494. The bolt 514 is enabled to rotate pawl 470 in a counterclockwise direction about pivot 472. As spring 474 moves into an over center relation, leg 482 pushes on the bolt to bias the door toward the open position.

The signal which activates the solenoid 500 also preferably causes illumination of the LED 464 so that a user is aware that the refrigerator door may be opened. In the preferred embodiment the signal from the display terminal lasts sufficiently long so that the user is enabled to open the door. Once the door has been opened the signal may be discontinued. This is preferably done in response to the sensor 42 sensing that the leg 482 of pawl 470 has moved away from the sensor. Alternatively the signal enabling opening of the refrigerator may time out after a period set in the computer, such as 30 seconds, in which case the solenoid ceases to retract rod 502 and the lever 492 returns to the position shown in FIG. 54.

In the preferred embodiment, whenever refrigerator door 454 is opened a record concerning the event is made by the computer 84 and stored in the data store 85. The record concerning the opening is preferably stored in correlated relation with data representative of a user who caused the door to be opened. Other data correlated with the event preferably includes all of the data associated with other types of dispensers in the system. This may include for example, the particular medications to be taken from the interior area of the refrigerator, a particular identified patient for whom the medications are to be taken as well as pricing and other information. Records concerning the numbers of medical items stored in the storage locations within the interior area of the refrigerator are similarly stored in the data store and adjusted based on the data input to the display terminal.

In the preferred form of the invention the refrigerator door may remain open despite the signal to the solenoid 500 being discontinued. In this condition the lock module 452 is in position ready to lock despite the door being open. When the signal to the lock module is discontinued the lever 492 returns to the position shown in FIG. 54. In this condition the pawl 470 is rotated counterclockwise from the position shown in FIG. 54. As the door of the refrigerator is closed the bolt 514 moves into the interior area of the enclosure 466. The rod 518 at the end of the bolt engages the tapered surface 488 on second leg 482 of the pawl and begins to rotate the pawl 470 in a clockwise direction about pivot 472.

Pawl 470 moves in a clockwise direction against the force of spring 474. The tapered surface of the third leg 490 engages and moves on the tapered step 494 of the lever 492 so as to move lever 492 clockwise against the force of spring 498. Eventually as the bolt 514 moves inward the rod 518 of the bolt moves into the recess 478 of the pawl. Thereafter continued movement of the pawl 470 in the clockwise direction causes the third leg 490 to move past the tapered step 494 on the lever 492. This causes the lever 492 to move downward again holding the pawl in fixed engaged relation therewith.

As the refrigerator door is closed the leg 482 of the pawl again moves adjacent to sensor 482. This provides a signal which is received at the display terminal 98. This signal indicates that the door has been closed. In a preferred embodiment of the invention the time of closing of the refrigerator door is preferably included as part of the dispensing event information in the data store along with the other associated information concerning the event. In alternative embodiments of the invention the timing routine may be provided either in the display terminal 98 or in the computer 84 so as to provide an indication when the door of the refrigerator remains open beyond a set time period. Such a condition may be indicative of a problem or tampering with the unit. Such an indication may be given either at the display terminal and/or at other connected terminals in the system. In other embodiments of the invention other approaches and techniques related to the tracking of items dispensed from the refrigerators and other controlled environmental chambers within the system may be used.

Another type of dispenser apparatus that may be used in the system of the present invention is the medicine dispenser 100 shown in FIG. 13. Medicine dispenser 100 is also used for dispensing medical items that require high security such as narcotics. However, unlike electronic lock drawer 96, medicine dispenser 100 is operable to dispense only the particular item requested and to restrict access to all the other items housed within the medicine dispenser. As shown in FIG. 13 the medicine dispenser is connected to a data terminal 102 that is similar to data terminals 76 and 98. The operation of the data terminal 102 in conjunction with the medicine dispenser 100 is similar to the operation of data terminal 98 in cooperation with electronic lock drawer 96. The difference in the use of the medicine dispenser is that in response to selection of the particular medical item (and the co-user verification if required) the medicine dispenser will provide to the user the particular medical item requested in the quantity requested. As a result, the user is not required to locate the item as is required with the electronic lock drawer. In addition, the level of security required for dispense of medical items within the medicine dispenser can be varied depending on the level of security required for the particular item. As a result, for some items in the medicine dispenser 100 it may be necessary only to verify that the user is an authorized user. For other substances, only selected authorized users (and co-users) will be given the substance.

The user interface of the display terminals of an embodiment of the present invention are shown in FIGS. 28 through 39. When the user accesses the system using the display terminal the user usually begins with the user log-in screen 302 shown in FIG. 38. In the user log-in screen the user may input a user identification code using the "buttons" on the touch screen. The user may alternatively run their badge or other identification card through the card reader. After input of the user identification code the user inputs their PIN. After a user successfully accesses the system through the display terminal for purposes of obtaining medical items for a patient, they are generally presented with the patient browser window shown in FIG. 28. From the patient browser window 222 a user may manipulate the previous page and next-page buttons 224 and 226 respectively to display the patient for whom the medical items are to be taken on the screen. The programming of the display terminal includes a highlighting feature which serves as part of an input device of the display terminal.

A patient is selected by a user's finger being brought adjacent to the touch screen which operates the display terminal to highlight the patient name as graphically indicated by the highlighted band with a patient name in FIG. 28. Upon touching the patient name in addition to being highlighted, the patient name is also shown at the top of the screen. This serves to identify this particular patient to the system as the one for which medical items are being taken.

From the patient browser screen 222 a user is enabled to remove items from the hook or box registers, in which case the items will be automatically indicated as taken for and charged to the patient. Similarly if an item taken for a patient is to be returned to a hook or box register, highlighting the patient name on the patient browser screen and replacing the item on the hook or box register results in the patient's records and account being credited for the returned item.

From the patient browser screen 222, more information concerning the selected patient may be obtained by the user touching a patient info button 234. Touching the patient info button 234 causes the display terminal to display the patient information window 236 shown in FIG. 29. Patient information window 236 shows information about the patient. This can include vital statistics, the name of the treating physician, allergies that the patient may have and other information. In addition, the patient information window 236 also shows the assigned location of the patient in the facility. The patient information window 236 includes a close button 238 which a user presses to return to the patient browser window 222.

It should be noted that the patient browser window 222 as well as the patient information window 236 include a help button 240. The help button 240 is pressed by a user when they wish to obtain more information about using the system features that are currently accessed on the displayed window. The display terminal and the connected computer systems are programmed appropriately to provide instructions concerning the type of help most commonly needed when accessing the particular patient windows. This makes the system easier to use and reduces the amount of training required before user may effectively operate the system.

From the patient browser window a user may choose to review the medical items that have been taken for the selected patient. To do this a user touches a patient usage button 242. In response to selection of the patient usage button, the computer and display terminal are operative to display a patient usage browser window 244 shown in FIG. 30. The patient usage browser window is operative to show medications and other medical items that have been taken for the patient as well as the amount and time that each medical item was taken. The patient usage browser window also includes a return button 246 and a waste button 248. The return button is selected in situations where a medication that has previously been taken for a patient is returned without being administered. The return button is used in situations where the returned item is a controlled substance such as a narcotic or is another item that cannot be freely dispensed or used for another patient. Selecting the return button generally enables a particular return drawer mechanism to open into which the medical item may be returned. By highlighting a particular dose of medication on the patient usage browser screen and completing a return transaction, the status of a medication may be changed from taken to return.

The waste button is used in situations where an item taken for a patient is to be returned in whole or in part and it cannot be used for another patient. This includes situations where only a portion of the medication is delivered and the balance is waste. Selecting the waste button 248 also preferably opens a return drawer into which the wasted item may be deposited. The patient's records are simultaneously adjusted accordingly in the patient records and on the patient usage browser window.

The operation of the return and waste buttons 246 and 248, respectively, along with a return drawer used in the preferred embodiment is shown in copending U.S. application Ser. No. 08/679,203 filed Jul. 12, 1996, the disclosure of which Application is incorporated herein by reference.

The patient usage browser window 244 also includes a discrepancy button 250. The discrepancy button is used in connection with dispensing medications as well as with the return and wasting of medications. The discrepancy button 250 is used by a user to indicate to the system that something requested was not provided, or that an indication previously input to the system is not accurate. Pressing the discrepancy button causes the display terminal to display a window appropriate to indicate the nature of the discrepancy. The patient usage browser window 244 also includes a previous page button 224 and a next-page button 226 similar to those previously described for scrolling through the information pertaining to the patient. Window 244 also includes a help button 240 and a close button 238 like those previously described. The close button is used when the user is finished with the patient usage browser window and wishes to return to the patient browser window 222.

Patient usage browser window 244 further includes a trade name/brand name button 252. Button 252 is operative to change the names of the medical items displayed on window 244 from the trade name to the brand name and vice versa. Button 252 may be toggled from one name for an item to the other. This feature is available in a number of windows and is useful for a user who may need to compare the brand name(s) of a medical item to the generic name and vice versa.

Trade name/brand name button 252 is enabled to provide this feature at the display terminals responsive to records stored in data store 85 in which the generic names and brand names for medical items in the system are stored in correlated relationship. The data store 85 further includes in its records data indicative of whether each particular name for the medical item is the generic or brand name. Multiple brand names corresponding to generic names may be stored and displayed on the screen. This feature enables a user operating the display terminal to toggle the display back and forth between brand name and generic name. In addition, the display terminal indicates in a header above the drug information whether the generic or brand name information is being provided on the screen. Button 252 changes to the opposite designation to that being displayed when it is toggled. This informs a user that they can change from, for example, the generic name shown in window 244 to the trade name or brand name by touching button 252 on the touch screen.

From the patient browser window 244, a user is enabled to review medications available for dispense to a patient. To review the medications that have been prescribed for a particular patient, a user highlights the desired patient name by touching the name in the patient browser window 222 and touches a med order button 254. Touching med order button 254 causes a med order browser window 256 shown in FIG. 31 to be displayed. Med order browser window 256 includes information about the medical items that have been prescribed for the patient including information such as dosage and frequency of administration. The med order browser window also contains other information such as the route by which the medication is to be delivered to the patient such as orally or through intramuscular injection. The med order browser window 256 also includes the date and time information that the medication was started. If a medication has been stopped, this may also be indicated.

If a user wishes to take a medication for a patient, the user may highlight the medication on the med order browser window and touch a dispense button 258. By touching the dispense button on the touch screen, the display terminal is operative to cause the electronic lock drawer, medication dispenser or other apparatus in which the particular medication is held to operate to make the medication available to the user. The med order browser window 256 further includes an info button 260. Info button 260 may be pressed to display additional information about the particular medication which has been highlighted. This may include particular information that the physician wished to include concerning the administration of the medication. Alternatively the information button may access information stored in the data store 85 concerning the particular medication itself including information such as possible side effects, drug interaction data and the like.

The med order browser window 256 further includes a trade name/brand name button 252 which may be used to change the displayed drug identification information from generic to brand name and vice versa. Window 256 also includes a help button 240, a previous-page button 224 and a next-page button 226, all of which function in the manner previously described. The med order browser window 256 further includes a close button 238 which a user may select to return to the patient browser window 222.

Instead of reviewing medications that have been specifically prescribed for a patient, a user from the patient browser window 222 may choose to dispense medications and medical items from a listing of all medical items which are available in the area adjacent the display terminal. To accomplish this a user selects a supply button 262 on the patient browser window. Selecting the supply button 262 causes a supply browser window 264 to open on the screen of the display terminal. The supply browser window is shown in FIG. 32. Supply browser window 264 includes a listing of medical items which are available for dispense. A user may select one of these substances by touching the screen adjacent to the item desired. If it is a controlled substance such as a narcotic, the display terminal and associated computers are programmed to require heightened security such as two authorized users to log on to the display terminal before a dispense may be made as was previously discussed.

A user dispenses medical items from the supply browser window 264 by highlighting the item desired and selecting the appropriate select quantity button 268. The select quantity button indicates how many of one particular medical item the user desires to have dispensed. The user then selects the dispensing button 258, which is operative to cause the display terminal to actuate the appropriate device for dispensing the requested quantity of the item.

Figure 36:
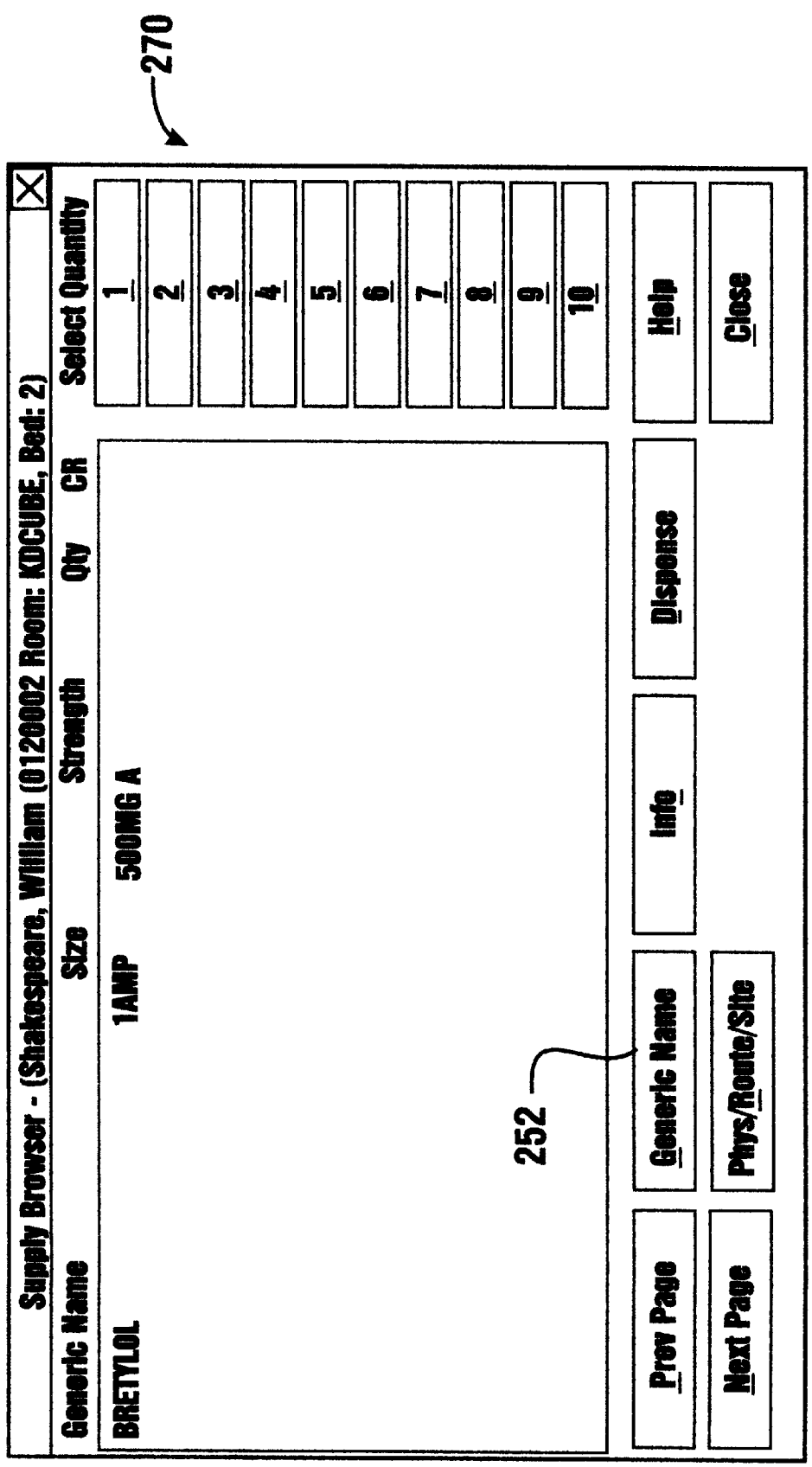

The supply browser window 264 also includes the trade name/brand name toggle button 252 previously discussed. The operation of button 252 is demonstrated with regard to an alternative supply browser screen 270 which is shown in FIGS. 35 and 36. Alternative supply browser screen shows only one medical item so as to make more apparent the operation of button 252. In FIG. 35 button 252 is set to display the generic name of the medical item, in which case the single medication shown is displayed by its generic name and button 252 indicates that it is available to be toggled to the trade name. Toggling button 252 changes browser screen 270 to the format shown in FIG. 36 in which the trade or brand name of the medication is displayed, and button 252 indicates that it is available to be toggled to display the generic name. Of course, for medical items for which there is only a generic name, the data base records stored in the data store 85 in connection with computer 84 or other connected computer in the system may be arranged to indicate that there is no corresponding brand or generic name when this situation arises. Likewise for items which have multiple brand names, the display terminal is preferably operative to provide all the brand names associated with the item.

The data store of the system also includes pricing information for both brand and generic medical items. The data terminal and connected computers are operative to charge the patient's account for the type of item which is dispensed. This is determined responsive to the name for the item displayed on the display terminal when the dispense is made.

In some situations the name type for an item prescribed for a patient may not be available in the dispensers connected to the display terminal or otherwise available in the area adjacent the display terminal. The display terminal or connected computer may be programmed responsive to a request to dispense an item by a trade or generic name which is not available, to indicate on the display terminal that the item is available under an alternative name. The user in response to receiving such an indication, may toggle button 252 and dispense the item under its alternative name. In such situations, the user may also consider this a discrepancy which should be recorded in response to the user prompts generated in response to selecting the discrepancy button 250. The ability of the system to track items by both trade or brand names and generic names may avoid needless delay in providing medical items.

Figure 37:
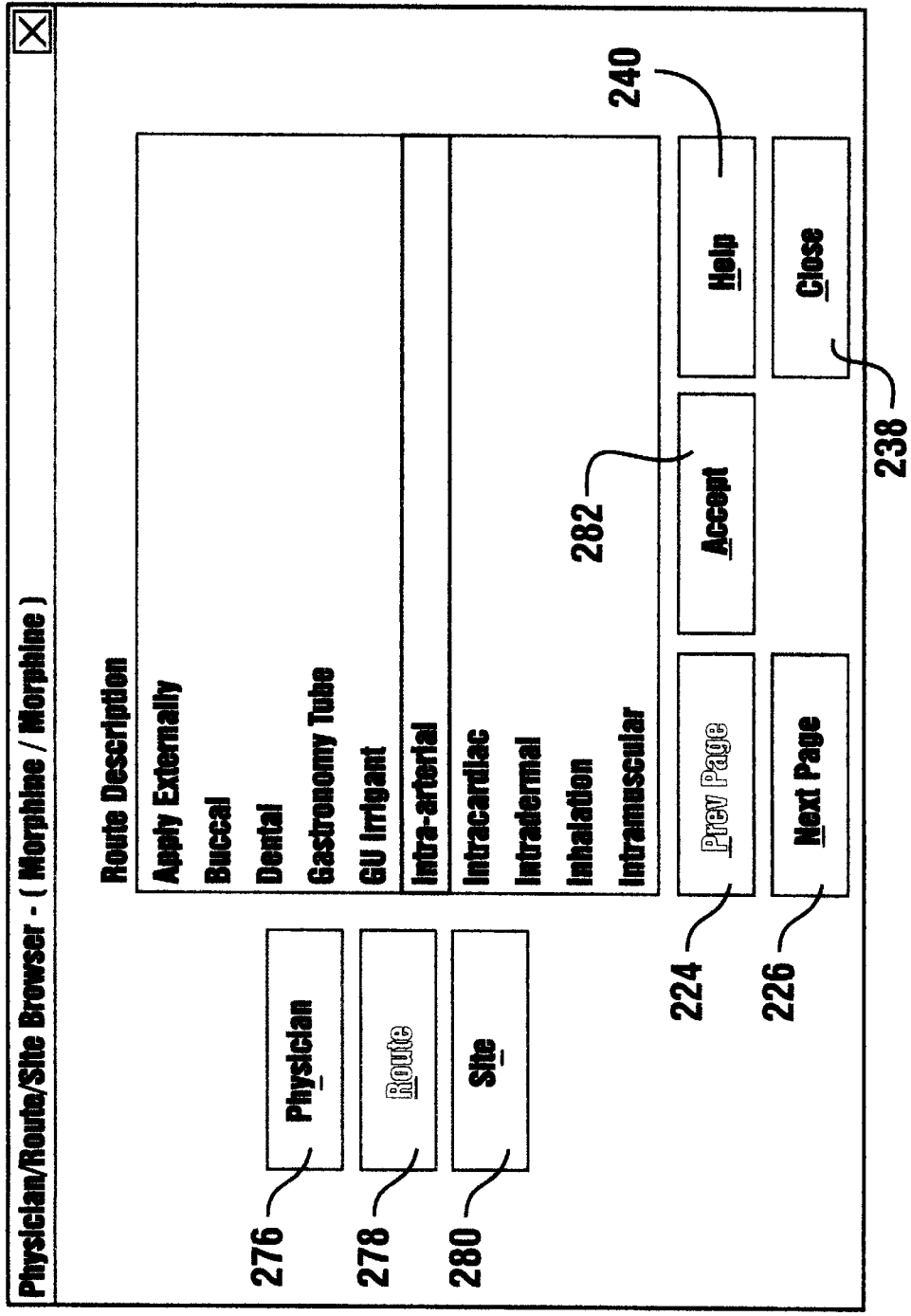

The supply browser window 264 also includes a physician/route/site button 272. Selecting button 272 causes a physician/route/site browser window 274 to be displayed. A sample physician/route/site browser window is shown in FIG. 37. If there is already a physician associated with the dispense of the medication selected in window 264 to the particular patient shown in that window, then a physician button 276 will be highlighted in window 274. If the physician button 276 is highlighted, then a user may press a route button 278 which will cause the display terminal to display a further window which indicates the route that the physician has prescribed for the medication to be administered to the patient. A site button 280 may be selected to review the site on the patient that the physician has prescribed for the medication to be administered. If, however, when the user accesses window 274, the physician, route or site buttons are not highlighted, no associations related to these parameters have been made.

To associate a dispensing order with a physician, a user may select the physician button 276 to display a list of physicians on the screen. The user may then select a physician which causes physician's name to be highlighted. The user may thereafter select the route button 278 which causes a listing of route information, as shown in FIG. 37, to be displayed. The user may then select a particular route by highlighting it. Thereafter, if appropriate, the user may select site button 280, which causes a list of sites to appear. The user may select a site. To save all the associated information that has been input, the user highlights an accept button 282. After reviewing the information in window 274 or establishing a new relationship, a user may close window 274 by selecting close button 238 and returning to patient browser window 222.

As previously discussed, a further advantage of a preferred embodiment of the present invention is that medical items to be used for a particular medical procedure are stored in correlated relation along with a designation of the particular medical procedure in the data store. These collections of medical items are called "kits" in the preferred embodiment of the invention. Kits may be established by the operator of the system in accordance with the particular needs of the system. Kits may include particular collections of medical items for a particular procedure that is scheduled for a patient. Alternatively and in addition, kits may also be a collection of medical items used to conduct particular types of frequently-administered medical tests, such as diagnostic tests.

In accordance with a preferred embodiment to the invention, from the patient browser window 222 a user may review kit information by selecting a kit button 284. Selecting the kit button causes a kit browser window 286 shown in FIG. 33 to be displayed on the display terminal. The kit browser window shows kits that have been prescribed for the selected patient. In addition, the kit browser window preferably displays a listing of other available kits. A user may select a particular kit by touching the kit on the touch screen. If the user wishes to learn what items are in the highlighted kit, they may select a kit info button 287. Selecting the kit info button causes the display terminal to display a kit information window 290 shown in FIG. 34. Kit information window 290 shows the name of the kit and all of the items that are included in the kit. In addition the kit information window shows how many of the particular items in the kit are available for dispense from the storage locations adjacent or attached to the display terminal. The computer may alternatively be programmed either in the kit information window 290 or when a kit is dispensed, to indicate to a user where items that are not available in the area adjacent the display terminal may be obtained. The inventory tracking features of the invention enable providing the user with the nearest location the needed item is stocked.

After reviewing the information concerning what is in the kit, the user may select a close button 238 on kit information window 290 to return to the kit supply browser window 286. The user may select the dispense button 258 in window 286. Selecting the dispense button is operative to cause the display terminal to dispense or make available all the items in the kit together. In addition, the display terminal and connected computers may be programmed to indicate in response to selection of the dispense button that the user is required to manually take from open storage certain medical items that may be required for the kit which are not dispensed. This is accomplished through appropriate programming of the records in the data store when the kit is established. Of course, selecting the dispense button 258 not only causes all of the items in the kit to be dispensed or otherwise made available, but such items are also charged to the patient's account.

The storage of information in the data store concerning kits, which is data representative of collections of items stored in correlated relation for a particular procedure or activity, is highly useful. It provides for automatically dispensing the needed items together where possible, and provides a visual reminder to the user of the system of all the things that are needed to accomplish a particular medical procedure. This avoids mistakes and saves time. Of course, after reviewing the kit browser window 246 and/or dispensing a kit, a user may return to the patient browser window 222 by selecting the close button 238.

After a user has completed dispensing transactions for a particular patient, they may take medications for another patient by highlighting that patient on the patient browser window 222 and repeating the steps for that patient in accordance with the procedures previously discussed. The system is programmed so that a user is free to obtain items either from dispensers of various types in response to dispensing requests, to manually remove items from hook or box register locations or to take items from accessible storage locations. For those items which are controlled substances such as narcotics, dispensing transactions cannot be completed until a second appropriate user or witness enters their identifying information to the system to witness the dispensing transaction. As previously discussed, dispensing transactions which are conducted by a user or a witness are recorded by storing the information on what was dispensed in correlated relation with the user's record as well as with the patient's record in the data store. Of course, the system may be programmed to correlate and store other types of information as well.

When a user is finished with dispensing medications for patients, they may select the log-out button 232 at which point the display terminal waits to be accessed by another authorized user.

It should be noted that the patient browser window 222 also includes a restock button 292 and a retrieve button 294. The restock button 292 is used in connection with restocking the system. Certain system users have correlated records in the data store that enable them to restock the system. Such a user, when they access the data terminal may also select the restock button 292 and cause the display terminal to display windows upon which a user may indicate which items have been restocked, and the available quantities. The person restocking preferably does this by accessing the dispensers and electronic lock drawers using keys or access methods which are not controlled through the display terminal. However, in other embodiments the display terminal may be used for opening the dispensers and electronic lock drawers for restocking purposes as well. Once the user restocking the items has completed the information associated with the restocking activity, they can log out of the display terminal by selecting button 232.

Retrieve button 294 is likewise used by a selected group of authorized users. The retrieve button is used to enable certain selected users who have authority to access medications that have been returned or wasted and which are stored in a particular retrieve drawer. Such an authorized user has an associated record in the data store that authorizes them to do this and when such a user authorizes the system and selects this button, the retrieve drawers may be opened. To enable the user to retrieve such items, the process of retrieving returned or wasted medications is described in copending U.S. application Ser. No. 08/679,203 filed Jul. 12, 1996, the disclosure of which is incorporated herein by reference. Again, after a user has conducted a retrieve activity, they may exit from the system by selecting the log-out button 232.

Embodiments of the invention may also be used in connection with medical items which are "non-itemized". Such items are generally not counted and not tracked to patients so there is no record maintained in the data store that such an item was taken for a particular patient. Likewise, in most cases the item is not billed to the patient. However, in some cases items may be tracked to a patient but not billed. Generally non-itemized items are stored in open storage locations. Any authorized person is free to take these items for patients or for a medical condition that the user may be experiencing.

It is important however that supplies of non-itemized or otherwise uncounted medical items be maintained at adequate levels. Because the system does not track the taking of such items it is possible for such items to fall below desired levels or to be completely depleted before an appropriate person is notified to replenish the quantity of medical items in the non-itemized storage location. Significant time periods may elapse before the supply is replenished.

An embodiment of the present invention operates to minimize the risk that non-itemized medical items will be depleted. This embodiment enables a user, upon noticing that the level of items in storage in a storage location has fallen below a desired level, to indicate to the system this condition. An appropriate function within the medical facility is notified and the storage location is restocked. To achieve these results storage locations for non-itemized medical items are physically marked to indicate a level at which restocking should be performed. Generally this may be accomplished by placing a physical marking in the storage location, such as a line on a shelf. As items are removed from the shelf for example from left to right, a user knows that when the number of items remaining is "below the line" there is a need to indicate this quantity condition to the system. This level in some instances may be referred to as a "minimum" acceptable level of supplies. Alternatively, the level may be referred to as a "par value" which means the average desirable quantity of medical items to have available. Where the levels are set and how they are characterized depends on the medical item and the needs of the users of the system.

Figure 38:
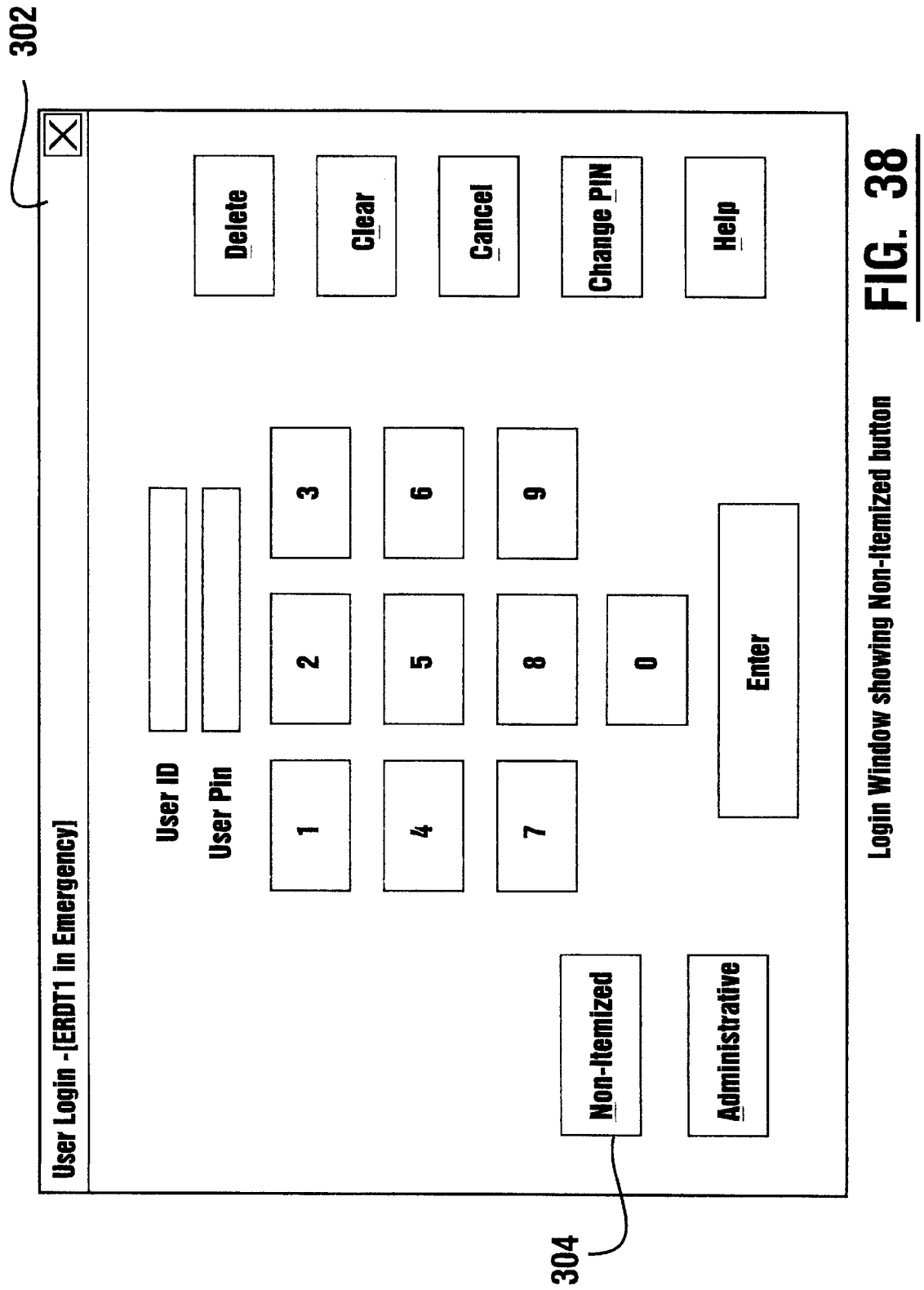

As shown in FIG. 38 a user approaching the display terminal is presented with the user log-in screen 302. In the embodiment of the invention shown the user may press the "non-itemized button" 304 without logging into the system. When the user presses the non-itemized button the non-itemized inventory window 306 shown in FIG. 39 is presented on the screen of the display terminal. Non-itemized inventory window 306 presents a listing of the non-itemized inventory items as well as their locations.

The user, after accessing the non-itemized inventory window, may highlight a particular supply by touching the touch screen in the area where the item is listed. The user may indicate the particular quantity condition that the user has noted for the supply. For example, if the supply is below the desired level the user may touch the "below minimum button" 308 on the touch screen. Pressing this button causes a signal to be generated and a message to be transmitted to the data store that the items in this particular storage location are below the minimum. The system is preferably programmed so that this information is also presented in the form of a message or report to the function or department in the medical facility responsible for restocking the storage location. In response a restocking of the particular storage location with the corresponding items is performed. Similarly if a user notes that a particular supply position is out of stock, the user may press the "out of stock button" 310 on the non-itemized inventory window 306. Pressing the out of stock button causes a different signal to be generated and transmitted to the data store, as well as to the restocking function. Preferably the system is programmed so that the restocking function is notified on a more urgent basis to replenish the items in the storage location than in the case of a below minimum situation. When the user is done using the non-itemized supply window they may return to the user log-in screen 302 by pressing the "close button" 312.

As shown in FIG. 39 the non-itemized inventory window 306 also includes a "trade/brand name button" 314 which may be used to change the supplies from brand to generic name and vice versa responsive to pressing the button. Likewise, a "position/name button" 316 is provided so that the window 306 can present the non-itemized medical items either in order by name or by supply position. This facilitates finding a desired item quickly.

The system of this embodiment is preferably operable to determine the locations where supplies need to be replenished and to provide the users who perform the restocking function with information on the types of medical items and the quantities which must be added to the storage locations. In the case of non-itemized inventory a restocking user who has replenished a storage location by adding a quantity of medical items thereto, may highlight the particular item and location and indicate that it has been restocked by pressing a "restock button" 318. Often the restocking function will replenish all of the storage locations. When this is done the restocking user may indicate that all the non-itemized locations have been restocked by pressing a "maximum all button" 320. The use of this feature saves considerable time for a restocker who would otherwise be required to highlight the various items either individually or in groups and change their status.

In an alternative embodiment to the invention, the actuation of the restocked button 318 and the maximum all button 320 may be limited to users who are authorized to carry out a restocking function as indicated by the data in the data store. In a system configured to be operated in this manner, a restocking user would be required to log onto the system using the user log-in screen 302, as must be done for inventory that is itemized and tracked to patients. Once the user with restock privileges has logged in, the appropriate buttons may be touched to indicate that the quantity conditions at the storage locations have been changed.

The operation of the described embodiment of the system for handling non-itemized medical items provides a significant time savings for system users. Handling items as non-itemized is particularly appropriate for common, low cost items which are often accessed and are not billed to patients. Implementing this approach avoids the need for users to go through additional and unneeded steps to take such items. Of course, if the institution operating the system decides that items in non-itemized inventory should be tracked to patients, counted or billed, such items may be reclassified in the data store. The result would be that such items would be removed from the non-itemized inventory listing and included in the listing in the supply browser window 264 and other appropriate windows which show medications which are tracked and billed.

Figure 40:
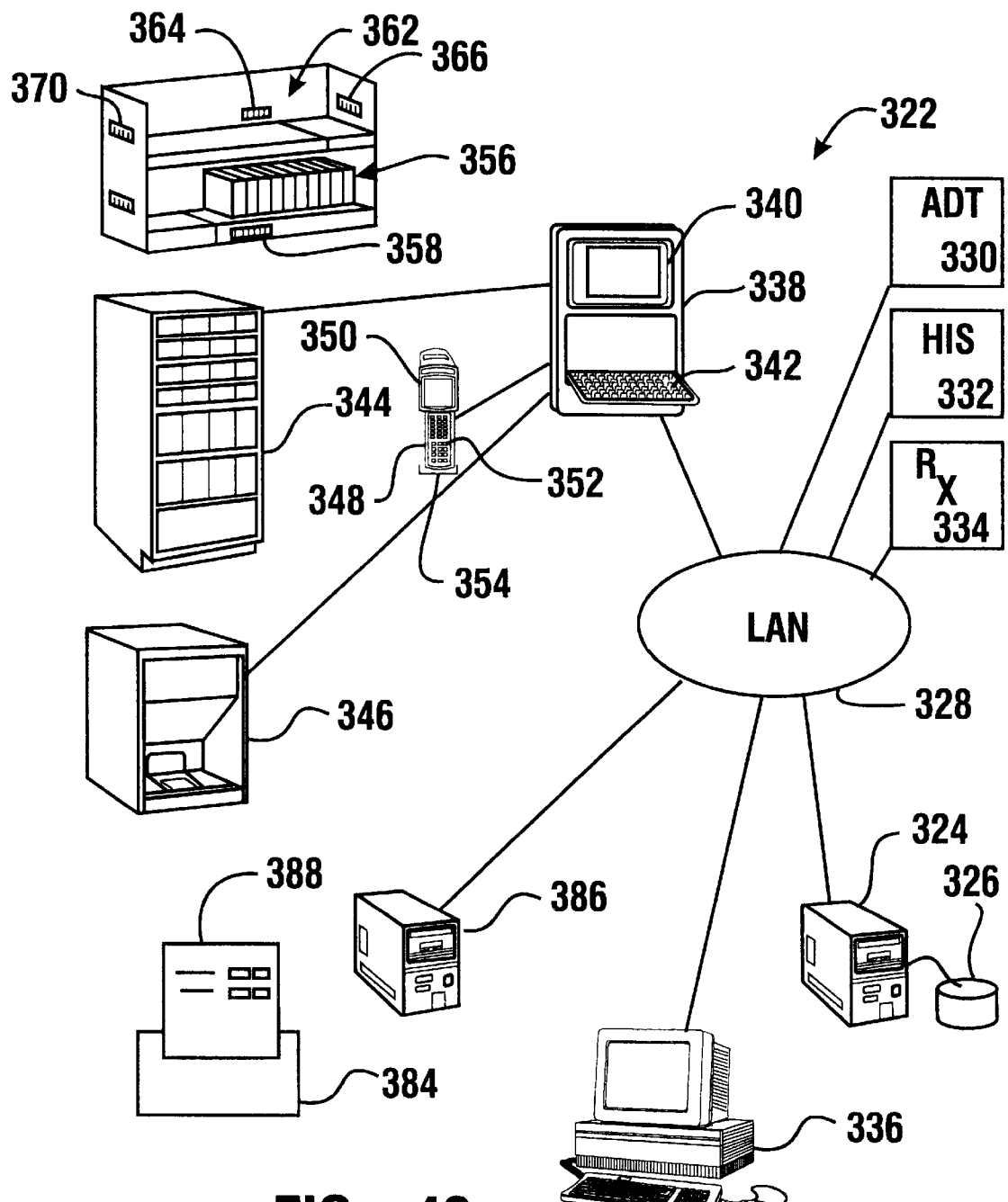
FIG. 40 is a schematic view of an alternative embodiment of the system for monitoring and dispensing medical items.

A further alternative embodiment of the system for tracking and dispensing medical items is shown in FIG. 40. This alternative system generally indicated 322 is similar in all respects to the system described with reference to FIG. 13, except as otherwise indicated. The system 322 includes a computer 324 which includes therein or is otherwise operatively connected to a data store, schematically indicated 326. It should be understood that computer 324 and data store 326 are shown schematically and that embodiments of the invention may consist of several operatively connected computers and data stores.

The computer 324 is connected through a network 328 to other devices and systems. Network 328 may be a local area network (LAN) within the facility, or wide area network. Network 328, as in the previously described embodiment, is connected to the facility's admission, discharge and transfer (ADT) system schematically indicated 330. Likewise, network 328 is connected to the facility's information system (HIS) 332 and the facility's pharmacy system 334. Preferably, as in the previously described embodiment, all of these systems within the facility are enabled to exchange information and function in cooperation with other devices connected through the network 328.

System 322 also includes one or more administrator's workstations 336. The administrator's workstations are similar to those in the previously described embodiment of the system. The system also includes a plurality of display terminals 338, only one of which is shown. Display terminal 338 is similar to the display terminals 98, 76 and 102 previously described, except as otherwise indicated. Display terminal 338 includes a touch screen 340 which serves as an input device and an output device. The display terminal also has a fold down, alphanumeric keyboard 342 which serves as an input device. Display terminal 338 also preferably includes a card reader, a processor, as well as its own local data store, and interfaces connecting the display terminal to both the network 328 and the other devices to which it is connected.

The display terminal 338 is in operative connection with storage devices for storing medical items. An electronic lock drawer 344 is connected to the display terminal 338. Electronic lock drawer 344 is similar to the electronic lock drawer previously described, except as otherwise indicated. The electronic lock drawer includes a plurality of storage locations for medical items and includes electrically actuated locks for selectively controlling access to the storage locations. The locks are opened in response to signals sent from the display terminal 338.

A refrigerator 527 is also connected to display terminal 338. Refrigerator 527 includes a lock module thereon and operates in a manner similar to the refrigerator 450 previously described. The refrigerator has an interior area which includes one or more storage locations for storing medical items therein. A lock module on the refrigerator selectively controls access to the interior area of the refrigerator in response to one or more signals sent from the display terminal 338.

A dispenser 346 is also connected to display terminal 338. Dispenser 346 holds a plurality of different types of medical items in storage locations therein, and selectively dispenses medical items from its storage location in response to signals from the display terminal 338. Dispenser 346 may be similar to dispenser 100 or preferably may be a dispenser of the type shown in co-pending U.S. application Ser. No. 60/045,137 filed Apr. 30, 1997, the disclosure of which is incorporated herein by reference.

The alternative system 322 further includes a reading device 348 in operative connection with the display terminal 338. The reading device 348 is preferably a device for reading machine readable indicia such as bar code. The reader device further preferably includes a display screen or other output device 350, as well as an input device 352 in the form of a keypad with alphanumeric designators and function buttons, through which a user may enter inputs.

The preferred form of the reading device 348 includes its own internal processor and memory. The memory includes programmed instructions referred to herein as configuration data, which controls the operation of the processor and the components which make up the reading device. The configuration data includes data which enables the reading device to recognize and interpret machine readable indicia. It also preferably includes information on authorized users of the system and their corresponding personal identification numbers (PIN). The configuration data preferably further includes information on storage locations and the location designators for locations associated with the display terminal 338, as well as the medical items stored in those locations. The configuration data also preferably enables the reading device to receive instructions and to generate transaction messages. The transaction messages are sent to the display terminal, and are then forwarded to the other components of the system. The reading device 348 also preferably includes a storage location or cradle schematically indicated 354. The cradle 354 provides a place for holding the reading device when it is not in use. In addition, placement of the reading device in the cradle may be used to initiate certain activities by the reading device as hereinafter explained.

This alternative form of the system of the invention is described in connection with FIG. 40. Storage locations are preferably labeled with machine readable indicia corresponding to the location designator established in the data store for the particular storage location. Such machine readable indicia identifies the location and also preferably the medical item type to be stored in the location. As will be appreciated from the description of the operation of the system which follows, including machine readable indicia representative of the medical item type enables the system to verify the data in its data store concerning the type medical item stored in a storage location. This feature may also avoid the need for the data store to include information on the medical item types stored in certain storage locations, because such information can be read directly. Alternatively, storage locations may be labeled only with indicia representative of the location or the medical item, and the data stored in the data store can be used by a processor to resolve the corresponding medical item or location.

A schematic view of an open storage shelf indicated 356 is shown in FIG. 40. Shelf 356 holds medical items thereon which may be removed by a user of the system. Shelf 356 includes machine readable indicia 358 thereon which identifies the particular storage location. The indicia may also include data representative of the medical item type stored therein.

Figure 41:
FIG. 41 is a label with machine readable indicia for identifying a storage location.

Preferably the machine readable indicia also includes human readable indicia to advise a user what is stored in the storage location. This is preferably done using a label, an example of which is indicated by label 360 shown in FIG. 41. Label 360 is an example of a position only label which includes machine readable indicia which indicates only the storage location and the medical item stored therein. Label 360 is an example of the type of machine readable indicia used on storage shelf 356 and indicated by machine readable indicia 358 thereon.

Further machine readable indicia are also applied to the storage locations in this alternative embodiment of the invention. Such further indicia is explained with reference to storage shelf 362 shown in FIG. 40. Storage shelf 362 includes machine readable indicia 364 which like indicia 358, identifies the storage location. It should be noted that indicia 364 is positioned so as to be accessible only when the medical items stored on shelf 362 have been reduced to a level such as the below par value or below minimum, where restocking is desirable. Of course storage shelf 362 may be marked in an appropriate manner as shown to indicate when the quantity of medical items stored thereon has fallen to a level where an input should be given to the system to replenish the location. Storage shelf 362 also includes further machine readable indicia 366. Further indicia 366 is preferably positioned to become accessible when the last of the medical items stored on the shelf is removed. In alternative embodiments further indicia 366 may be placed in other locations however.

Figure 42:
FIG. 42 is a label with machine readable indicia for indicating an out of stock condition at a storage location.

FIG. 42 shows a label 368 which is used to indicate an out of stock condition at a storage location. Label 368 corresponds to indicia 366 shown in FIG. 40 on storage shelf 362. Label 366 indicates the storage location as well as the item stored therein, as well as the quantity condition that the item is out of stock at that location.

Figure 43:
FIG. 43 is a label with machine readable indicia for indicating that a storage location has been restocked.

As further shown in FIG. 40, storage shelf 362 includes further machine readable indicia 370 thereon. Such machine readable indicia 370 is preferably used by a user restocking the shelf 362 to provide an input that the particular medical item type stored in the location has been restocked. FIG. 43 shows an example of a label with indicia which indicates that a particular storage location has been restocked with a medical item. Such labels are preferably positioned in locations which are inconspicuous, and which can be read with the reading device 348 when the storage location has been restocked.

It should be understood that storage shelves 356 and 362 are shown as shelves for storage of non-itemized inventory. Because non-itemized inventory items are not tracked to patients, there is a need in some embodiments of the invention to distinguish such inventory from other open shelf type inventory that may need to be tracked. It is therefore preferable to provide visually distinguishable characteristics for labels or other machine readable indicia used for non-itemized inventory to distinguish them from indicia used in connection with medical items which must be tracked. One manner of accomplishing this is to use different colored labels for itemized and non-itemized inventory.

Figure 44:
FIG. 44 is a label with machine readable indicia to indicate that the quantity of items in a storage location is below a desired level.

For itemized inventory for which each unit is counted and/or tracked, it is desirable to provide separate machine readable indicia which can be used to indicate that a particular storage location is exhibiting a quantity condition corresponding to a level requiring replenishment, but has not yet reached the level of being totally depleted. To accomplish this for itemized medical items, machine readable indicia which indicates the "below minimum" or "below par value" quantity condition are placed adjacent to the storage locations. An example of such a label used for accomplishing this function is indicated 374 in FIG. 44.

It should be understood that while the foregoing description discusses holding non-itemized inventory in open shelf locations, in other embodiments of the invention non-itemized inventory may be held within enclosures or other containers. Such areas may include cabinets with shelves for holding such items as well as environmentally controlled chambers including refrigerators, high temperature chambers, low humidity chambers and other types of containers where medical items may be stored prior to use.

Figure 45:
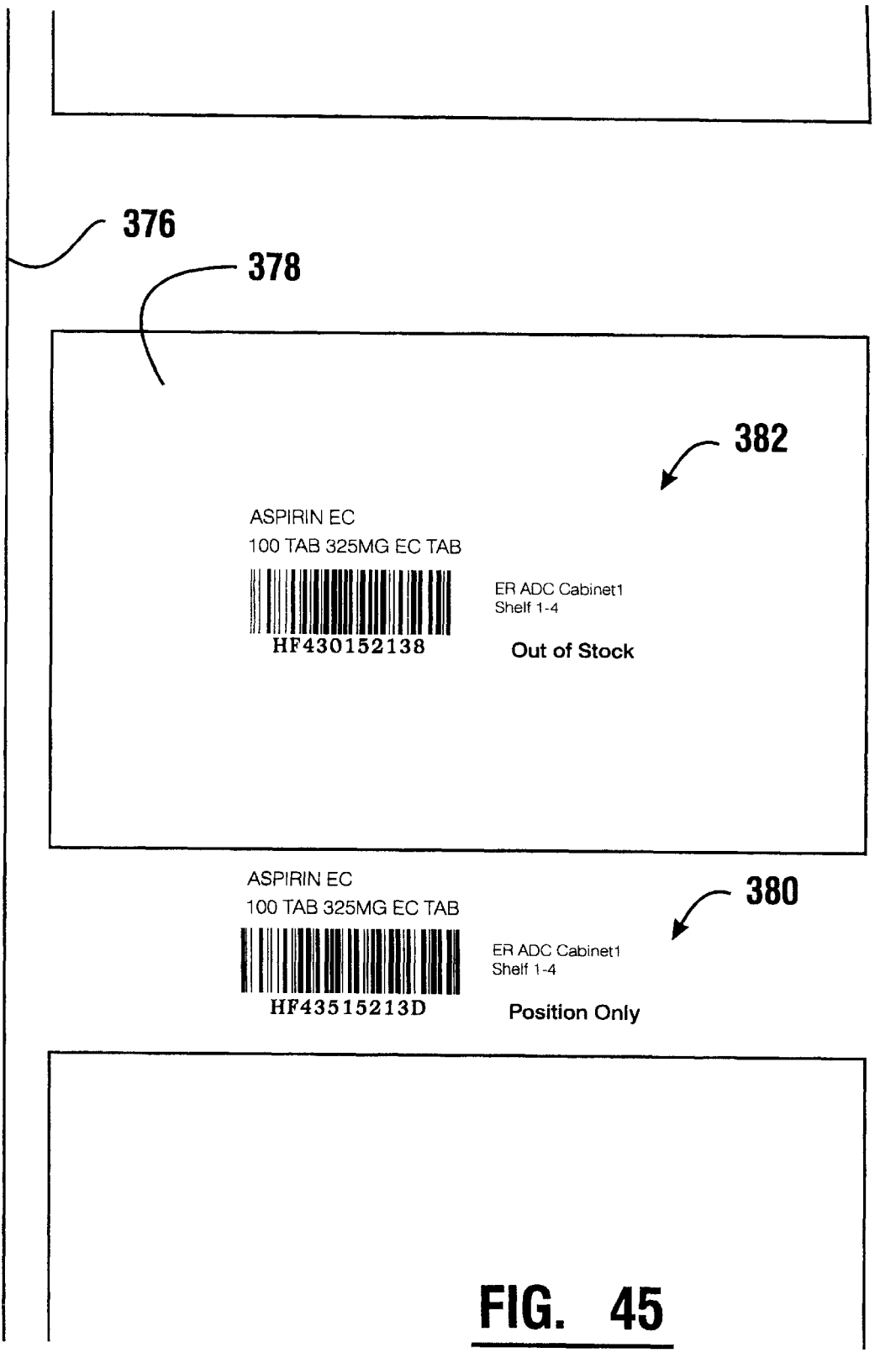
FIG. 45 is a schematic view representative of placement of labels similar to those shown in FIGS. 41 and 42 adjacent a storage location for a medical item.

In the alternative form of the invention described with reference to FIG. 40, certain storage locations are controlled by an access control device such as the locks of an electronic lock drawer or refrigerator. Storage locations are also marked with machine readable indicia of the type previously described. FIG. 45 shows an example of a single drawer 376, within electronic lock drawer unit 344. Drawer 376 includes a storage location 378 for storing medical items therein. As shown in FIG. 45, the storage location includes machine readable indicia in the form of a label 380, which indicates the location designator for the storage location as well as the medical item type stored therein. Storage location 378 further includes further machine readable indicia in the form of a label 382, which is an out of stock label. As shown in FIG. 45, the out of stock label 382 is positioned on the bottom surface of the storage location, so that it becomes accessible when all the items have been removed.

It should be understood that for storage locations which hold medical items which are counted and/or tracked by unit, the computer may calculate, and the data store may include, data representative of the number of units remaining in each storage location. However, it is also possible to include among or on the units of medical items machine readable indicia, which can be used to indicate that the number of medical items in the storage location has fallen to a level where restocking is required. Such indicia may be on the item which the user can scan when the item is taken. Alternatively, the indicia may be on a card or other divider placed between the medical items. In either case when the indicia is scanned the system is apprised of the number of units remaining at the location.

In the alternative form of the invention not only are each of the storage locations marked with machine readable indicia, but the access control devices themselves, such as the electronic lock drawer or refrigerator, are marked with unique indicia. In the case of electronic lock drawer 344 this may include labeling the entire electronic lock drawer unit with a single machine readable indicia. Alternatively, it may include labeling each drawer (or storage location within a drawer or other interior area) in the electronic drawer unit with such indicia. This indicia may be used in a manner later explained to selectively open the electronic lock drawer unit. Of course a similar approach may be taken with refrigerator or other devices which house medical items.

The alternative form in the system 322 shown in FIG. 40 includes a report generating means which is schematically indicated by a printer 384. Printer 384 may be positioned at a nursing station, restocking staging station or other location that is convenient for users of the system. It should be understood that while only one printer is shown, additional printers or other types of report generating means may be included in the system. The printer 384 is in operative connection with a computer 386. Computer 386 operates in accordance with programmed instructions and includes an internal memory or data store therein. Computer 386 is in operative connection with the network 328.

The printer 384 is operative responsive to the programmed instructions stored in connection with the computer 386 to generate reports schematically indicated 388. The reports produced by the report generating means preferably include both human readable indicia as well as machine readable indicia. As later discussed in detail, reports which include such indicia may be produced for use in dispensing medications as well as for restocking the storage locations of the system.

In the alternative form of the invention, storage locations may be labeled with other types of machine readable indicia. Such indicia are recognized by the reader in accordance with its configuration. In certain embodiments "prefix" labels or similar indicia may be applied. Such prefix labels indicate a particular quantity condition. The prefix labels indicate the quantity condition exists at the location corresponding to the next location indicia read. In the preferred form of the invention the quantity condition associated with the prefix label takes precedence over any quantity condition associated with the next label that is read, provided the next label is read within a set time which is established in the reader configuration.

For example, a single prefix label indicating a "restocked" quantity condition may be placed adjacent to several storage locations. A restocking user may indicate that he or she is filling an empty storage location by reading the "restocked" prefix label, and then reading the "out of stock" label or "below par" label at the location within the set time. Because the prefix takes precedence over other quantity conditions, the other quantity condition in the label is disregarded and the reader stores data which indicates that the particular storage location has been restocked.

Other types of prefix labels indicating other types of quantity conditions may be placed adjacent to storage locations and used in a similar manner. Such other prefix labels may be associated with quantity conditions such as "below par", "out", "out of stock, emergency restocking needed", "one unit taken" or other quantity conditions. Reading a prefix label indicates the quantity condition for the next label read which includes a location identifier (provided it is read within the set time) regardless if there is a different quantity condition indicated on the label that includes the location identification data.

In the alternative form of the system the configuration of the reader determines a quantity condition being indicated based on a hierarchy. A quantity condition indicated by a prefix label is at the top of this hierarchy. Thus, prefix label data when read takes precedence over any other quantity condition that may be included in indicia subsequently read by the reading device or established through the configuration of the reading device.

The second tier in this hierarchy is preferably the "out" quantity condition. Thus, if a different quantity condition is established by the configuration of the reader, and a label indicating an "out" condition at a storage location is read, the reader configuration will interpret this as an "out" indication at that location. However, if a prefix label had been read first, the quantity condition associated with the prefix label would be indicated because prefix labels are higher in the hierarchy.

As later explained, the reader includes data representative of authorized users. The data representative of certain authorized users has stored in correlated relation therewith a quantity condition that the user normally reports or performs. For example, if a user normally takes medications for patients, the quantity condition associated with that user data would be "one taken". As a result, when that user is "signed on" the reader, and reads a label which includes location indicia, the configuration of the reader will interpret the reading of the location indicia as indicating the "one taken" quantity condition at that location. This would be true unless a "prefix" or "out" label had been scanned.

As later discussed, users may have various quantity conditions associated with them. In addition to "one taken" for users who normally take items, restocking users may have the "restocked" quantity condition associated with their identifying data. Other types of quantity conditions can be assigned to particular users who normally perform the act or function associated with their associated quantity condition.

The configuration of the reader preferably provides a time period for a user who has identified himself or herself as operating the reading device, to begin reading location indicia where the quantity condition associated with the user has occurred. If the reader "times out" without location data being read, the next read location will not be treated as having the quantity condition associated with the particular user.

The lowest level in the hierarchy is one where no user with an associated quantity condition has indicated that he or she is operating the reader, and no "out" or "prefix" label has been read. At this lowest or default level, the configuration of the reader interprets the reading of indicia which includes a quantity condition and location as the condition existing at the location. If the indicia does not include a quantity condition, and only location data is read, the configuration of the reader interprets that as a "below par" quantity condition at the particular location. This is done provided the location is one where the medical items are not counted as indicated by the system configuration. If the location indicia read is of an improper type such as in a dispenser where "below par" is not appropriate, the configuration causes an "error" signal indication to be given. Such error indications are also given when any operation of the reading device is attempted which is incompatible with the configuration of the reader.

In operation of the alternative system shown in FIG. 40, the reading device 348 is operated by users of the system to accomplish dispensing and restocking activities. In a first form of this alternative embodiment the reading device is operated to perform activities comparable to those previously described as accomplished using the display terminal. The reading device includes the screen 350 which serves as an output device, as well as input devices 352, which enable it to be operated in a manner similar to the display terminal 338. As previously discussed, the reading device 348 includes a processor and a memory which enables it to operate independently of the processor and memory of the display terminal. In this form of the invention the reading device is a bar code scanner, Model PDT 3100 made by Symbol Technologies. Of course in other embodiments, other reading devices may be used.

The reading device may be connected to the system by a data line as shown. Alternatively, the reading device may connect to the system by wireless communication methods, such as IR or RF. Inductive of capacitance coupling approaches may alternatively be used, as well as periodic electrical coupling techniques.

Figure 47:
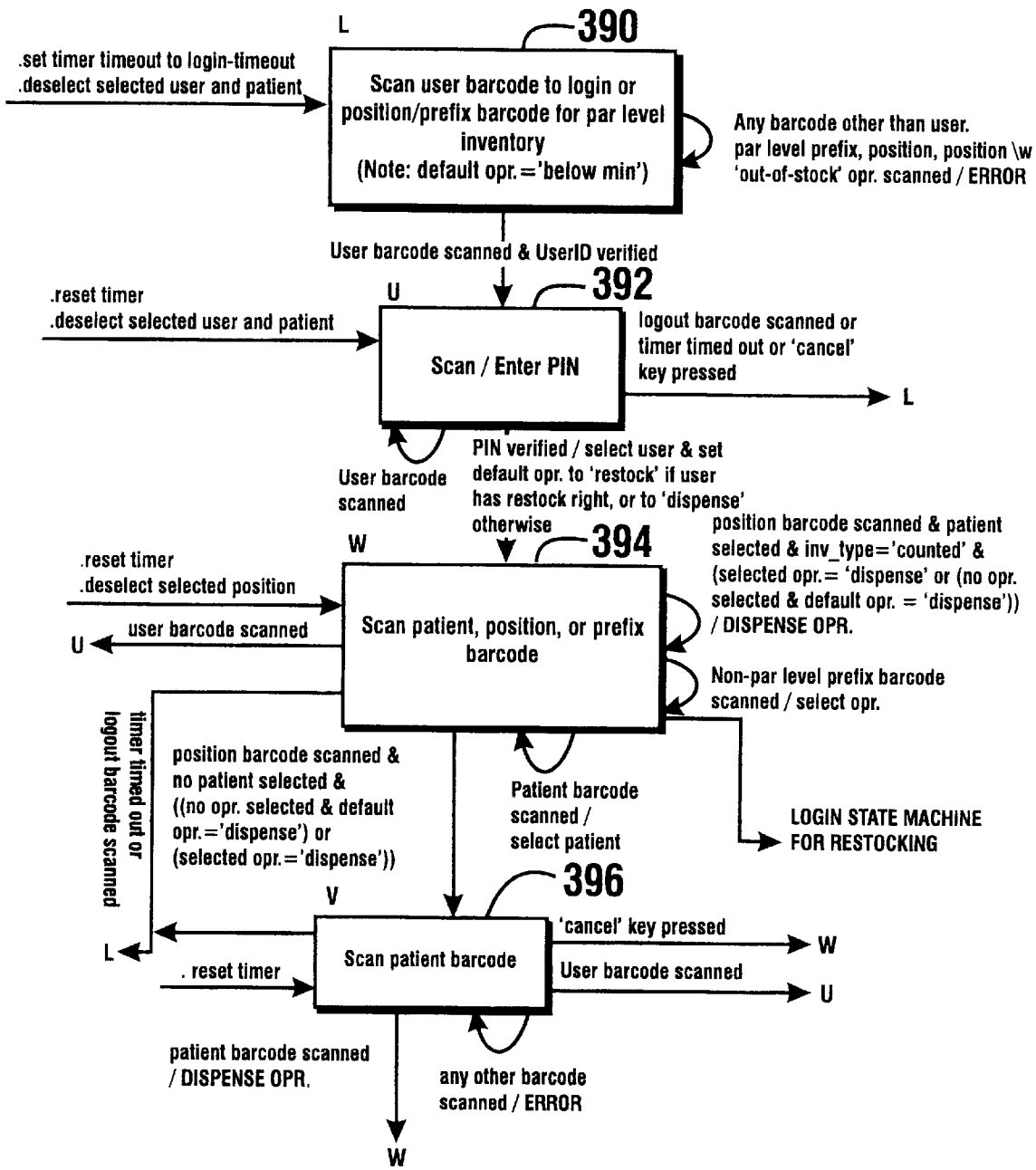
FIGS. 47–49 are a logic flow diagram showing steps that are carried out in the reading device of the alternative embodiment of the system shown in FIG. 40.
Figure 48:
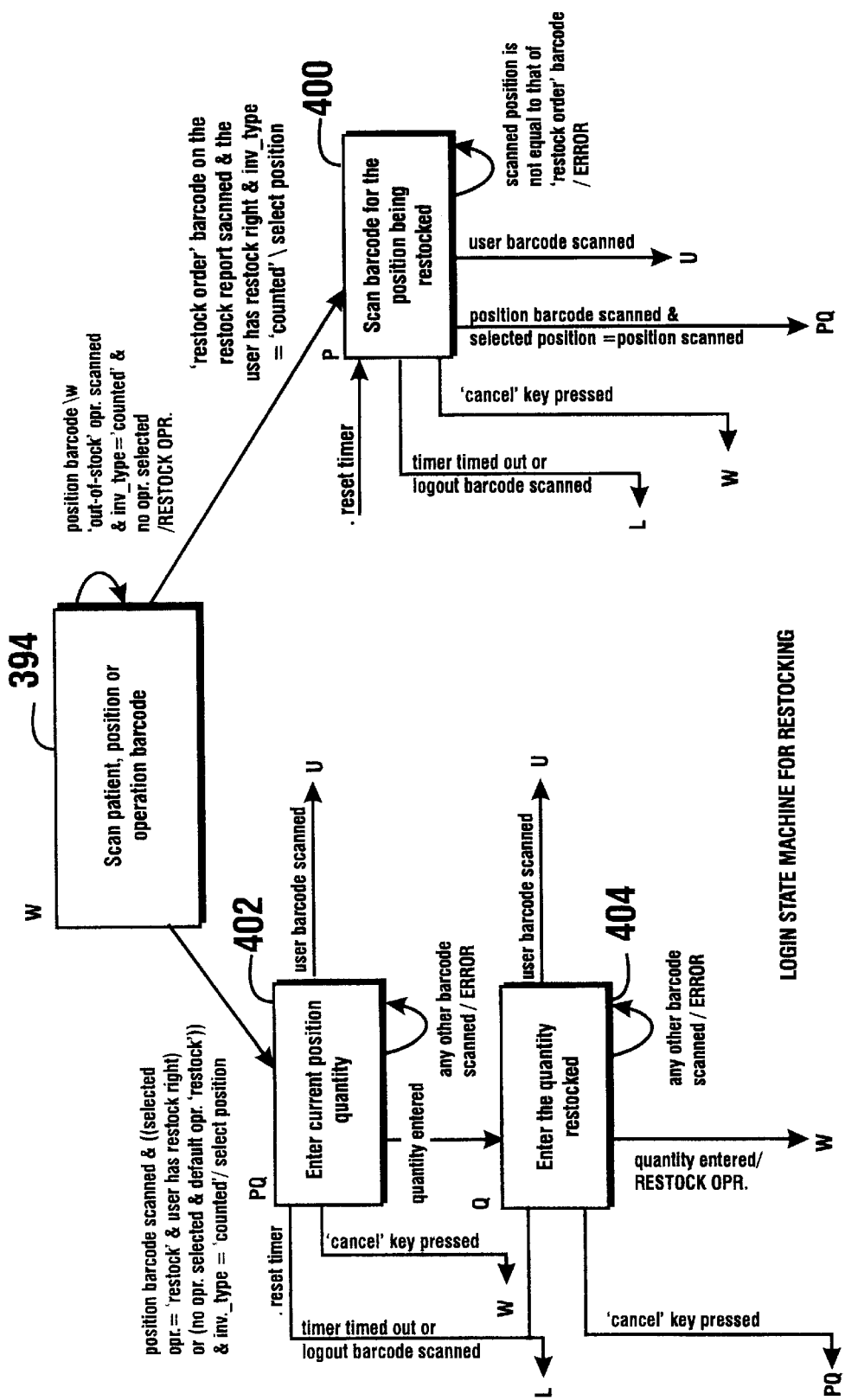
Figure 49:
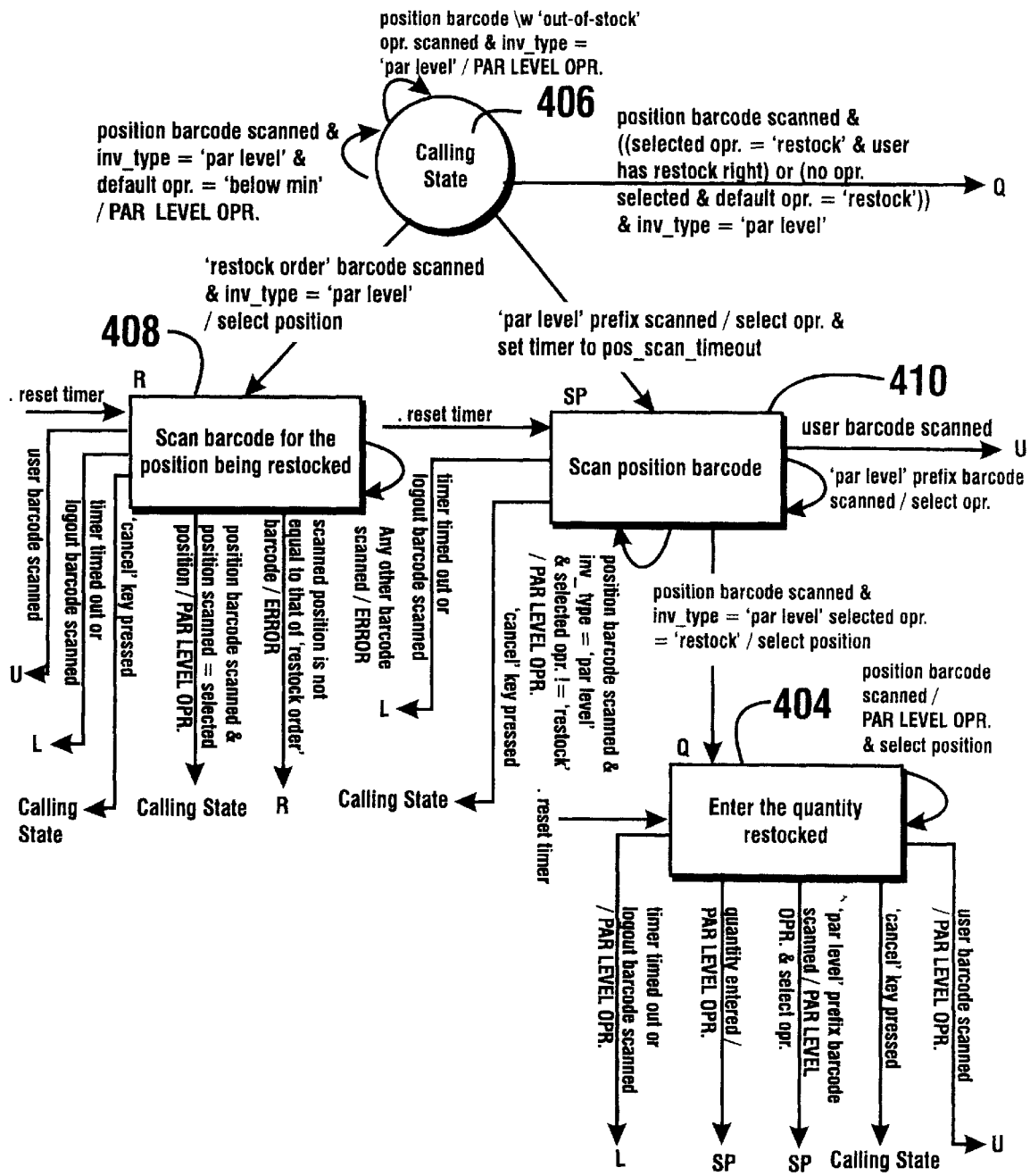

In a first mode of operation, the reading device operates in accordance with the logic flow shown in FIGS. 47–49. As previously discussed, all authorized users of the system are preferably provided with badges, identification cards, identifying articles or have distinguishing features which include machine readable indicia identifying them as authorized users of the system. The memory in the reading device 348 is configured to hold information concerning the indicia associated with authorized users. It is also preferably configured to store and hold each user's personal identification number (PIN) uniquely associated with the user. The reading device also holds the particular quantity condition function data, such as dispensing or restocking, which certain users are associated with. All of this information is established in the data store 326 in the course of setting up the system and is down loaded into the configuration of the reading device 348 through an interface which resides in the display terminal 338. The reading device 348 is configured so that it defaults to providing a "below minimum" quantity condition message in the event that no other quantity condition is specified. The reading device 348 is also configured to produce transaction messages as well as other messages which are sent to other components of the system. These include messages which update the information stored in the data store 326.

The logic flow for the reading device begins as represented in FIG. 47. A user wishing to operate the system through the reading device 348 begins with the processor executing a process 390 in response to a user scanning a machine readable indicia, which for purposes of this example will be a bar code. The bar code scanned may be indicative of a particular supply storage location. If such location indicia is scanned without first scanning indicia which identifies a user, the hierarchy in the configuration of the reading device previously described interprets the activity as indicating that the medical items stored in the position scanned are "below minimum". In response, the reading device 348 generates a transaction message which indicates that the medical items in the storage location have this quantity condition.

Alternatively, a user may find that a particular storage location is out of stock. In response to observing this quantity condition, the user may scan the bar code label similar to that shown in FIG. 42. In response to scanning such a bar code process 390 causes a transaction message to be generated which indicates the out of stock quantity condition at the particular storage location. In accordance with the hierarchy in the configuration data, the "out" quantity condition is indicated when this label is scanned, regardless of whether the user is logged on and whether the user is associated in the data store with a particular quantity condition.

Alternatively a user may indicate a below minimum or out of stock condition by scanning the out of stock bar code at a storage location which will cause similar transaction messages to be generated. Storage locations may be provided with "below minimum" labels similar to those shown in FIG. 44 so that a user may indicate the below minimum quantity condition by scanning this label, without having to log on the system. Alternatively, if a user who normally takes medications is logged on the system, a "below minimum" condition at a location can be indicated by scanning a "below minimum" prefix label and then any label which includes the location indicia for the location where the below minimum quantity condition exists.

Enabling a user to scan the bar code labels which are representative of the below minimum and out of stock quantity conditions is a time saving feature. This is particularly true when the user is indicating such conditions for non-itemized inventory. In such circumstances the user is not required to log into the system, but nevertheless can indicate these conditions so that persons with the responsibility for restocking the storage locations may be notified.

As indicated in process 390, if a user wishes to log onto the system using the reading device they may first scan the bar code or other machine readable indicia on their badge, identification card, etc., using the reading device. In response to the user scanning a proper badge, identification card, or other item, the processor in the reading device proceeds to the next process in the logic flow, process 392. Of course as indicated in process 390, if any bar code other than an appropriate bar code is scanned, an error signal is generated, an error indication is presented on the screen and the reading device returns to process 390 in the logic flow to wait for further input.

In process 392 a user is prompted through the screen 350 on the reading device to input their PIN. A user can do this through the keypad which is part of the input device 352.

The configuration of the reader provides a predetermined time after scanning the badge or identification card for a user to input their PIN. If this input is not accomplished within the set time, the logic flow returns to process 390. Similarly a user may return to process 390 by pressing a "cancel" key on the input device 352 or by sending a log out message. In the preferred form of the invention the log out message is generated by scanning a particular bar code which is conveniently placed for this purpose. In addition, or in the alternative, the reading device may be programmed to generate a log out message when it is returned to its cradle 354.

If a user proceeds to enter a PIN number within the time period provided, the reading device 348 checks the PIN against the data stored in its memory. If the PIN is verified as correct the configuration changes the operation of the reading device so that the subsequent scanning of position bar codes is taken to represent the particular quantity condition function which is associated with the user. As a result, if the stored configuration data indicates that the user normally dispenses medications, the subsequent scanning of a position bar code will be interpreted as a dispense of that medical item (a "one taken" quantity condition). Likewise, if the stored data indicates that a user is normally involved with restocking activities, the subsequent scanning of a location bar code will be taken as a restocking event. Of course other types of quantity condition functions (or a no quantity condition function) may be associated with particular users.

In the alternative form of the invention the report generating device, which is printer 384, generates reports. The report generating device preferably produces reports which include the names of patients who may receive medical items as well as indicia, such as bar code, which corresponds to each patient. In the preferred form of the invention, the reports further include the medical items that have been prescribed for the patients as well as machine readable indicia representative thereof. This information is based on the information stored in the data store. Preferably the reports are limited to patients in the rooms which have been designated through the programming of the system as associated with the particular display terminal to which the reading device 348 is attached. In this embodiment a computer program called "The Bar Tender" commercially available from Seagull Scientific Systems is used for generating bar code indicia. Of course, in other embodiments other programs may be used for producing the text and indicia which comprise reports.

In the alternative form of the invention, a patient may be selected using the reading device 348 by scanning the bar code associated with the particular patient printed on the report. The user is preferably prompted to do this as the configuration logic executes process 394, as shown in FIG. 47. If the user scans a patient bar code, a timer built into the configuration of the reading device waits a time for the user to scan a position bar code. The user may accomplish this by scanning the position only bar code similar to the one shown in FIG. 41, if the medical item to be taken is stored in an open storage location. If such a bar code is scanned a transaction message will be generated that such item was taken by the user for the indicated patient. The user may indicate that several of the same items were taken by scanning the bar code a number of times corresponding to what was taken. Similarly, the user may scan several different locations to indicate the different items taken for the patient.

If the medical items which are needed for the patient as indicated in the report 388 include items positioned in an electronic lock drawer 344, the user may scan the bar code on the electronic lock drawer. If the data stored in the data store 326 concerning the user indicates that they have authority to access the electronic lock drawer, such information will be included in the configuration data for the reading device. As a result, when the user scans the bar code associated with the electronic lock drawer, the access control system which controls opening the drawers, will open and make the medical items therein accessible. The user may then open the drawers where the medications are needed and may indicate the taking of medical items for the patient by scanning the position labels for the storage locations holding the medications, such as label 380 shown in FIG. 45. This generates a transaction message indicating that the medical items stored in the storage locations for which the labels have been scanned have been taken for the designated patient.

In alternative forms of the invention, each of the drawers in an electronic lock drawer unit may be labeled with machine readable indicia which enables the access control device to provide access to each drawer individually. Likewise, the reading device 348 may be configured to provide access for users to the drawers selectively. This may be desirable when drawers of the electronic lock drawer unit 344 contain medical items which are only to be accessed by certain personnel, or which require two authorized users to log-in in order to access the medical items in a particular drawer. As will be appreciated from the previous discussion concerning the display terminal, the reading device 348 may be configured to require two authorized users to log in to achieve the dispense of a selected medical item such as narcotics, in a manner comparable to that done using the display terminal.

It should be appreciated that while the process of using the reading device in connection with electronic drawer devices has been described, similar processes may be used in connection with other devices which hold medical items. These include refrigerators such as refrigerator 527, cabinets and various other types of units which include storage locations for medical items.

After a user has scanned the bar code at the storage locations from which medical items have been taken for the indicated patient, the user may log off the system as indicated in process 394 which returns the processor to process 390. Alternatively, the user may scan the indicia corresponding to another patient and may scan the storage locations for the medical items taken for that patient in the manner previously described. The user may take medical items for a number of patients before logging off the system. The configuration within the scanner causes transaction messages to be generated which include information about the dispense events. Such transaction messages preferably include data representative of the patient, the medical item and its storage location, the user of the system taking the item, as well as the time and date information that the item was taken. Of course the transaction messages also include data representative of the quantity condition which the transaction message represents. In the case of a dispense quantity condition, the transaction message includes a quantity condition indication which includes data representative of a dispense. This indication distinguishes it from transaction messages which indicate other quantity conditions such as below minimum, out of stock or restocked. The processor and the configuration in memory in the reading device serve as a quantity condition indicating device which operates to generate the quantity condition indication which is included in the transaction messages.

As shown with reference to the logic flow associated with process 394, if an improper scanning operation is performed, the logic returns the system to an appropriate process. The configuration of the reading device is also set up to provide the user with appropriate textual prompts. For example, the configuration of the reading device causes the system to consider the next transaction to be a dispense due to data stored for a user who has logged on the system. However, rather than indicia associated with a patient being scanned next, a bar code associated with a storage location is scanned. In this case the logic in process 396 is executed by the processor in the reading device. Process 396 directs the logic flow to the appropriate process based on a sequence of inputs made. Further as shown with regard to process 394, a user operating the reading device is free at any time to scan the bar codes to indicate a below minimum or an out of stock quantity condition at a storage location, which causes a transaction message to be generated corresponding to the condition which is read.

Alternative embodiments of the invention may operate dispensing devices, such as dispenser 346, or enable access to storage locations which are controlled by access control devices, such as lock drawer unit 344, or refrigerator 527, in response to indicia which corresponds to the medical items prescribed for patients printed on the reports. The reading device 348 is preferably configured to include data representative of the storage locations within the dispenser and other devices. A user wishing to dispense a medication from a dispenser, rather than scanning a storage location or an electronic lock drawer unit, may scan the indicia corresponding to the medication desired from the report. In response, the reading device causes the medical item to be dispensed from its storage location in the dispenser, if that is where the item is found. Similarly, if the medical item corresponding to the scanned indicia is stored in the electronic lock drawer or the interior area of the refrigerator, the access control device will enable the drawer or refrigerator holding the item to be accessed by the user.

The ability to dispense and access medications based on the machine readable indicia from the reports further increases the speed at which items may be dispensed and the information recorded for eventual storage in the appropriate data store of the system. Further, in this alternative form of dispensing medications, a confirmatory step may be required by the configuration of the reading device so as to provide an indication that the requested item was in fact dispensed or taken. This may include for example the user providing an input through the keypad, which is part of the input device 352 of the reading device, or alternatively scanning machine readable indicia on the dispenser, or on their identification card or badge. Such functionality may be readily included with the logic which is part of process 394.

The various signals which have been scanned or otherwise input into the reading device 348 are used to generate the transaction messages. This may be done as data is being read or is preferably done after the user logs off the reading device. The transaction messages are standardized within the system and are generated in accordance with the configuration data stored in the reading device. The transaction messages are preferably dispatched in a batch mode after the user logs off to avoid slowing the user down waiting for messages to be transmitted to other parts of the system. When the user logs off the transaction messages are sent through the interface in the display terminal 338 and into the network 328 from which they are received by computer 324 or other computers connected to the system. The transaction messages are used to include information about the quantity conditions and other events which have been carried out, in the data store 326. Of course it should be understood that the transaction messages may be sent to a number of different computers and modify data in numerous data stores depending on the programming of the particular system.

In this embodiment of the invention, after the transaction messages have been sent by the reading device 348 to other parts of the system, the computer 324 is operative to down load current configuration data into the reading device. This assures that the most current information is configured in the reading device.

In the operation of the alternative version of the invention, the transaction messages received by computer 324 may be indicative of a need to replenish the supplies of medical items at certain storage locations. This is true regardless of whether the transaction messages are generated based on inputs to the reading device or to the display terminal. In response to such conditions being indicated, computer 324 in cooperation with computer 386 or other similar computers positioned elsewhere in the system and connected through the network 328, is operative to cause a report generating device such as printer 384 to print a report concerning the storage locations needing to be restocked. Preferably the report includes information concerning the storage locations requiring restocking, the medical items stored therein, and the quantities of such medical items that are needed. The report preferably includes this information both in human readable and in machine readable form.

A person who is to restock the storage locations for which the report is printed may use the reading device 348 to facilitate the input to the system of restocking information. The restocking function is further demonstrated with reference to the logic flow processes shown in FIG. 48. A restocking user who logs into the system does so in the manner previously described with regard to a user who conducts dispensing activities. However, such a restocking user will have data stored in the configuration of the reading device which indicates that they perform a restocking function. From the process 394, with a restocking user logged on, the user preferably scans the bar code corresponding to a particular storage location to be restocked. An example of restock order bar code found in a restock report is indicated 398 in FIG. 46.

Upon scanning the restock order bar code on the restock report, the logic executed by the processor in the reading device next moves to process 400. In process 400 the user scans the bar code for the storage location being restocked. This may be the bar code corresponding to an open storage location, a location in an electronic lock drawer, a location in the interior area of a refrigerator or a location in the interior of a dispenser. The reading device 348 is preferably configured to prompt the restocking user to scan the position only bar code. After the position bar code has been scanned the logic next moves to process 402 in which a user enters the quantity of medical items currently stored in the position. This is done by the user counting the items and using the numeric keys in the input device 352 of the reading device. The user is preferably prompted to do this on the screen 350 by the configuration of the reading device. The requirement to input existing quantities is only carried out for medical items which are itemized and counted. For non-itemized items where absolute quantities are not a concern, the reading device is preferably configured to enable a user to avoid the input of current position quantities.

The current position quantity information is useful for counted and itemized inventory items as it can be compared to information stored in the data store 326 to verify that dispense events have been properly recorded. If a discrepancy has occurred, the computer 324 is preferably programmed to provide an indication thereof at the administrator's workstation 336 or at another appropriate output device in the system.

After a user has input the current position quantity at process 402, the logic next moves to process 404 in which the user enters the quantity which is being restocked in the storage location. The user is preferably prompted to do this by prompts presented on the display 350. Of course as indicated in processes 400, 402 and 404, if a user makes an error in the sequence of scanning or inputting, indicates that they wish to cancel the transaction, or the timers included in the configuration time out without receiving the next required input, the logic returns to an appropriate process.

It should also be noted in FIG. 48 that a restocking user is also enabled to restock without using the restock order bar code on a restocking report. As indicated in the logic flow a user who has restock rights is enabled to move from process 394 to process 402 by scanning the position on the storage location to be restocked.

Of course restocking operations cause the reading device to generate signals which are indicative of the quantity condition associated with a position being restocked. The reading device is operative based on its configuration to build transaction messages corresponding to the restocking activities at the various storage locations. These transaction messages include data representative of the user performing the restocking activity, the storage location, the medical item involved, as well as the time and date of the activity. Again these transaction messages may not be transmitted to the other components of the system until after the user logs off the system. This assures that the restocking user may perform their operations at the fastest possible rate.

FIG. 49 shows the logic flow associated with the generation of transaction messages which indicate that the number of medical items stored in a storage location is below minimum or out of stock. Generally such transaction messages will be generated by scanning a position bar code when the reading device is in the "default" mode due to no user being logged on. Alternatively, a prefix bar code indicia representative of a "below minimum" with location indicia, or an "out of stock" indicia at a location may be scanned at any time. This is represented by logic process 406 which is indicated as the calling state in FIG. 49. It should be understood that the calling state may be either process 394 or process 390 as indicated by process 406. As shown in FIG. 49 from the calling state 406, provision is made when a restock order bar code is scanned from a report, to move to logic process 408 in which a user scans the bar code for the position being restocked. This enables a restocking user to indicate that the position is being restocked. Also from the calling state, a user can scan a prefix bar code which may include quantity conditions such as below minimum, out of stock, or restocked, and then a bar code including a position or location. This causes the logic to move to process 410 which produces transaction records accordingly.

The logic flow process described in FIG. 49 provides system flexibility. This logic enables the user to scan sequentially a prefix label, and then a position label so as to selectively indicate a particular quantity condition for a storage location. This may be advantageous, such as for example, when a restocking user is scanning machine readable indicia from a report and from storage locations. Of course many arrangements of machine readable indicia both on reports and storage locations, as well as logic flow processes are possible depending on the needs of the system operator.

The alternative system 322 shown in FIG. 40 may be programmed to have the reading device 348 configured to operate in conjunction with the display terminal 338, rather than as a completely separate user interface device. In some alternative embodiments it may be desirable for users to select patients using the screen 340 of the display terminal in the manner previously described when dispensing is conducted using the touch screen interface of the display terminal. Thereafter, the user may indicate taking of medical items from storage locations by scanning the machine readable indicia associated with those storage locations with the reading device. Likewise dispensers, electronic lock drawers, refrigerators or other storage locations, access to which is controlled by an access control device, may be operated so as to render medical items therein accessible in response to scanning of indicia associated therewith by the reading device. The taking of such items for the patient selected at the display terminal may be recorded in the data store upon such medical items being rendered accessible by the access control device, or may require further input to confirm the taking of the item either by scanning or by an input to the display terminal. The sequences and processes may be varied to suit the level of security desired for the particular medical items involved.

It should be understood that while the report generating means of the described alternative embodiment is a printer which enables the printing of bar codes, other embodiments may include other types of devices which may produce machine readable indicia. These may includes devices which include hard copy or other types of displays or signals, which are capable of being read by a machine. Alternatively, in certain embodiments the reading device may be programmed to read human readable text provided on a report or other output device. In alternative embodiments audio, magnetic or other indicia may be substituted for the optical type machine readable indicia that have been previously described.

A further novel aspect of the alternative embodiment of the invention is associated with its capability of operating to perform dispensing and restocking activities despite other components of the system becoming inoperable. Specifically the reading device 348 may continue to operate to record dispense and restock transactions despite a malfunction of the display terminal 338, network 328 or any of the other connected computers or systems. As previously discussed, the reading device 348 generates transaction messages in response to the signals generated therein. The reading device is preferably configured so that if the batch transactions cannot be successfully transmitted to other parts of the system, such transactions will continue to be held in memory in the reading device. It may be desirable to continue to have the reading device hold a record of the transactions for a period of time, even though they have been successfully transmitted to other components of the system. This enables recovery of the data should it later be lost from the data store 326 or other connected system components.

The capability of the reading device 348 to store and later forward such transactions creates a possibility that quantity condition information may reach the data store 328 after later, more current information has been stored therein. It would be undesirable to modify more current information with previously generated data which may no longer be accurate.

To overcome this problem the transaction messages, as previously discussed, include a time of each transaction. The time preferably includes both time and date. The data store 326 likewise includes data representative of a time (and date) the data which is used to update the data store was generated. Upon receiving data from a reading device (or preferably any device such as a data terminal or other system component which has the capability of operating independently) the computer connected to the data store is operative to compare the time information associated with the transaction data it is receiving with the transaction time of the most recent data that it has already received. If the time associated with the transaction message it is receiving is more recent than the update to the data it has most recently received, the data in the data store is updated accordingly as is the transaction time information associated with the update.

On the other hand, if the message being received by the data store is associated with a transaction which occurred at a time which proceeds a more recent update to the same data, the computer 324 will not supersede the more recent data. Rather the computer is programmed to store the transaction message data and use it for further processing. In certain cases the message will be sent to the administrator's workstation so that a system operator may review whether the data which the system has maintained needs to be modified.

An example of a situation where the computer 324 may have received more recent data before older data is received is when persons restocking the system use other types of input devices to indicate restocking data. The reading device 348 may generate a transaction message which indicates that a particular storage location is out of stock. However, due to the periodic transmission of the data from the reader, or other operational factors, the data store may not have received the transaction data for a time after the user reads the indicia from the location. A restocker using a separate message connection path into the network, such as a portable terminal, may have restocked the position subsequent to the out of stock indication being read. The restocker's data may have been received at the data store. Without the provision that is made in this embodiment for checking the time information in the transaction messages, a subsequent receipt by the data store of the message that has been in storage in the reading device would wrongly cause the data store to indicate that the storage location was out of stock. Because the system includes the feature for selectively updating the data based on the time associated with the transaction message, the risk of such problems is minimized.

The ability of the system to selectively update the data store based on the time that message data originated enables the operation of alternative embodiments of the invention in which dispensers, lock drawers, refrigerator lock modules and other devices need not be in continuous communication with the other components of the systems.

In such an alternative embodiment electronic lock drawers, refrigerator lock modules, dispensers and other medical item storage devices which selectively control access to medical items, similar to those previously described, are used. However in this alternative embodiment such devices include or are in operative connection with a local processor and a memory. The local processor is connected to a local message input device and a local message output device of conventional types which enable the processor to send and receive messages. In one form of this embodiment the local input and output devices include IR receivers and emitters respectively, but other types of wireless or other connections may alternatively be used.

In this alternative embodiment the reading device used is similar to reading device 348 except that the reading device preferably includes a wireless interface that is capable of communicating with the display terminal or the network, as well as with the local message input device on the dispensing devices.

The local memory on the dispensing devices is preferably configured to hold data representative of authorized users, as well as medications stored in the various storage locations in the dispenser. The local memory is also configured to cause the processor to operate to make medical items available in response to an appropriate message received at the local message input device. The local memory is further configured to generate transaction messages which include data similar to transaction messages generated by the reading device. The configuration of the local memory in the dispensing device is preferably established by downloading data into the local memory through the local message input device. This may be done using an IR communications interface in the network which communicates with the dispensers, or by using a portable terminal device to provide the configuration data.

In operation of this alternative embodiment, a user logs on the reading device in a manner similar to that described in the previous embodiment. The reading device operates in a stand alone manner based on its configuration data.

A user operates the reading device by scanning patient and medication data from reports or otherwise in the manner previously described. However, unlike the other embodiment where the reading device transmits its signal to the data terminal and the data terminal transmits a message on a data line to a dispenser, in this embodiment the reading device sends its output directly to the local message input device by IR coupling. The message from the reading device preferably includes data representative of the authorized user who is operating the reading device. The processor in the dispensing device preferably checks the user identity data against the configuration data related to authorized users in its memory. If the user is indicated as authorized, the dispenser makes the medical item indicated by the message available to the user. The reader also preferably provides as part of the message to the dispenser, data representative of the patient (if appropriate) and other data that is included in the transaction message eventually generated by the reading device. This information is also stored in the memory of the dispensing device. Of course, the processor in the dispenser may provide the time data and other data directly or from its local memory.

The dispenser through its local output device preferably provides data to the reading device representative of the storage location from which the medical item was provided. The reading device holds this data and incorporates it into its transaction message data.

The reading device is eventually again placed in communication with the network 328. This may be done by returning it to its cradle in which it is coupled by IR or in another manner to the network. The transaction messages produced by the reading device are used to update the stored data concerning the patients and the medical items in storage locations as in the previous embodiments.

Periodically data from the memory of the dispenser is delivered to the remainder of the system and used to verify the transaction messages from the reading device. This can be done through the local message output device being coupled to a receiving device connected directly to the network 328, or by use of a portable terminal which receives and stores the data. The portable terminal is eventually connected to the network. The computer comparable to computer 324 in this embodiment is programmed to compare transactions from the dispensers to those already received and to disregard duplicates of transaction already received. Any discrepancies may be directed to the appropriate function in the hospital or other facility in which the system is operated.

The reading device may also be used during restocking of storage locations in the dispensers in the manner previously described. The reading device provides messages which are used to update the stored data. The data from the memory of the dispenser may be used to verify the reading device data and to identify discrepancies.

As will be appreciated, this alternative embodiment has the advantages that the dispensers and storage locations are totally "stand alone" units. This offers greater flexibility in their placement and reduces cost of installation of the system. The alternative form of the system further provides the advantage that if the reading device is lost or damaged, records of any activity conducted since the reading device last sent messages to the network can be recovered from the dispenser memories. The dispenser memories may be configured to hold data for such time after providing the data back to the network to assure data recovery.

It should further be understood that in this alternative embodiment more than one dispenser or similar device may share the same local processor, memory and input and output devices. Further, open storage locations may have a local processor, memory and connected input and output devices adjacent thereto to store a record of the transactions conducted with the reading device at the open storage location. Of course such processors and memories would not need to be configured to perform any dispensing control activities which would simplify installation and operation. Other arrangements and alternative systems will be apparent to those skilled in the art from the foregoing description.

The restocking of the various storage locations within the systems of the previously described embodiments may be facilitated using a method which includes the positioning of removable liners within the storage locations. In the execution of this method the liners are stocked with medical items at a remote stocking location such as in a pharmacy within a medical facility or at an offsite packing location. The liners are preferably secured and labeled with indicia which indicate the locations where they are to be installed. This location identifying indicia may in various embodiments of the invention include specific location data, indicia representative of the particular type of medical items stored in the liner, or a combination of both.

The liners that have been loaded with the medical items are transported to the storage locations. The storage locations are then accessed by a restocking user in the manner established for the system. The previously installed liners are removed and the filled liners are then installed. The devices securing the new liners in the closed positions are opened either before or after installation of the new liners in the appropriate storage location. As later discussed, steps may be taken to assure that the liners are properly installed. Medical items from a previously installed liner may be transferred to the newly installed liner and a record thereof made. Alternatively the previously installed liners may be secured with the remaining medical items stored therein.

The new liners are installed to replace the previously installed liners in a plurality of different storage locations and dispenser devices, as well as in open or other types of storage locations. The previously installed liners are returned to the stocking location for an accounting of the medical items which may be still held therein, and for reuse.

Figure 55:
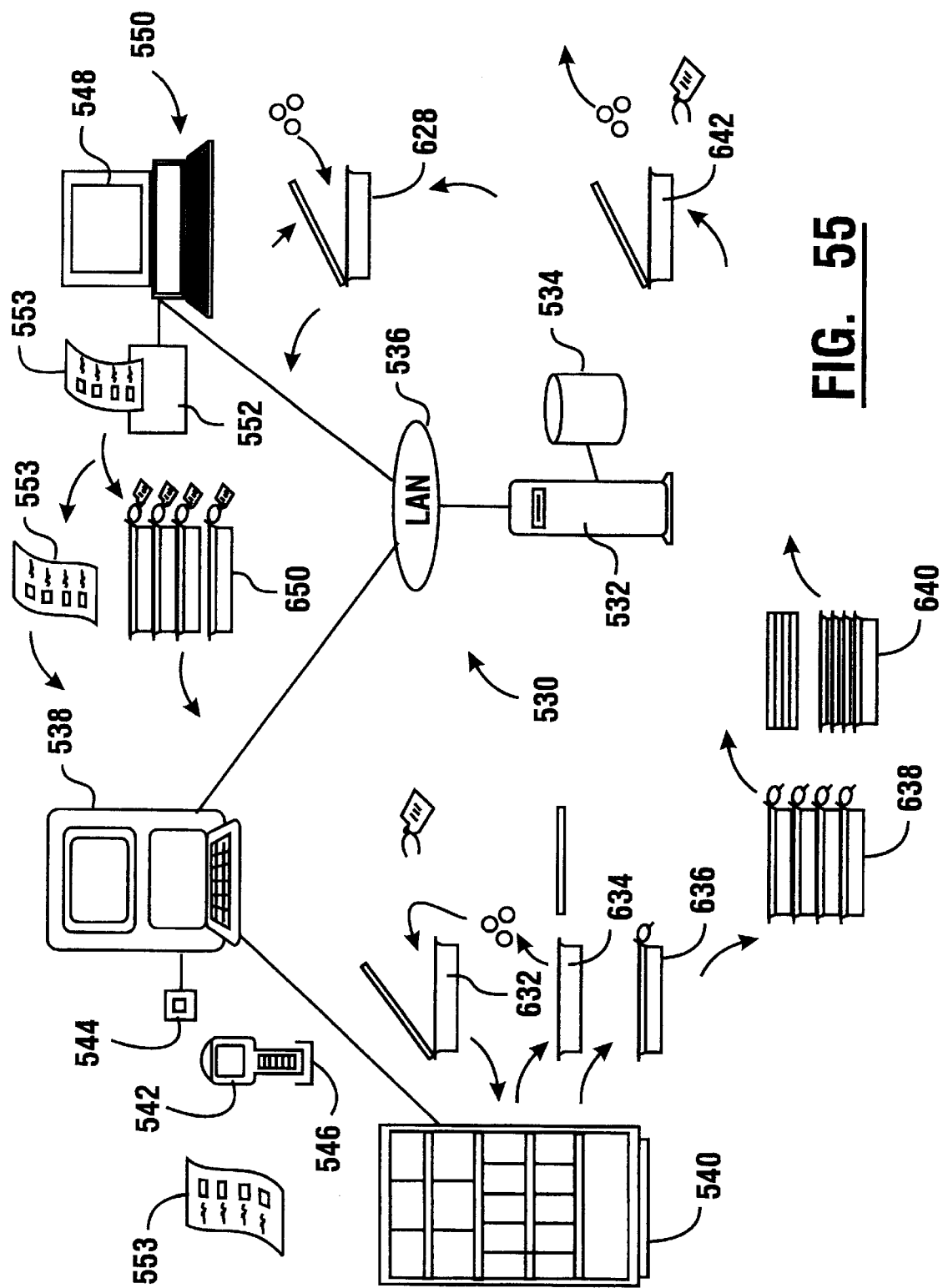
FIG. 55 is a schematic view of a system of the present invention which may be used to perform a restocking method for storage locations which includes removable liners.

A schematic view showing the steps of the restocking method is schematically represented in 55. FIG. 55 shows a system 530. System 530 may be similar to system 322 or other systems previously described. It should be understood that additional hardware and software features may be included in or connected to system 530, and that only certain features and components are shown to facilitate understanding of the method.

System 530 includes one or more operatively connected processors and data stores. This is schematically represented by computer 532, and data store 534 which is schematically shown. The processors and data store are operatively connected and enabled to communicate through a network schematically indicated 536.

A plurality of display terminals of the types previously described are connected to the network 536. This is represented by a display terminal 538. It should be understood that in one preferred embodiment the display terminals 538 may also include a processor and data store therein. The display terminal 538 is shown schematically connected to a dispenser device 540. In the embodiment shown the dispenser device 540 is an electronic lock drawer of the type previously described. It should be understood that a plurality of dispenser devices of the various types described herein may be used in carrying out the restocking method. Such dispensing devices may include cabinets, refrigerators and dispensers for varied types of medical items.

While in the system 530 the dispenser devices are shown connected to the display terminal, in alternative embodiments of the invention the dispenser devices may operate as stand alone devices in the manner previously described. Such devices rather than being in operative connection with other devices in the system on a generally continuous basis, may have only periodic connection to other components of the system.

The embodiment of the invention shown in FIG. 55 also includes a reading device 542. Reading device 542 is generally similar to the reading device 548 previously described. The reading device may be connected to the display terminal 538 by a line or through other communications methods. In one form of the invention the reading device 542 communicates through infrared signals. The display terminal 538 is in operative connection with an infrared transmitter and receiver schematically indicated 544. The reading device 542 may also be provided with a cradle 546 similar to cradle 354 previously described. It should be understood that various approaches may be used in embodiments of the invention for communicating between the reading device and the display terminal 538 and/or other components of the system. The reading device 542 may remain at a position adjacent to an associated display terminal or alternatively may to be carried by a restocking user to various locations throughout the system where restocking activities are conducted. In this way the transportable reading device operates in a manner similar to the reading device used in connection with stand alone dispenser units previously described.

In one preferred form of the invention a restocking terminal schematically indicated 548 is connected to the system through network 546. The restocking terminal 548 is preferably located in a stocking location schematically indicated 550. The stocking location is preferably an area where supplies of medical items are prepared. This may be a pharmacy within a medical facility such as a hospital, clinic or treatment center. Alternatively the stocking location may be a facility where inventories of medical items are available and may be packaged for transport. Alternatively a stocking location may comprise a manufacturing facility where medical items are manufactured.

The restocking terminal is preferably in operative connection with a report generating device 552. The report generating device in the embodiment shown is a printer which is capable of printing a restocking report schematically indicated 554. The restocking report 554 is preferably similar to the type previously described which includes both human and machine readable indicia concerning storage locations which require replenishment of the medical items therein and the type of medical item which needs to be replenished. In alternative forms of the invention the report generating device may be a device which provides such information either in a visual or machine readable form which can be transported and/or transferred so as to facilitate the restocking of the locations.

In one embodiment of the invention the report generating device produces labels with machine readable indicia which can be applied in association with containers for medical items. The indicia is preferably a bar code representative of the storage location. The bar code representative of the storage location may be a location designator or indicia representative of the type of medical item stored in the container. Alternatively the indicia may be a combination of both the location designator and the medical item type.

Although the embodiment described produces transferable labels with the report generating device, in alternative embodiments other devices may be used to produce labels or alternative forms of indicia or information which can be transferred to a container. This may include for example optical indicia or electronic indicia including processor chips which may be programmed and attached to medical item containing devices.

In alternative embodiments the liners may be marked with a generally permanent identifying indicator, such as serialized machine readable indicia. In such a system data representative of the type of medical item placed in each container may be input and stored in the data store. Further in a concurrent or subsequent step data representative of the indicator for the container and a particular storage location may be stored in correlated relation in a data store. This would result in the container being assigned or addressed for subsequent placement in the storage location.

The type of report generating device used and the indicia which are associated with the containers for the various types of medical items will depend on the configuration and operation of the particular system.

Figure 56:
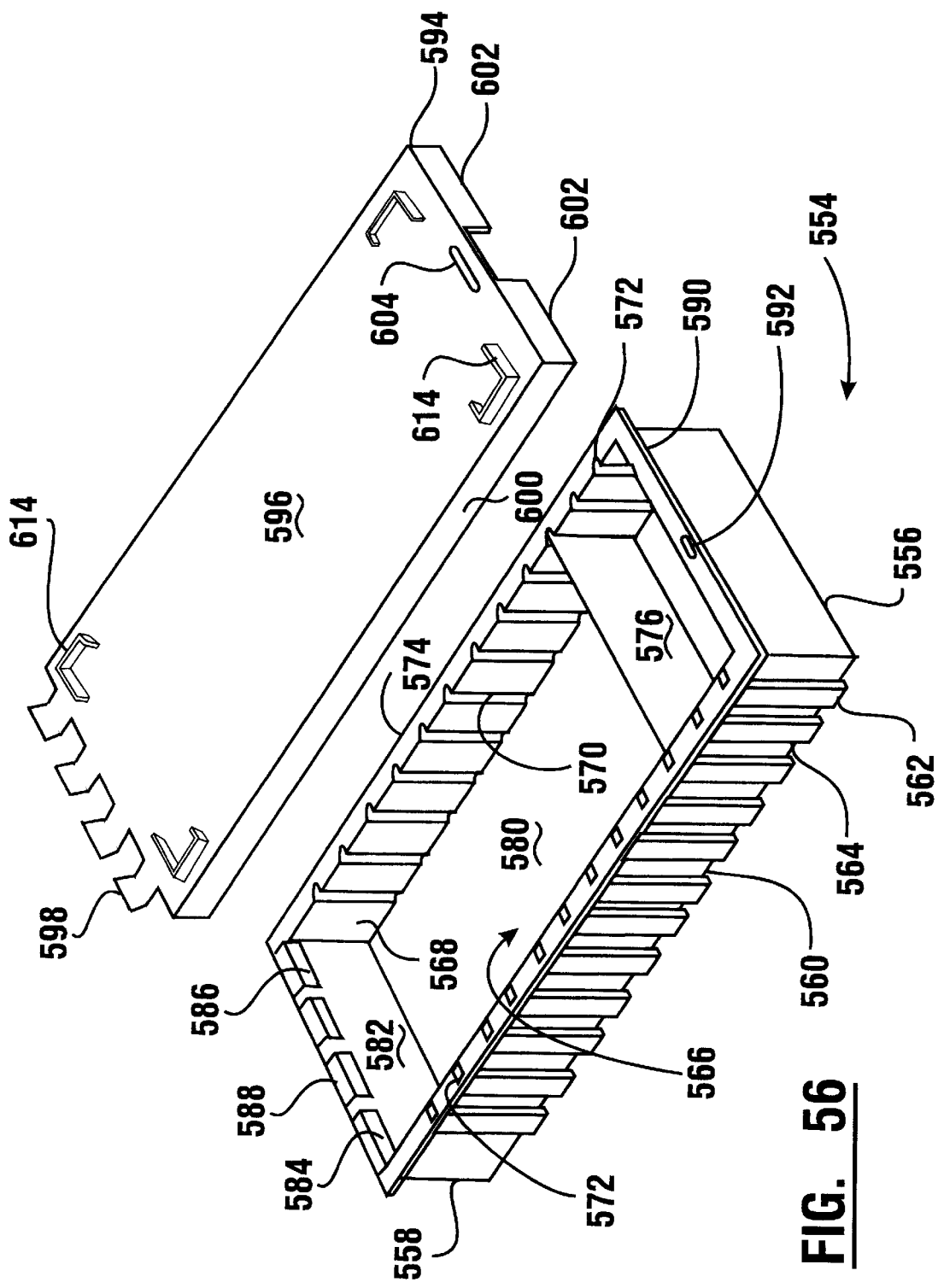
FIG. 56 is an isometric view of an embodiment of a removable liner and lid.

An embodiment of a liner used in carrying out the method is shown in FIG. 56. The liner generally indicated 554 is a portable container for housing medical items. The liner includes a front wall 556 and a back wall 558. The liner also has a pair of side walls 560. The side walls 560 include a plurality of spaced projections 562. Apertures 564 extend between adjacent projections on the exterior of the side walls.

The walls of the liner bound an interior area generally indicated 566. The interior area is bounded by a pair of opposed inside walls 568. The inside walls 568 include spaced slots 570 therein. The positions of the slots correspond to the projections 562 on the side walls 560.

Figure 58:
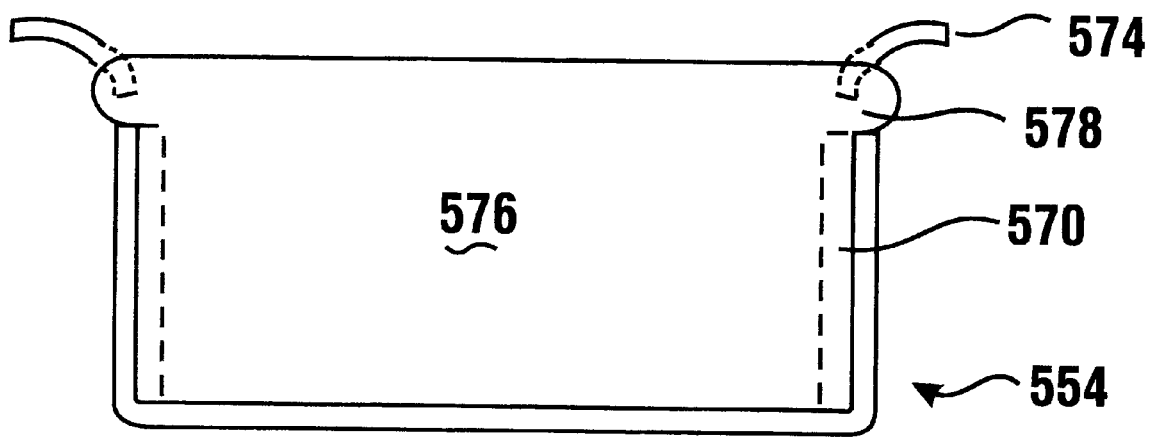
FIG. 58 is a transverse cross sectional view of a removable liner and a divider installed in the removable liner.

At the top of each slot 570 are openings 572. Each of the side walls includes an outward extending flange portion 574. The openings 572 extend entirely through the side wall and a portion of the flanges 574. As shown in FIG. 58, dividers 576 are enabled to be selectively installed in the interior area 566 of the liner. The dividers 576 are generally rectangular members with outward extending ears 578 adjacent the top thereof. The liner 554 and the dividers 576 are preferably comprised of relatively flexible plastic or other material that enables sufficient deformation so that the dividers may be manually installed in the slots 570. The installation of the dividers enables selectively dividing the interior area 566 of the liner into multiple compartments. The dividers 576 may have bar code or other indicia installed thereon for purposes that have been previously discussed. In addition the interior area 566 of the liner includes a floor 580. Bar code or other indicia may alternatively be installed on the floor of the liner.

Figure 59:
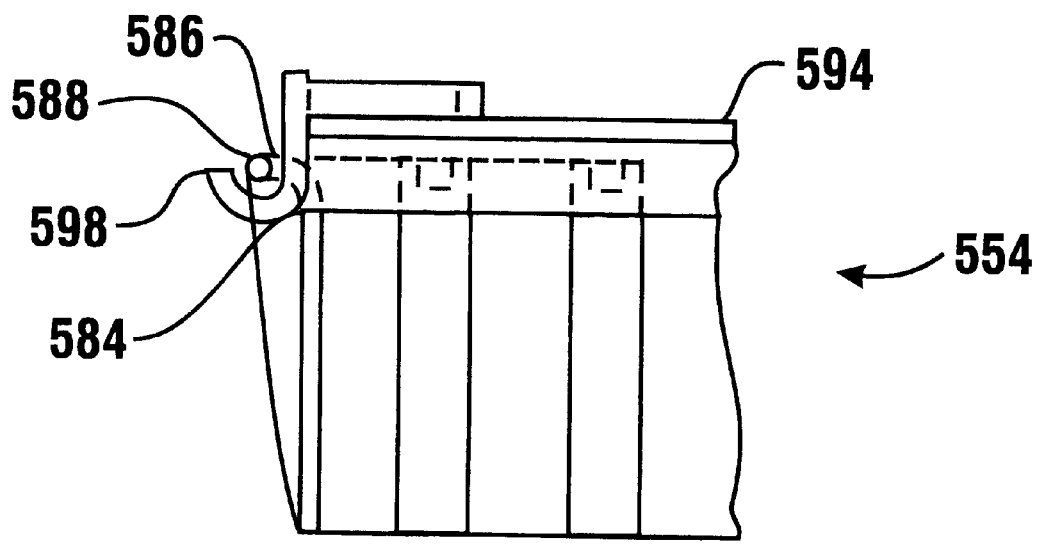
FIG. 59 is a side view of a first end of a liner and an engaged lid including the engaged hinge parts thereof.

The interior area 566 of the liner 554 is bounded by a back wall 582. The back wall has a plurality of hinge access openings 584 extending therethrough. Supporting projections 586 extend between the hinge access openings and support a pivot portion 588 thereon. As best shown in FIG. 59 pivot portion 588 is a generally round portion in cross section which serves as part of a hinge portion for holding a lid to the liner in a manner hereinafter discussed. The liner 554 further includes a front wall flange 590. Front wall flange 590 has an opening 592 therethrough the purpose of which is later explained.

Liner 554 is releasibly engageable with a lid 594. Lid 594 has a generally planar top surface 596. The lid 594 is preferably comprised of transparent plastic material. A plurality of fingers 598 extend from a first end of the lid. As best shown in FIG. 59, the fingers 598 are curved members which are sized to extend through hinge access openings 584. Fingers 598 are configured so they are movable in the hinge access openings and enable the lid 594 to be is pivotally movable thereon. The fingers 598 are part of a second hinge portion which works in cooperation with the first hinge portion on the liner to releasibly engage the lid and liner together.

It will be appreciated from the foregoing discussion that the lid 594 is engaged to the liner 554 by positioning the lid at an angle that is generally 90 degrees or greater relative to the floor 580 of the liner. In this position the fingers 598 may be extended through the cooperating hinge access openings 584. The liner 594 is then rotated to generally cover the interior area 566 of the liner, in which position the engagement of the fingers 598 and the pivot portion 588 hold the lid and liner in engaged relation at the first end of the liner.

The lid 594 further includes side wall flanges 600. Side wall flanges 600 extend generally the full length of the liner along each side wall (see FIG. 61). The side wall flanges are configured so that they overlie the side wall flanges 574 of the liner when the lid is in the closed position thereon. The lid 594 further includes a pair of spaced downward depending front wall flanges 602. The front wall flanges generally extend downward and in overlying relation relative to the front wall flange 590 on the liner. A front lid opening 604 extends through the planar top portion 596 of the lid. The front lid opening is generally aligned with opening 592 in the front flange of the liner. When the lid is positioned in covering relation to the liner the space between the front wall flanges 602 on the lid generally corresponds to the position of the front lid opening 604.

The aligned openings 604 and 692 in the lid and liner respectively, enable the end of the liner and lid opposite fingers 598 to be held in engaged relation with a lock device. In one embodiment of the invention the lock device comprises a tamper indicating seal generally indicated 606 in FIG. 60. The tamper indicating seal includes a strap portion 608. The strap portion 608 is preferably flexible and can be extended through the aligned openings 592 and 604. The strap portion preferably extends from a body portion 610 of the seal. The strap portion is doubled back and accepted into an aperture in the body portion 610. The aperture preferably includes one of a plurality of types of conventional one way locks. Such one way locks enable the strap portion to be extended through the aperture in one direction but prevent movement of the strap in an opposed direction. Once engaged the one way lock cannot be opened without breakage of the body portion or strap in a manner that would be readily apparent upon visual observation. In this manner the tamper indicating seal 606 provides a visual indication if sealed liners are opened.

The tamper indicating seals are particularly valuable when the liners are transported by entities other than those who have the responsibility for loading them or unloading them into the storage locations. A restocking user who receives a liner with a damaged tamper indicating seal would likely be aware of the problem and can report a possible improper occurrence.

It should be understood that while one embodiment uses a strap type tamper indicating seal as a locking device, in other embodiments other types of locking devices may be used. Such locking devices may include key type or other types of locks that have components permanently associated with either the lids, the liners or both.

Figure 60:
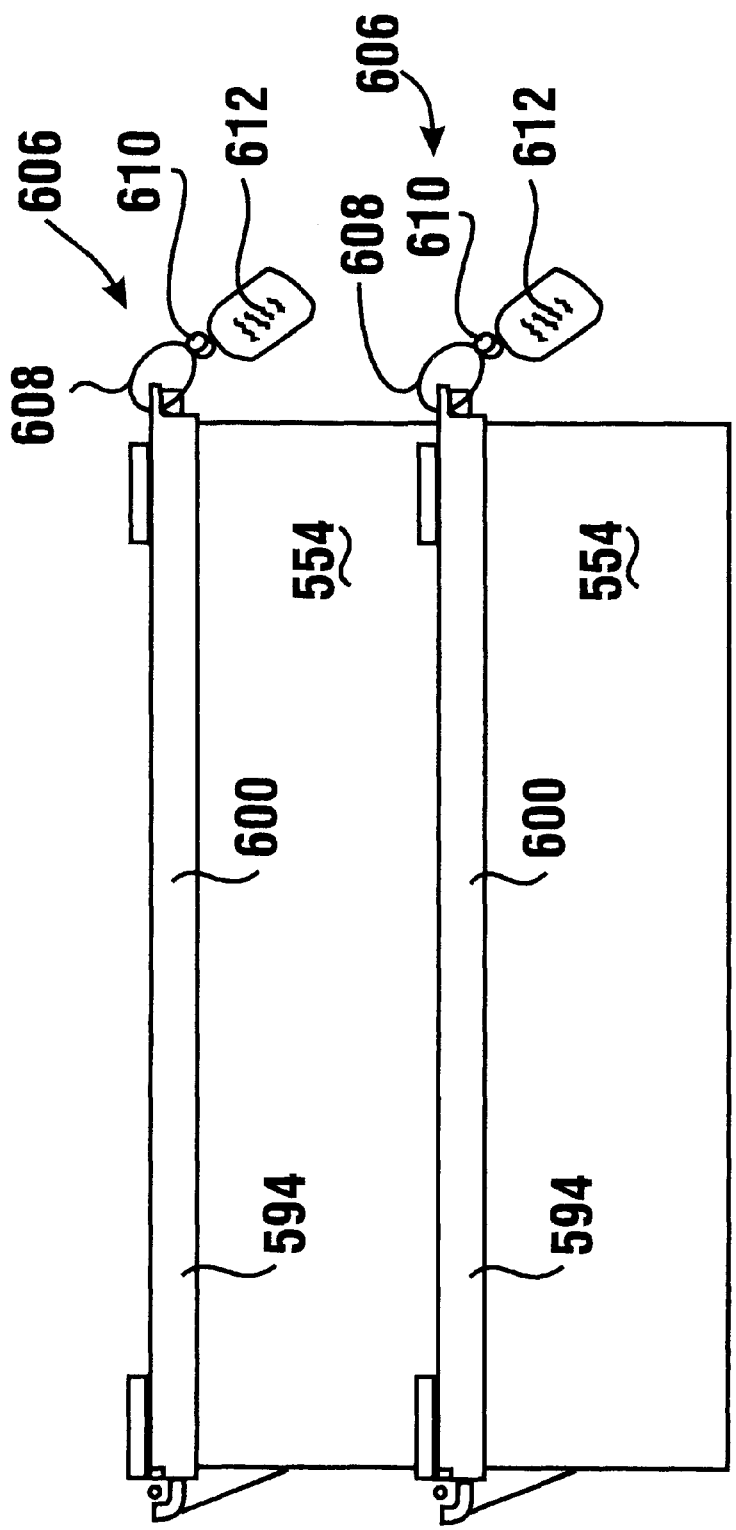
FIG. 60 is a side view of a pair of liners and lids shown in stacked relation.

As shown in FIG. 60 one preferred form of the tamper indicating seal 606 has a label tag 612 connected thereto. Label tag 612 is preferably sized and configured for having machine readable indicia thereon. Such machine readable indicia includes in the described embodiment a bar code label which identifies the storage location and/or medical item in the liner. In alternative embodiments label tags may be placed on other areas of the lid or liner. Other forms of the invention may have generally permanent indicia on the lid or liner.

In alternative embodiments other types of indicia may be used. Such indicia may include for example other types of optical indicia like computer chips, programmable displays or other devices which can be used to identify the liner or the contents thereof. Other embodiments may use alternative forms of information recording devices including those which are permanently attached to the liners or lids or both.

Figure 61:
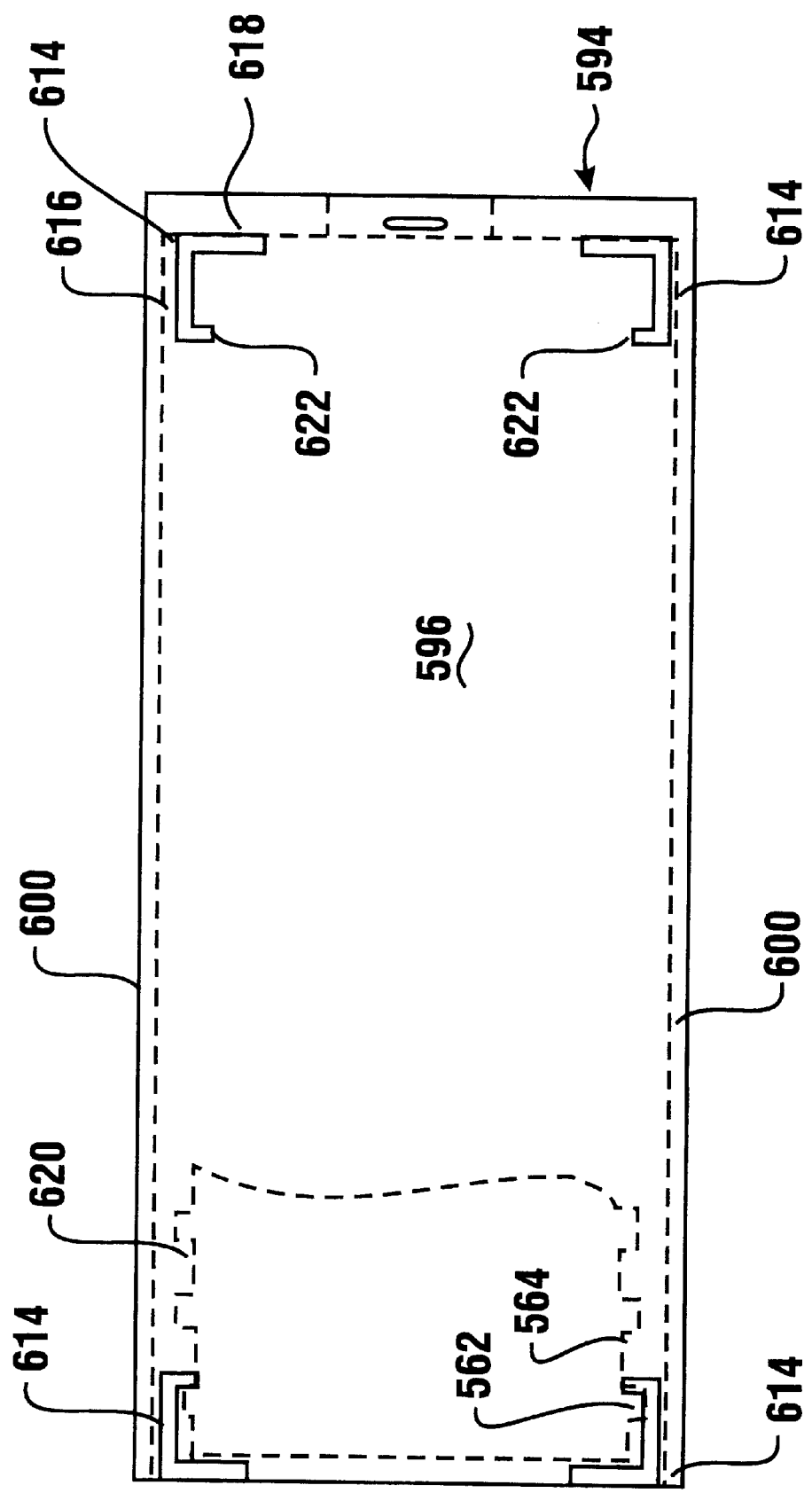
FIG. 61 is a top plan view of a lid with a portion of an overlying liner shown thereon in phantom.

As shown in FIG. 56 lid 594 includes four projection segments 614 thereon. The segments each include two generally perpendicular wall portions 616 and 618. As shown in FIG. 61 the wall portions are generally arranged at the corners of a rectangle. The rectangle which is bounded by the segments generally closely conforms to a lower portion of the liner. The profile of the lower portion of an adjacent liner generally indicated 620, is shown in phantom in FIG. 61. The close conforming contour of the interior surfaces of the walls of the segment and the lower portion of the liner enable the liners to be readily stacked when the lids are installed thereon as shown in FIG. 60. This feature restricts relative movement of the stacked liners during transport.

To further restrict relative movement of the liners, wall portions 616 which extend adjacent to the outer side walls 560 of the adjacent liner, include finger projections 622 thereon. As shown in FIG. 61 the finger projections 622 extend inward relative to an adjacent liner. The finger projections 622 extend in an aperture 564 of an adjacent liner. At least one of the projections 562 of the side wall is adjacent to the finger projection when a liner is positioned in supported relation on the lid.

The preferred configuration of the segments provides for a snug releasable engagement between a lid and an adjacent liner installed thereon. An adjacent liner is not only held in nested relation between the four segments 614, but is also held at each end by engagement of the finger projections 622 with an adjacent projection 562 on the outer walls of the liner. This configuration enables the liners with the lids installed thereon to be stacked in generally secure nested relation. It also prevents the liners from moving relative to one another while they are being transported. Liners with engaged lids may be stacked two, three and more high, depending on the size of stack that can be easily handled. However when the liners reach an area adjacent to the storage locations the liners may be readily disengaged.

The configuration of the segments of the preferred embodiment also enables the stacking of liners having different sizes. For example, a liner may be sized to include a bottom portion that has a profile that is similar in width but shorter in length than the liner just described. The exterior of such a liner includes apertures similar to the liners shown. This configuration enables holding the liner having the shorter bottom profile with the finger projections at only one longitudinal end of the liner. This limits shifting during transport of liners that have different sized lower portions. In addition, liners having a shorter lower portion profile may be selectively engaged in stacked relation with the finger projections on either longitudinal end of an adjacent lid.

In one form of the invention different sized liners are configured to be used with generally identical lids. For example, a deeper liner may be provided with a top opening that is configured to accept the lid used with a shallower liner. Other deeper liners may have an opening sized to accept identical lids, but may have a shorter lower profile so as to engage only finger projections on one longitudinal end of an adjacent lid when in stacked relation. Other configurations for liners may be made within the scope of the invention to suit the requirements of varied types of dispensers and storage locations.

Figure 57:
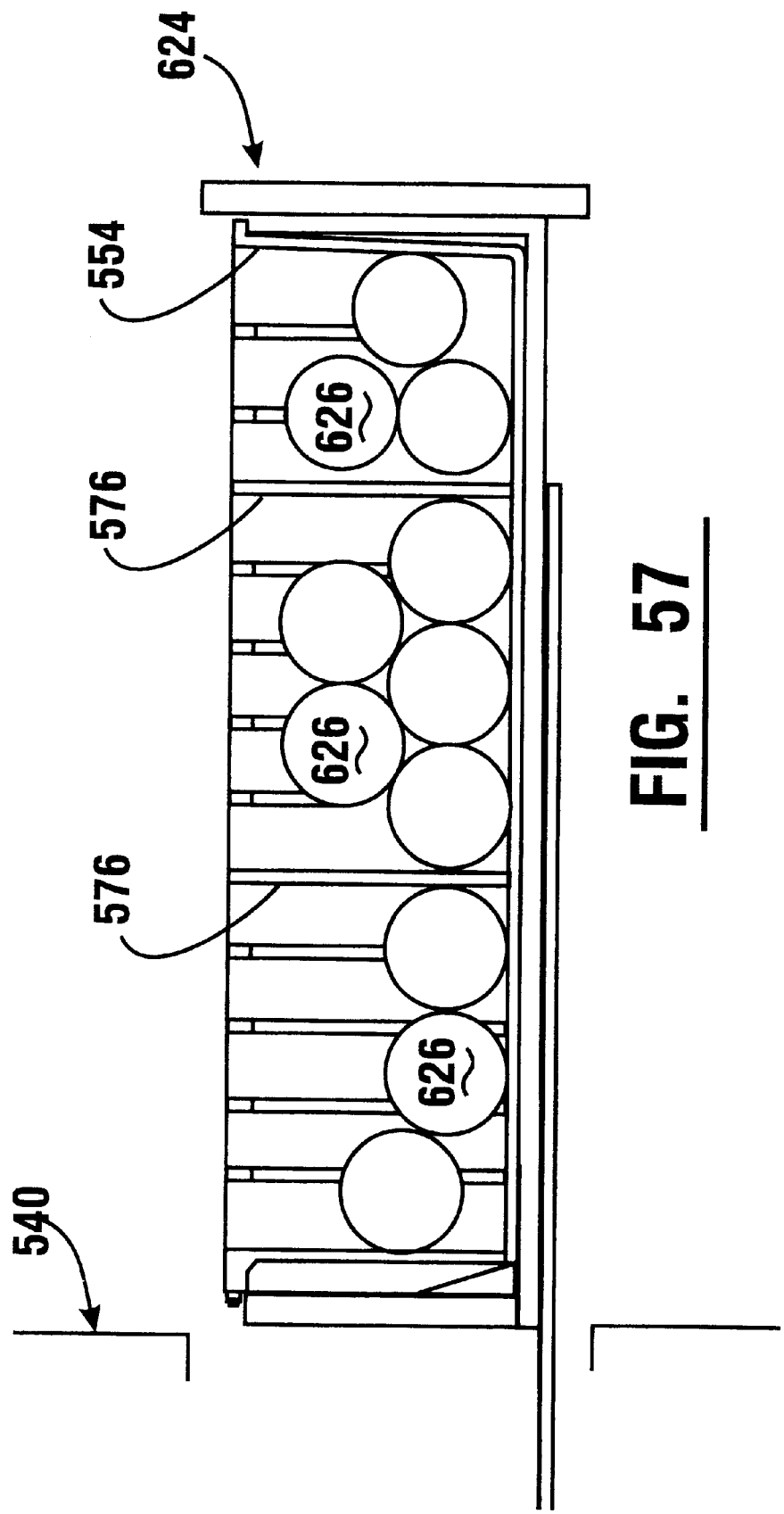
FIG. 57 is a side cross sectional view of a drawer in an electronic lock drawer module, shown in an extended position shown with a removable liner installed therein.

As shown in FIG. 57 the liners are preferably configured to be accepted in the storage locations where medical items are held. In FIG. 57 a drawer 624 of a dispenser device such as a lock drawer module is shown in the open and extended position. The drawer 624 has a storage location that is configured to accept the liner 554 therein. The storage location and the liner are preferably configured so that the liner fits snugly in the storage location. The liner however is preferably readily removable from the storage location so that a substitute liner may be placed therein.

When the liner 554 is placed in the storage location and prior to the operation of the system, the lid 594 which covered the medical items in the liner during transport is preferably removed. The lid may be removed in some embodiments after the liner has been installed in the storage location. In other embodiments the lid may be removed prior to installation of the liner. The time when the lid is removed may depend on the particular type of storage location involved and the preferences of the restocking user. However as represented in FIG. 57, before the system is operated the lid should be removed from the liner so that medical items such as item 626 in the liner may be accessed or otherwise appropriately dispensed from the dispensing device.

In a preferred form of the invention the storage locations and liners are configured so that the liners can only be positioned in the storage locations in one orientation. This is useful for achieving a desired orientation for the medical items, as well as to achieve a standardized procedure for opening the liners and for orienting machine readable indicia that is positioned on the liners. Further in some circumstances different types of medical items may be positioned within a liner, for example in different compartments. The requirement that the liner may only be installed only one way helps to assure that medical items are presented in a desired order.

It should be appreciated that while a liner suitable for use in connection with an electronic lock drawer type dispenser device is shown, in other embodiments other types of liners or transportable containers for holding medical items may be used. These may include liners suitable for use in other types of dispensers as well as liners suitable for use in open type storage locations. The described approach of labeling the liners with indicia of the bar code type is exemplary, and other embodiments of the invention may employ other types of either permanent or temporary indicia for identifying the storage locations and/or the type of medical items held in the liners.

The steps in the method executed using the liners is further explained with reference to FIG. 55. In the stocking location 550 the liners are filled with the appropriate types of medical items and the lids are installed thereon. This step is schematically represented by a liner 628. At the stocking location the liners are preferably labeled with indicia which are indicative of the storage locations in which the liners may be installed. As previously discussed this indicia may take the form of a bar code label which indicates the type of medical item placed in the liner. Alternatively the indicia may be indicative of a particular storage location or may be a combination of location and item information. The bar code indicia may be placed on the label tag of a tamper indicating seal or on the liner, the associated lid or both. Alternatively the liner may have a generally permanent label and data correlating the type of medical item stored in the liner may be input through an input device and stored in a data store.

The filling of liners at the stocking location is preferably done in accordance with the restock reports 553. The restock reports are preferably produced by the report generating device based on information stored in the data store concerning which storage locations require replenishment. The restocking report may include removable labels which are applied to the liners.

Because the restock report preferably includes both human readable as well as machine readable indicia, the removal of labels therefrom may still leave a useful report for use in connection with transporting and installing the liners in the proper storage locations. Other embodiments of the invention may have machine readable indicia on the restock report in addition to the removable labels. As a result the restock report may be used in connection with machine reading devices even after the labels have been removed therefrom. Alternatively the restock report and the labels may be generated separately. In embodiments where the liners have permanent indicia thereon the restock report may be generated by the computer based on the stored data indicating the medical items housed in particular liners. The computer may assign the liner to a storage location where medical items of the type held in the liner are required and indicate the locations in the report.

After the liners have been filled and preferably sealed with the lids at the stocking location, the liners are transported to the dispensing devices or other locations where they will be installed. This is graphically represented in FIG. 55 by a stack 650 of such liners. The liners and lids are stacked in releasibly engaged relation as many liners high as is convenient for handling. As previously indicated the liners are preferably transmitted to the storage locations along with the restock report 553 which indicates where the liners are to be installed. Alternatively the restock report may be reproduced on a printer connected to the system at the hospital ward or other facility where the liners will be installed in the storage locations.

Once the liners are moved to the appropriate storage locations a user operates the appropriate display terminal 538, reading device 542 or other apparatus for accessing the storage locations. This is preferably done in the case of the dispenser device 540 by opening the dispenser device so that an interior area thereof may be accessed. In one form of the invention this is done by the restocking user logging onto the display terminal 538 in the manner previously described, and providing appropriate inputs to indicate that they are going to conduct a restock activity. The restocking user after appropriately logging into the reading device 542 may then read the indicia associated with the liner to be installed. This information is transmitted from the reading device to the display terminal which operates to determine from the nature of the indicia the location where the liner should be installed. This is accomplished for example by comparing the type of medical item represented by the indicia on the liner to information stored in the data store. The processor connected to the data store determines where medical items of the particular type held in the liner are stored in the storage locations adjacent the display terminal. The processor then operates to open or otherwise make accessible the particular storage location where those medical items are stored. In this example this is accomplished by opening the appropriate drawer in the electronic lock drawer module where the liner will be installed.

It should be understood that in alternative embodiments the indicia labeled on the liners may be directly representative of the storage location where the liner is to be installed. In other alternative forms of the invention or in circumstances where the particular medical item to be restocked is not readily labeled with such indicia, a restocking user may read the indicia off the restock report 553. Reading the indicia off the restock report may also cause the appropriate storage location for the corresponding item to be made accessible to the restocking user.

After the storage locations for the medical items housed in the liner are made accessible, a previously installed liner is moved from the storage location and the new liner is installed. Alternatively once a liner has been removed from a storage location the restocking user may scan the location indicia associated with the storage location with the reading device. This may involve for example scanning indicia in the storage location in the dispenser device where the liner is to be installed. The indicia may be on a wall bounding the storage area which accepts the liner therein or in another convenient location. Alternatively such indicia may be on the face of a drawer in an electronic drawer module. Location indicia may be provided on a shelf such as a shelf in a refrigerator or cabinet controlled by a lock or on an open shelf which supports the liner in an open storage location.

When the indicia is read from the storage location with the reading device the information read from the liner is compared to the information read from the storage location to determine if the location is an appropriate location for that type of medical item. This may be done directly by the processor within the reading device comparing the data read from the label tag associated with the liner to the location indicia. Alternatively information from the reading device may be transmitted to the display terminal which then operates to determine if the location where the liner is to be installed is appropriate. If it is determined that the restocking user may be installing the liner in an improper location, a signal is given to the restocking user. This helps minimize the risk that restocker will place the medical items in improper storage locations.

The process of scanning the indicia associated with the liner, scanning the indicia associated with the storage location and replacing the previously installed liner with the new liner is repeated for each storage location where replenishment is required. It should be understood that in embodiments of the invention the scanning of the indicia associated with the new liner and the storage location may be done either before or after the existing liner is removed and the new liner is installed therein. The order of the steps may vary based on the nature of indicia and the personal preferences of the restocking user.

The transparent lids enable machine readable indicia applied inside the liner to be read with the lid installed. The transparent lids also enables visual observation of the contents of the liner which saves time and reduces the risk of error.

Either before or after installing a new liner in a storage location, the tamper indicating seal is broken and the lid is removed so that the medical items in the liner become accessible. This step is represented schematically in FIG. 55 by liner 632. After the interior area of the newly installed liner is made accessible, medical items from the previously installed liner may be counted by the restocking user and transferred to the newly installed liner. The number of items transferred is preferably input to the system by the restocking user using the reading device 542 in the manner similar to that previously described. This transfer of medical items from the previously installed liner to the newly installed liner is represented by liner 634 in FIG. 55.

In alternative embodiments of the invention the previously installed liner including the medical items which remain therein may be returned to the stocking location for audit. Such medical items may also be reviewed to determine if their expiration date has passed or if for some other reason they should not be reused. In these circumstances the lid removed from the newly installed liner may be installed on a previously installed liner and engaged thereto with a tamper indicting seal. This is represented in FIG. 55 schematically by a liner 636.

When the previously installed liners are to be returned to the stocking location with the lids installed thereon they may be stacked in nested relation in the manner previously described. This is schematically represented in FIG. 55 by a stack 638 of such liners. Alternative forms of the liners and lids may be configured to stack in nested relation when empty. When the medical items have been removed from such alternative liners, the liners and lids may be segregated or stacked randomly in the manner represented by stack 640. It should be understood that in situations where the liners are returned with medical items therein the tamper indicating seals which hold the lids in engagement with the liner may include numbers representative of the restocking user who sealed them in the storage location or other information that enables tracking of where they originated. Alternatively in situations where indicia was printed on the lid of the new liner that was installed in the storage location this indicia may now become associated with the previously installed liner at that location and an indication thereof stored in the data store based on inputs from the restocking user.

When previously installed liners are returned with medical items therein an audit is conducted at the stocking location of the medical items. To do this the returned liners are opened as indicated schematically by a liner 642. The medical items are counted and the number compared to the information input by the restocking user. Of course if there is a discrepancy or a liner is returned with the return tamper indicating seal broken the possible problem may be promptly investigated.

Medical items removed from a returned liner may be inspected for their suitability for further use. If the items are not suitable for reuse they may be discarded. If the items are suitable for reuse they may be returned to inventory or immediately placed into another liner.

At the restocking location tags which are indicative of storage locations for particular medical items held in liners may be removed. Alternatively, other devices for storing information, such as memory chips on the liners, may be cleared. This enables the liners and lids to be used to hold other types of medical items which are destined for storage in storage locations other than the one from which the liner was removed.

The medication dispensing system of the present invention may be used in connection with a plurality of different types of devices which store and dispense medical items. For purposes of narcotics, which are tightly controlled, a medicine dispenser which holds the medical items in a secure enclosure prior to dispense and which dispenses such items in a manner that can be controlled and confirmed is preferred. Medicine dispenser 100 is such a dispenser that is used in connection with dispensing medications. A further example of a suitable dispenser is shown in co-pending U.S. application Ser. No. 60/045,137 filed Apr. 30, 1997, the disclosure of which is incorporated herein by reference. U.S. application Ser. No. 08/879,997, filed Jun. 20, 1997 and claiming priority to provisional application No 60/045,137, has issued as U.S. Pat. No. 6,019,249.

Figure 27:
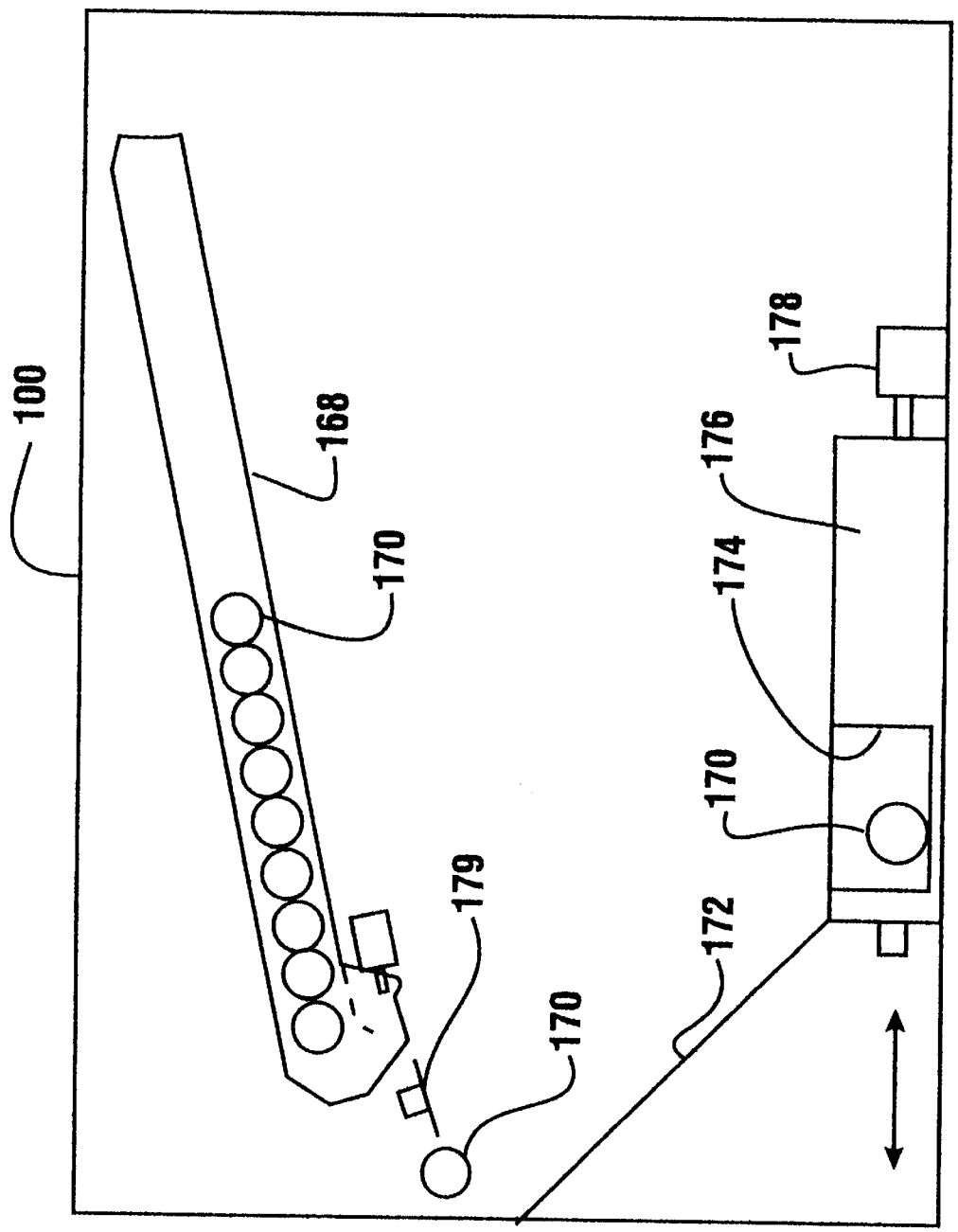
FIG. 27 is a sectional side view of the dispenser mechanism shown in FIG. 14 located inside a medicine dispenser.

The interior of medicine dispenser 100 is shown schematically in FIG. 27. Dispenser 100 encloses a plurality of dispenser magazines 168 only one of which is shown. Each magazine holds a plurality of ampules, vials or other medication holding containers 170 which are held in inclined relation in the magazine. Each of the containers in a particular magazine contains a predetermined dose of a substance such as a narcotic material that may be prescribed to a patient. Many forms of cylindrically packaged medications or medical items may be held in the magazines. Medicine dispenser 100 optimally houses a large number of magazines, each one holding vials with a particular type of medicine. Each magazine 168 includes a dispensing mechanism later described in detail that releases containers in response to electrical signals one at a time from the lower end of the magazine. Released vials are guided on a chute 172 into a pocket 174 in a drawer 176. Drawer 176 may be a simple drawer or in alternative embodiments may be controllably locked and unlocked by an electronic lock 178 shown schematically inside the medicine dispenser. Each magazine has a dispense verification sensor 179 associated therewith. Sensor 179 is operable to detect the actual dispense of a container from a magazine. Sensor 179 may be an optical, mechanical or other suitable sensor type.

When medicines are requested at the display terminal 102, the appropriate containers from the magazines 168 are released and fall down the chute into the pocket 174. After the vials have been released and are in position in the pocket, they may be taken. In alternative embodiments in which the drawer is controlled, the data terminal 102, in response to signals from the computer 84 unlocks the electronic lock 178 and enables the drawer 176 to be pulled outwardly so that the containers in the pocket may be taken.

Replenishment of the medicine dispenser 100 is accomplished by manually replenishing the magazines and indicating that fact through the data terminal in the manner previously described. To accomplish this the medicine dispenser has to be opened. This is possible only under the most secure of circumstances and through the use of a mechanical locking system comparable to that which is conventionally used to secure narcotics. Normally, two keys are required to open the unit and each key is in the possession of a different person.

The operation of the dispensing mechanism is shown in greater detail in FIGS. 14 through 26. FIG. 14 shows the vials or other containers 170 in the magazine 168. As shown in FIGS. 15 through 17 because the magazine is tilted downward the containers tend to roll towards the front of the magazine toward an opening 180. The container adjacent the opening 180 contacts a guide 182 which is dog-legged in cross section. Guide 182 includes a tapered face 184 which is engaged by the first container 202 in the magazine. Guide 182 further includes an arm portion 186 that extends longitudinally adjacent the vials. Arm portion 186 has attached adjusting pins 188 which extend through the side walls 190 of the magazine. Adjusting pins 188 extend in angled slots 192 and may be fixed at selected positions therein using nuts mounted on the pins or other suitable locking fasteners.

The movable mounting of the guide 182 enables the magazine to accommodate different diameter containers by moving the guide in the slots 192 to provide sufficient clearance for a container to pass onto the guide adjacent opening 180 but not so much clearance so that the vial can fall out the opening without the actuation of the gate members as later explained.

Figure 18:
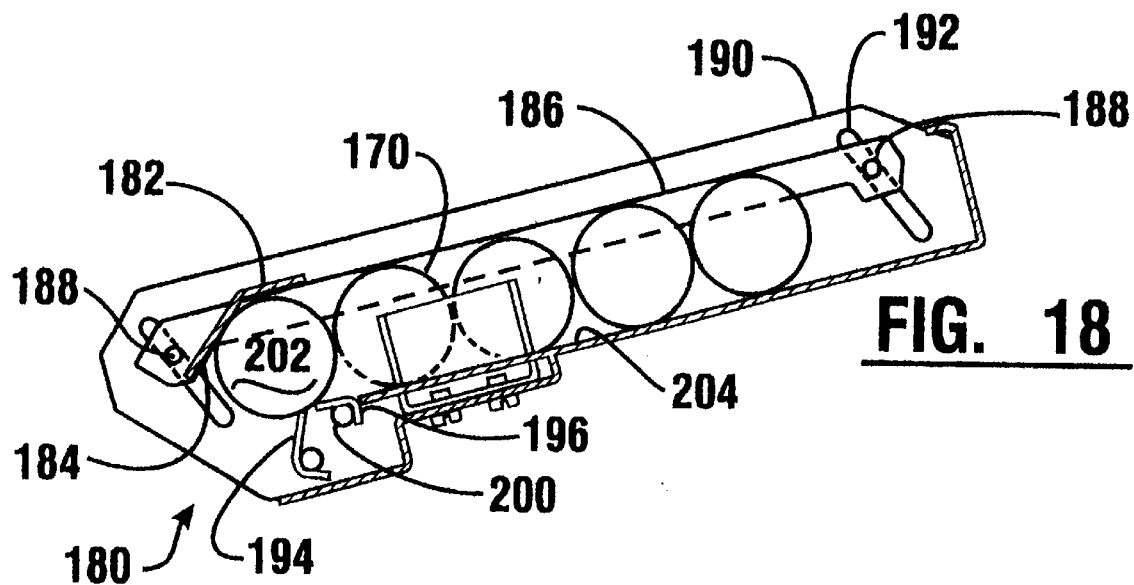
FIG. 18 is a cross sectional view corresponding to the dispenser as shown in FIG. 15.
Figure 19:
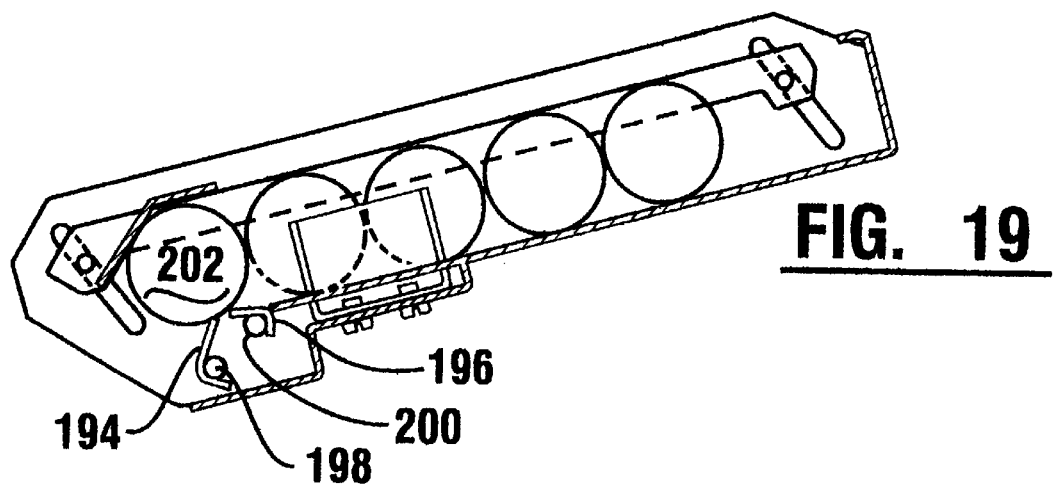
FIG. 19 is a side view of the dispenser mechanism corresponding to FIG. 16.
Figure 20:
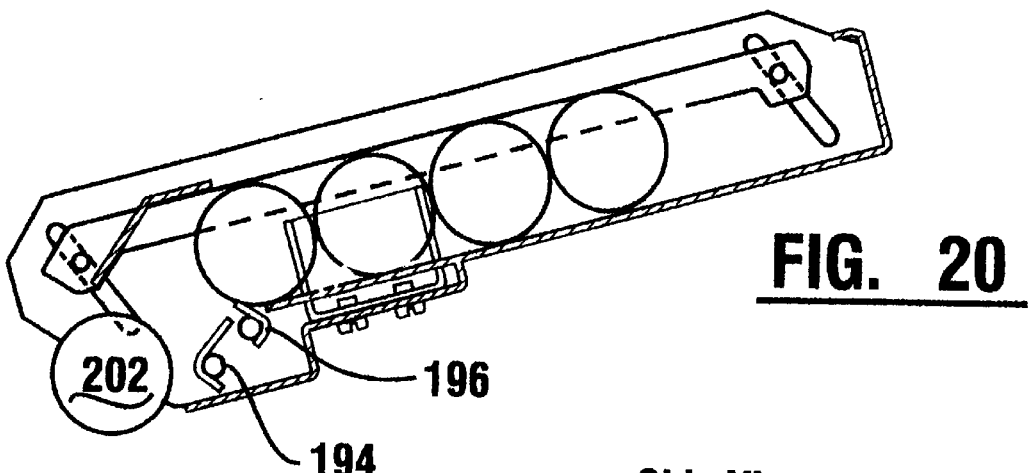
FIG. 20 is a side view of the dispenser mechanism corresponding to FIG. 17.

As best shown in FIGS. 18 through 20, a front gate 194 and a back gate 196 are mounted adjacent to opening 180. The front gate and back gate are mounted on a front gate shaft and a back gate shaft 198 and 200 respectively.

As shown in FIG. 18 in the inoperative position of the gate members front gate 194 engages the underside of first vial 202 adjacent opening 180. The end of front gate 94 engages container 202 at a position outward towards opening 180 from a location on the surface of the container diametrically opposite where container 202 engages tapered face 184 of guide 182. As a result, the container 202 is prevented from passing out through opening 180. In this position any force applied to container 202 (if it could be accessed) would tend to be resisted by compressive forces making it very difficult for the container to be manually removed. In the inoperative position of the magazine shown in FIG. 14 the back gate 196 has its upper end extending parallel to a bottom wall 204 of the magazine. As a result, in this position the back gate does not interfere with movement of the containers.

In the actuation sequence for dispensing a container, the back gate rotates in a clockwise direction to the position shown in FIG. 19. As it does this the back gate begins to move to a position blocking the container immediately behind container 202 in the magazine from moving toward the opening 180. In the position shown in FIG. 19 the front gate 194 remains in its original blocking position holding container 202 in the magazine.

After the back gate has begun to rise as shown in FIG. 19, the front gate begins to rotate in a clockwise direction toward the position shown in FIG. 20. As the front gate 194 rotates container 202 is no longer held in the magazine and passes out the opening 180. The back gate having fully rotated as shown in FIG. 20, holds the next container in the magazine from moving until the front gate returns to its original position shown in FIG. 18. When this occurs the back gate returns to its original position allowing the containers to roll forward and the next container is now in the position of container 202.

In the preferred embodiment of the invention, the slots 192 are oriented such that for any size container reasonably accommodated in the magazine, the front and back gates are positioned so that the front gate 194 may assume an over-center blocking position in the closed position and the back gate can move to prevent the dispense of more than one container at a time. This ensures that with each cycle of the front and back gates only one container is dispensed.

Figure 21:
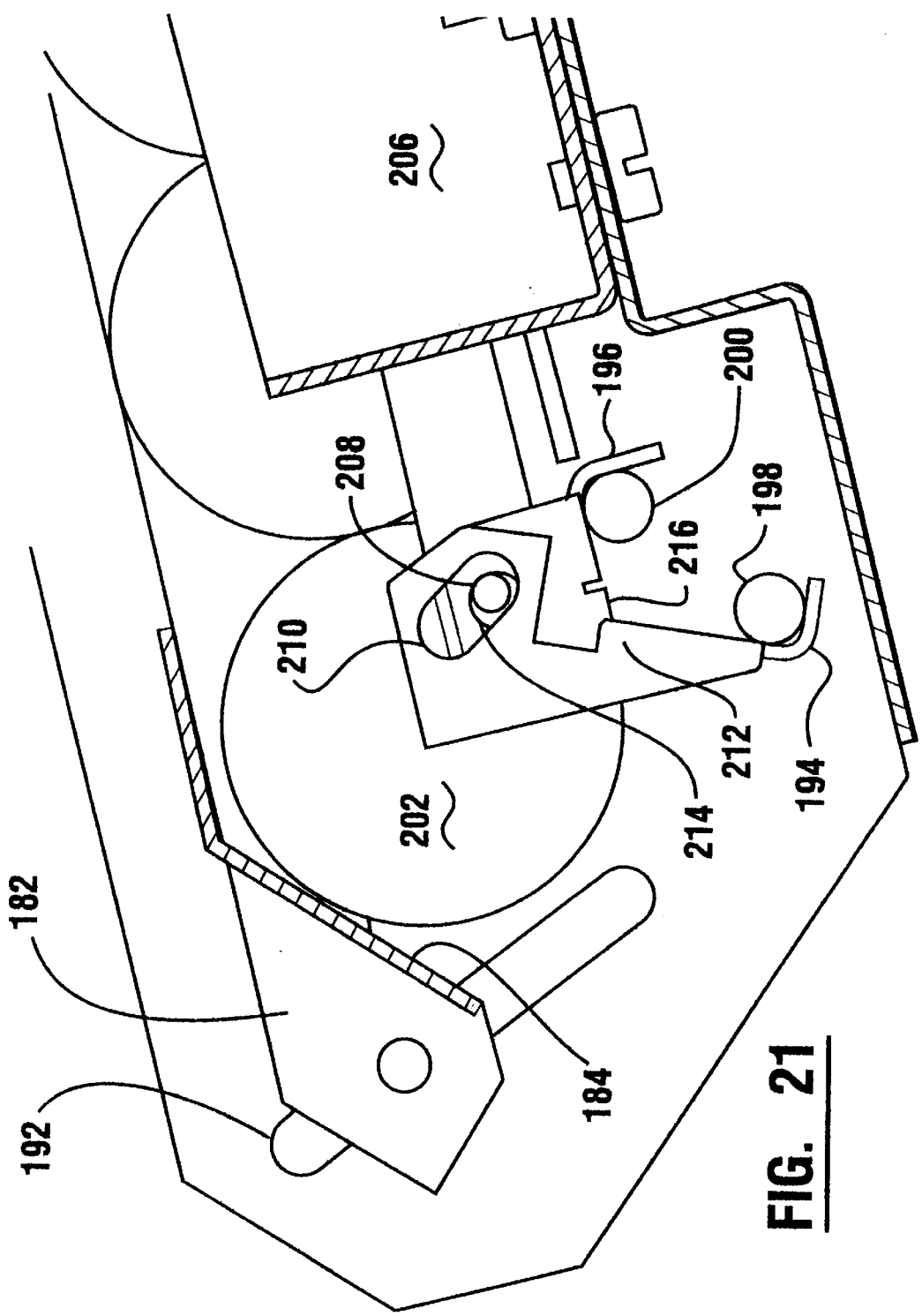
FIG. 21 is a side view of the dispenser mechanism and gate members in the positions shown in FIG. 15.
Figure 22:
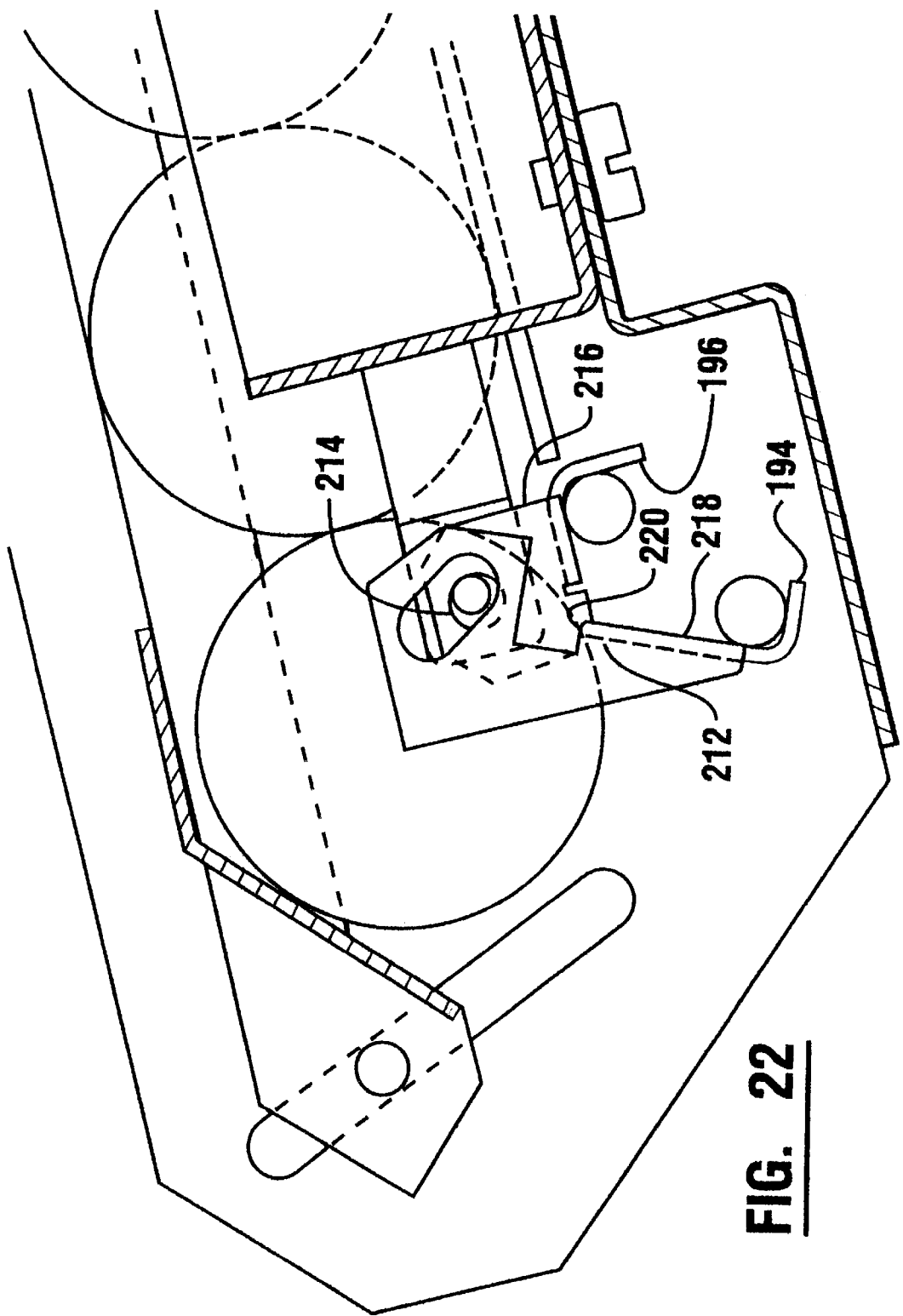
FIG. 22 is a side view corresponding to FIG. 21 including hidden edge lines.

The actuating mechanism for the front and back gates is shown in FIGS. 21 through 26. As shown in FIG. 21 the actuating mechanism for the gates includes an electrical solenoid 206. Solenoid 206 has an actuating plunger member with a pin 208 extending traversely therefrom. Pin 208 extends traversely in a first slot 210 in a first actuator plate 212 which is attached to the front gate 194. Pin 208 also extends through an opening 214 in a second actuator plate 216 which is attached to back gate 196. As best shown in FIG. 22 first actuator plate 212 has a traversely extending finger 218. In the position of the front gate shown in FIGS. 21 and 22, finger 218 engages a detent 220 in the second actuator plate 216. The purpose of detent 220 is to prevent finger 218 and front gate 212 from moving in a clockwise direction whenever the second actuator plate 216 is in its inoperative position as shown in FIGS. 21 and 22. This prevents a person who may gain access to the front of the magazine from being able to deflect the front gate so as to cause the containers to be removed from the magazine.

Figure 23:
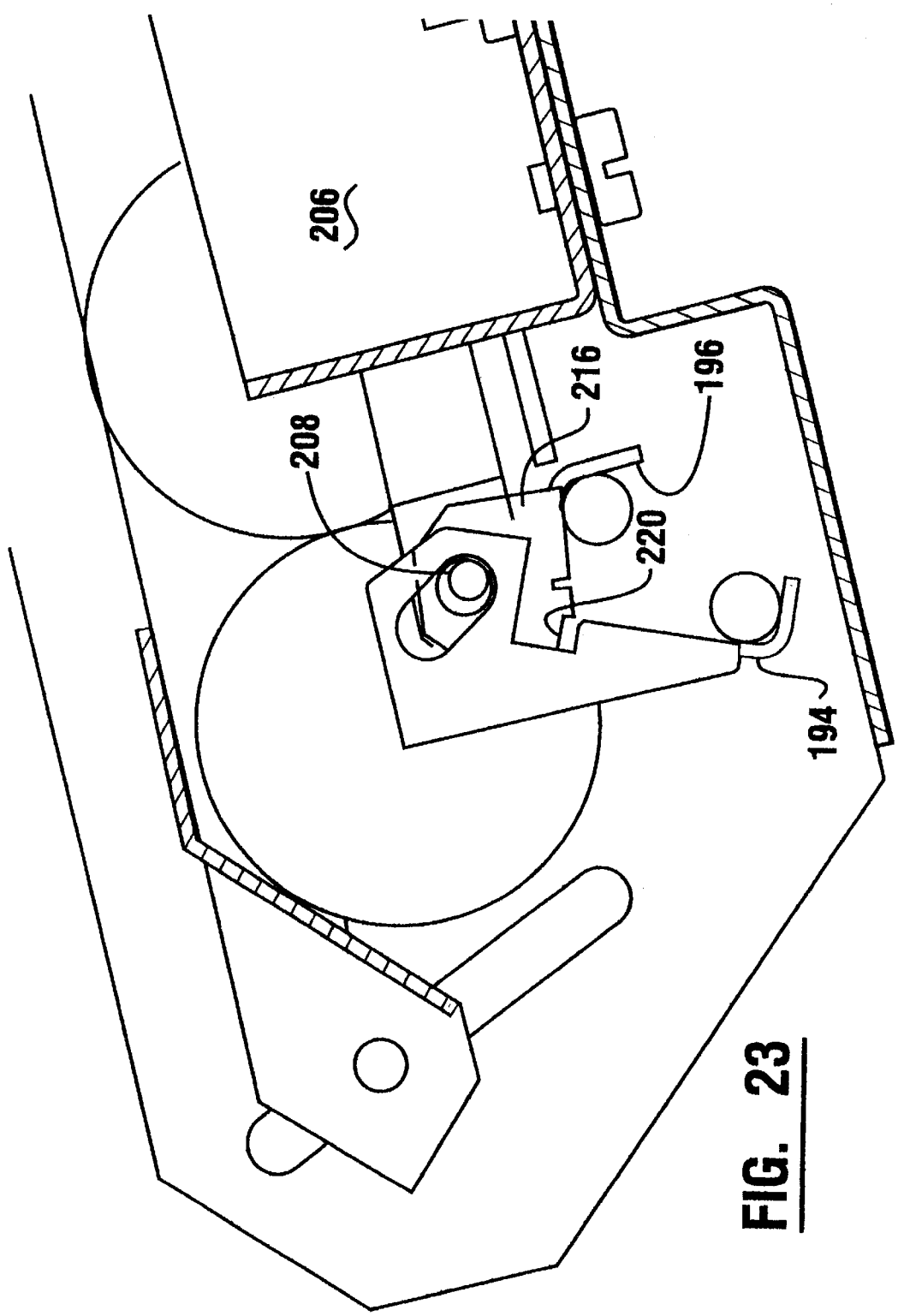
FIG. 23 is a side view of the dispenser mechanism with the gate members in the positions shown in FIG. 16.
Figure 24:
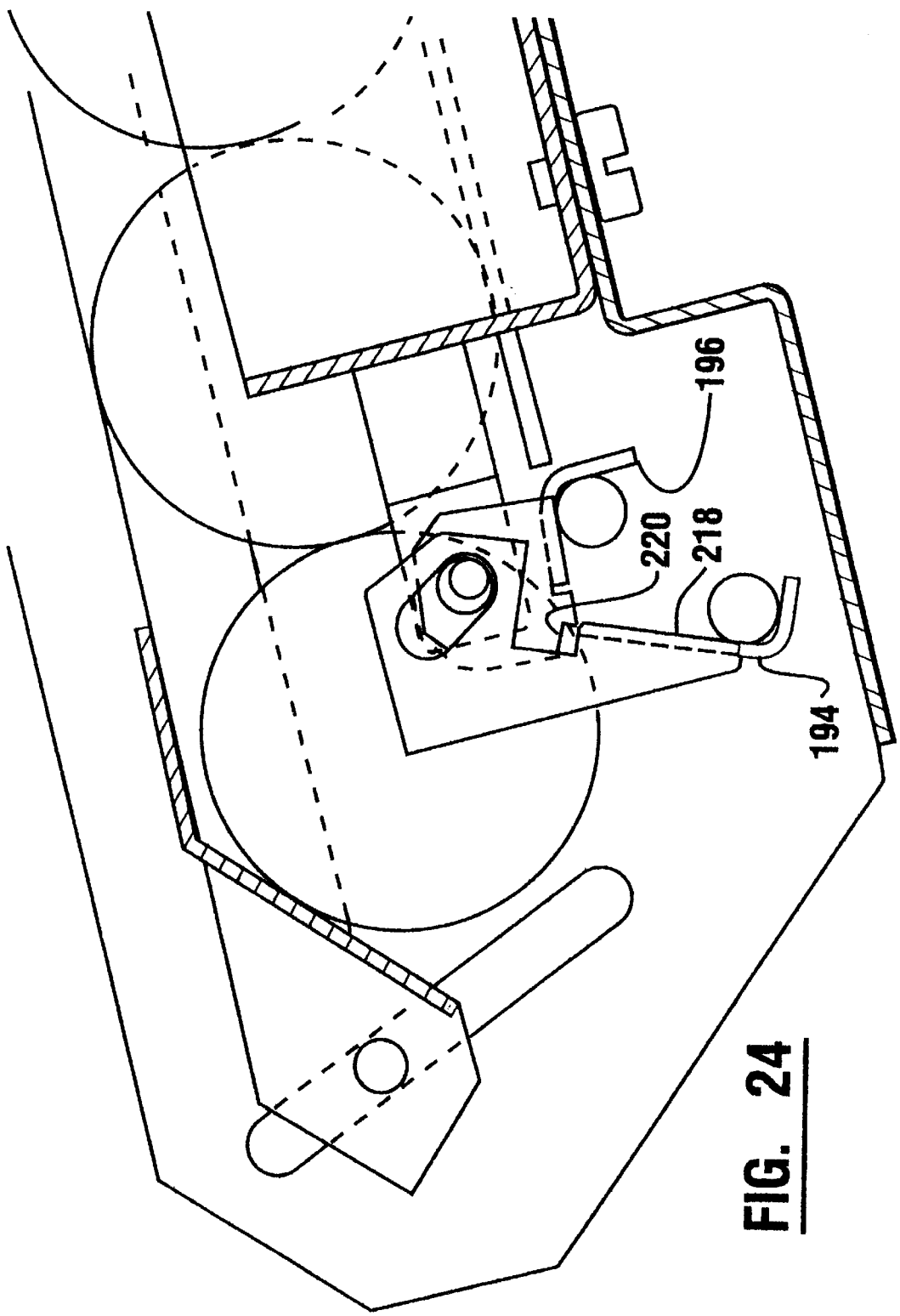
FIG. 24 is a side view of the dispenser mechanism corresponding to FIG. 23 including hidden edge lines.
Figure 25:
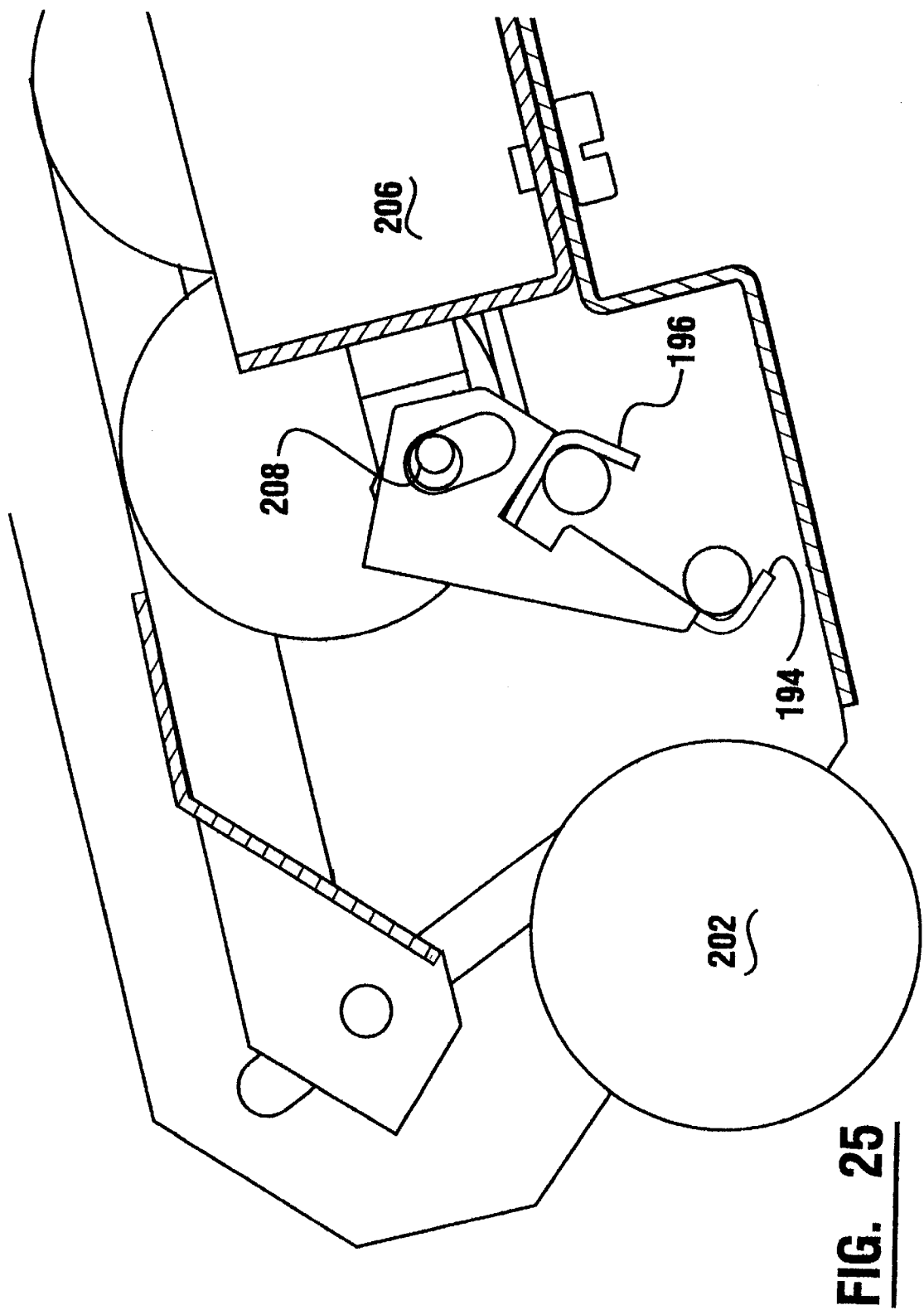
FIG. 25 is a side view of the dispenser mechanism with the gate members in the positions shown in FIG. 17.
Figure 26:
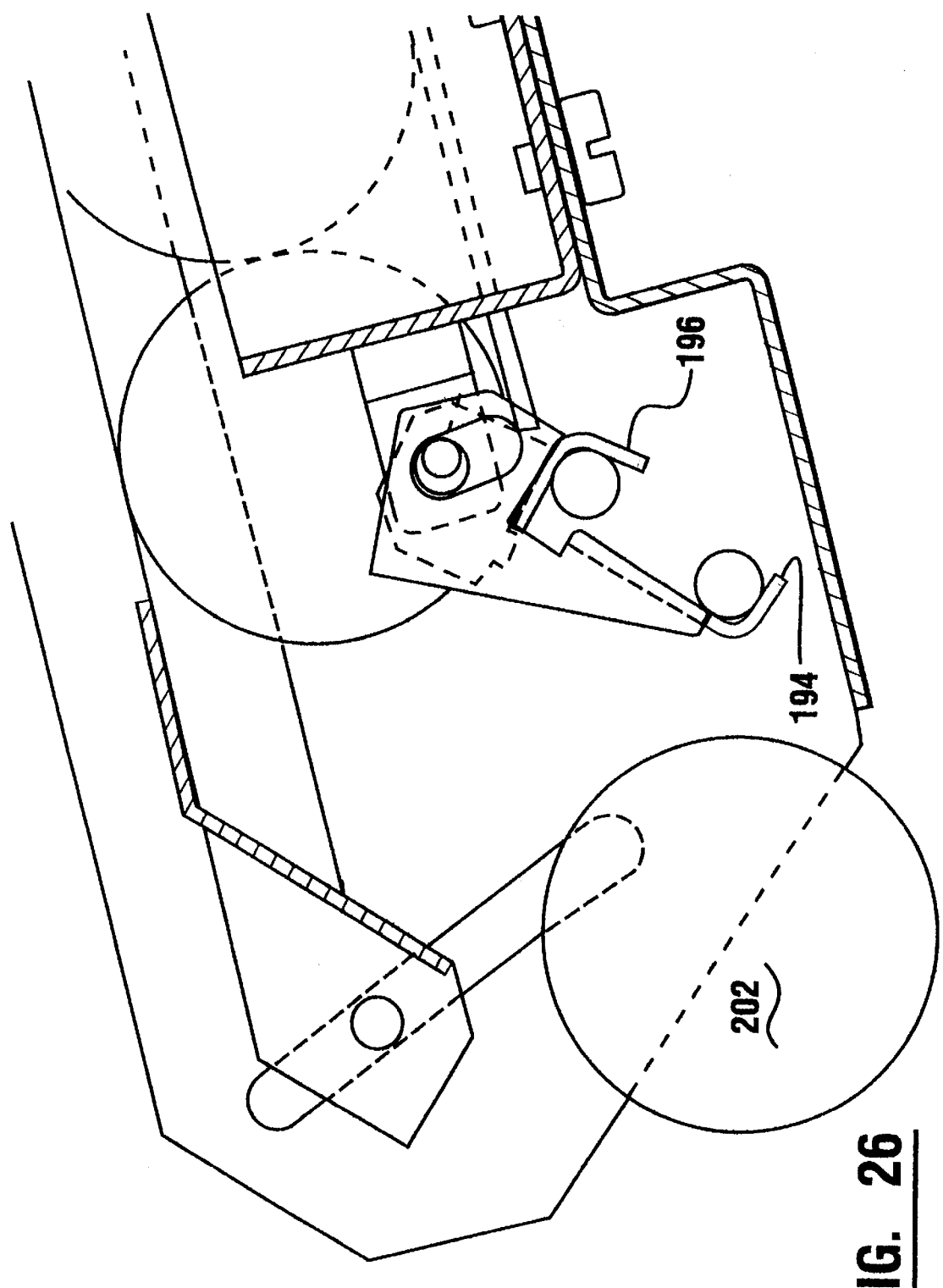
FIG. 26 is a side view of the dispenser mechanism corresponding to FIG. 25 including hidden edge lines.

As shown in FIGS. 23 and 24 the actuation of solenoid 206 by an electrical signal from the data terminal causes pin 208 to move second actuator plate 216 in a clockwise direction. This causes back gate 196 to move upward and detent 220 to disengage from finger 218. As a result, front gate 194 may move only after back gate 196 has risen so as to block the dispense of further containers. Upon further movement of pin 208 by solenoid 206 the front and back gate move to the positions shown in FIGS. 25 and 26. In these positions the front gate is rotated so as to release container 202 while the back gate is extended fully upward so as to prevent the discharge of the next container in the magazine. Thereafter, discontinuance of the electrical signal to solenoid 206 returns the gate members to their original positions and allows the next container to assume the position adjacent to the opening from the magazine.

The dispensing mechanism of the present invention enables the controlled dispense of one container at a time from the magazine in response to an electrical signal. This assures that only the requested medication is dispensed. The same magazine may be readily adapted to containers or items of varying diameter by adjusting the position of guide 182. The magazine also accommodates containers of different lengths. In addition, the gate members are suitably secure so as to avoid tampering by persons who might attempt to gain access to the interior of the medicine dispenser 100 through the dispenser drawer 176.

The dispensing mechanism also assures that the requested medical item has been dispensed. This is assured by using signals generated by sensor 179 to minimize the risk that a dispense will be recorded which has not actually occurred due to a malfunction. Circuitry in the dispenser is connected to the sensor 179 and transmits signals when a container passes out of a magazine. These signals are checked to see if they are generated when a signal to dispense to the corresponding magazine is given. The dispense of any item from a location and the provision of such item to a patient is only recorded in the computer data store when the dispense is verified by the sensor associated with the magazine. Alternatively, in other embodiments a bar code reader may be installed in the dispenser and bar code applied to the containers to verify not only the dispense but the type of item dispensed.

Although in the above described embodiment of the medicine dispenser the gate members are shown as extending the entire width of the magazine, in other embodiments the gate members may have other configurations and may be of different designs so as to extend only a portion of the width. Although in the preferred form of the invention the magazines extend in downward tilted relation in other embodiments they may be arranged to extend vertically. In such alternative embodiments guides may be provided to hold the containers adjacent to plate 204. Further, the containers may be dispensed in a vertically upward direction through incorporation of spring loading to bias the containers upward in the magazine. A fundamental aspect of the invention is that the gate member which corresponds to the front gate member engages the container in an over-center position with regard to where the container contacts the tapered face, and the back gate member moves in synchronized relation with the front gate member to prevent the dispense of more than one container at a time.

The system for monitoring and dispensing medical items which includes the hook registers, box registers, electronic lock drawer, refrigerator lock modules and medicine dispenser previously described may also include or be used with other types of devices. These may include automatic dispensing devices as well as manual devices for which the inventory and use information can be input as a matter of practice at a conveniently located data terminal. The system of the present invention is highly adaptable to accommodate medical facilities of varying size. As the system of the present invention is also connected to a variety of computers which include data stores, a wide variety of parameters may be monitored and evaluated so as to avoid conditions of waste, fraud and abuse.

Thus the new system for dispensing and monitoring medical items of the present invention achieves the above stated objectives, eliminates difficulties encountered in the use of prior systems, solves problems and attains the desirable results described herein.

In the foregoing description certain terms have been used for brevity, clarity and understanding. However, no unnecessary limitations are to be implied therefrom because such terms are for descriptive purposes and are intended to be broadly construed. Moreover, the descriptions and illustrations given are by way of examples and the invention is not limited to the exact details shown or described. In addition, any feature of the invention that is described in the following claims as a means for performing a function shall be construed as encompassing any means capable of performing the recited function and shall not be limited to the means disclosed in the foregoing description or any mere equivalent thereof.

Having described the features, discoveries and principles of the invention, the manner in which it is constructed and utilized, and the advantages and useful results obtained, the new and useful structures, devices, elements, arrangements, parts, combinations, systems, equipment, operations, methods and relationships are set forth in the appended claims.

We claim:

1. A method comprising the steps of:
   a) stocking a liner in a stocking location with a first type of medical item;
   b) placing a lid in covering relation relative to the medical item in the liner;
   c) subsequent to step (b) transporting the stocked liner from the stocking location to a dispenser device, wherein the dispenser device has an interior area including a storage location therein, wherein the storage location is configured to accept the liner therein;
   d) subsequent to step (c) separating the lid from the liner;
   e) accessing the interior area of the dispenser device; and
   f) installing the stocked liner in the storage location.

2. The method according to claim 1 and prior to the installing step further comprising the step of removing a previously installed liner from the storage location.

3. The method according to claim 2 and after the removing step further comprising the step of returning the previously installed liner to the stocking location.

4. The method according to claim 3 and after the transporting step further comprising the step of:
   placing the lid in operative connection with the previously installed liner.

5. The method according to claim 1 and after the placing step further comprising the steps of:
   locking the lid in engaged relation with the liner with a lock device; and
   prior to the separating step further comprising the step of unlocking the lid by unlocking the lock device, wherein the lid is enabled to be separated from the liner.

6. The method according to claim 5 wherein the lock device comprises a tamper indicating seal, and wherein the locking step includes installing the tamper indicating seal so as to prevent execution of the separation step without damaging the seal.

7. The method according to claim 1 wherein a first hinge part is in operative connection with the lid and wherein a second hinge part is in operative connection with the liner, and wherein the placing step comprises engaging the first and second hinge parts and rotating the lid relative to the liner.

8. The method according to claim 7 wherein the lid is in operative connection with a first opening and the liner is in operative connection with a second opening, and after the placing step further comprising the step of locking the lid in engaged relation with the liner, wherein the locking step includes extending a locking device through the first and second openings.

9. The method according to claim 8 wherein the first hinge part is at a first end of the lid and the first opening is at a generally opposed end of the lid, and wherein the placing step further comprises rotating the lid to bring the first and second openings into generally linearly aligned relation, wherein the rotating of the lid to bring the first and second openings into the aligned relation relatively moves the first and second hinge parts to prevent separation of the lid from the liner at the second end.

10. The method according to claim 4 and further comprising the step of locking the lid in operatively engaged connection with the previously installed liner with a locking device.

11. The method according to claim 3 and prior to the returning step further comprising the step of transferring a quantity comprising at least one unit of the medical item from the previously installed liner to the stocked liner.

12. The method according to claim 11 and further comprising the steps of:
inputting data representative of the quantity transferred with an input device, and
storing data representative of the quantity transferred in a data store.

13. The method according to claim 3 and prior to the returning step further comprising the steps of:
counting a remaining quantity of units of the medical item remaining in the previously installed liner;
inputting data representative of the remaining quantity with an input device;
storing data representative of the remaining quantity in a data store.

14. The method according to claim 13 and after the returning step, further comprising the steps of:
counting a returned quantity of the medical items in the previously installed liner at the stocking location;
comparing the returned quantity to the remaining quantity stored in the data store.

15. The method according to claim 1 wherein the dispenser device is in operative connection with a data store, and wherein the data store includes data representative of a user authorized to access the interior area of the dispenser device, and wherein the accessing step includes:
inputting with an input device data corresponding to a user;
comparing the input data to the authorized user data stored in the data store;
enabling access to the interior area when the input data corresponds to the data for the authorized user.

16. The method according to claim 1 wherein the dispenser device is in operative connection with a processor and a data store, and prior to the accessing step further comprising the step of:
storing in the data store data representative of the storage location,
and prior to the transporting step further comprising the step of:
applying machine readable indicia corresponding to the storage location in operative connection with the liner,
and wherein the accessing step includes:
reading the machine readable storage location indicia associated with the liner with a reading device in operative connection with the processor;
determining with the processor using the data stored in the data store the storage location corresponding to the read storage location indicia;
operating the dispenser device responsive to the processor to enable access to the storage location.

17. The method according to claim 16 wherein in the storing step the data representative of the storage location includes data representative of the medical item, wherein the type medical item data is stored in the data store in correlated relation with data representative of the storage location in which the type medical item is stored, and wherein in the applying step the indicia includes indicia representative of the type medical item stocked in the liner, and wherein in the accessing step the storage location is determined by the processor from the medical item type indicia read and medical item data and correlated storage location data stored in the data store.

18. The method according to claim 16 and prior to the transporting step further comprising the step of attaching the lid to the liner and holding the lid in engagement with the liner with a seal, and wherein the machine readable indicia is in operative connection with the seal.

19. The method according to claim 16 and prior to the transporting step further comprising the step of labeling the storage location with machine readable indicia representative of the storage location, and after the accessing step further comprising the steps of:
reading the location indicia from the storage location with the reading device,
determining with the processor whether the location indicia read from the accessed storage location corresponds to the location determined by the processor from the location data associated with the liner.

20. A method comprising the steps of:
a) stocking a first liner in a stocking location with a first type of medical item;
b) stocking a second liner with a second type of medical item at the stocking location;
c) releasibly operatively engaging the first liner with the second liner;
d) transporting the first stocked liner from the stocking location to a dispenser device, wherein the dispenser device has an interior area including a storage location therein, wherein the storage location is configured to accept the first liner therein;
e) accessing the interior area of the dispenser device; and
f) installing the first stocked liner in the storage location.

21. The method according to claim 20 wherein the second liner is in operative connection with a first lid, and wherein the first lid and the second liner each include one of either an interengaging projection or recess, and wherein the engaging step comprises engaging the projection and recess of the first lid and second liner.

22. The method according to claim 21 wherein the first lid includes the recess, wherein the recess is bounded by four segments of two wall portions each, each pair of wall portions being disposed generally perpendicular to one another, and wherein the second liner includes the projection on a lower portion thereof, and wherein in the engaging step the projection is extended in nested relation in the recess bounded by the four segments.

23. The method according to claim 21 and wherein the second liner is in operative connection with a second lid, and further comprising a third liner, and wherein the second lid and the third liner each include one of either an interengaging second projection or second recess, and prior to the transporting step further comprising the step of releasibly engaging the second projection and second recess, wherein the first, second and third liners are operatively engaged during the transporting step.

24. The method according to claim 22 wherein the lower portion of the second liner includes at least one aperture therein, and wherein the first lid includes at least one finger projection, and wherein in the engaging step the finger projection is extended in the aperture.

25. The method according to claim 24 wherein the interengaging recess and projection are generally rectangular, and wherein the recess has four corners, and wherein one of each of the four segments is positioned adjacent to one of the corners, and wherein finger projections extend from at least one of the wall portions in each of at least two of the pairs of segments, and wherein the lower portion includes at least two apertures, and wherein in the engaging step each one of the finger projections is extended in one of the apertures.

26. The method according to claim 24 wherein the walls comprising the segments extend generally outward from the lid in a first direction, and wherein the finger projection extends in a direction generally perpendicular to the first direction and parallel to at least one wall in one of the four segments, and wherein in the engaging step the projection extends in nested relation between the aperture and the one wall.

27. The method according to claim 20 wherein in the transporting step the first and second liners are transported to the dispenser device in engaged relation, wherein the dispenser device has a second storage location in the interior area configured to accept the second liner therein, and after the transporting step further comprising the steps of:
operatively disengaging the first and second liners, and
further installing the second liner in the second storage location.

28. The method according to claim 27 and prior to the installing step further comprising the step of removing a previously installed liner from the storage location, and prior to the further installing step removing a second previously installed liner from the second storage location, and further comprising the step of returning the liner and second liner to the stocking location.

29. A medical item stocking system comprising
a liner, wherein the liner is adapted to be stocked with a type of medical item;
a medical item dispenser device wherein the dispenser device has an interior area including a storage location therein, wherein the storage location is configured to accept the liner;
machine readable indicia, wherein the machine readable indicia is in operative connection with the liner, wherein the machine readable indicia includes information corresponding to the medical item type;
a lid, wherein the lid is adapted to close the liner after the medical item is stocked therein;
a tamper indicating seal, wherein the tamper indicating seal is adapted to maintain the lid in engaged relation with the liner, wherein opening the lid is adapted to result in an indication of such an opening.

30. The system according to claim 29
wherein the machine readable indicia includes data corresponding to the storage location, and wherein the machine readable indicia is in operative connection with the seal.

31. A method comprising the steps of:
stocking a liner in a stocking location with a type of medical item;
closing the liner with a lid after the medical item is stocked therein;
applying machine readable indica in operative connection with the liner wherein the indicia corresponds to the medical item type stocked therein;
after the closing step applying a tamper indicating seal to maintain the lid in engaged relation with the liner, wherein opening the lid would result in a residual indication of such opening.

32. The method according to claim 31 and further comprising the steps of:
transporting the liner to a medical item dispenser;
installing the liner in a medical item storage location in the dispenser;
alternatively either before or after the installing step, breaking the tamper indicating seal and removing the lid from closing relation relative to the liner.

33. The method according to claim 32 and further comprising the steps of:
removing at least one medical item from the liner and using the removed medical item in the treatment of a patient.

34. The method according to claim 32 and further comprising the steps of:
removing the liner from the storage location;
returning the liner to the stocking location; and
restocking the liner at the stocking location with a type of medical item.

35. A method comprising the steps of:
reading with a reading device machine readable indicia in operative connection with a liner holding a type of medical item, the machine readable indicia including data corresponding to the medical item type;
determining with a processor in operative connection with the reading device and a data store, a storage location for the liner, the location being determined from the read indicia and data in the data store;
installing the liner in the storage location determined in the determining step.

36. The method according to claim 35 and further comprising a dispenser device in operative connection with the processor, wherein the storage location is in an interior area of the dispenser device, and prior to the installing step, further comprising the step of enabling access to the storage location in the interior area responsive to determining the storage location in the determining step.

37. The method according to claim 35 and prior to the installing step further comprising the step of:
labeling the storage location with machine readable indicia representative of the storage location;
and alternatively either before or after the installing step, reading with the reading device the indicia labeled on the storage location in which the liner is installed; and
comparing with the processor data representative of the location in which the liner is installed and the storage location determined in the determining step.

38. The method according to claim 35 wherein the reading step comprises
reading with a reading device machine readable indicia in operative connection with a liner holding a type of medical item, the machine readable indicia including data corresponding to the medical item type and to a storage location in which the liner is to be installed.

39. A method comprising the steps of:
a) stocking a liner in a stocking location with a first type of medical item;
b) placing a lid in covering relation relative to the medical item in the liner;
c) transporting the stocked liner from the stocking location to a dispenser device, wherein the dispenser device has an interior area including a storage location therein, wherein the storage location is configured to accept the stocked liner therein, and wherein the dispenser device is in operative connection with a data store, wherein the data store includes authorized user data corresponding to at least one authorized user who is authorized to access the interior area of the dispenser device;
d) inputting with an input device data corresponding to a user;

e) comparing the input data to the authorized user data stored in the data store;

f) enabling access to the interior area when the input data corresponds to the authorized user data for an authorized user;

g) separating the lid from the stocked liner;

h) removing a previous installed liner from the storage location; and i) installing the stocked liner in the storage location.

40. A method comprising the steps of:

a) stocking a liner in a stocking location with a first type of medical item;

b) transporting the stocked liner from the stocking location to a dispenser device, wherein the dispenser device has an interior area including a storage location therein, wherein the storage location is configured to accept the liner therein;

c) accessing the interior area of the dispenser device;

d) installing the stocked liner in the storage location; and e) subsequent to step (d), operating the dispenser device, wherein the dispenser device is operated such that access to the medical item in the liner installed in the storage location is limited to authorized users.

41. The method according to claim 40 and further comprising f) removing medical items from the liner when the dispenser is accessed by an authorized user.

42. A method comprising the steps of:

a) stocking a liner in a stocking location with a first type of medical item;

b) transporting the stocked liner from the stocking location to a dispenser device remote from the stocking location, wherein the dispenser device has an interior area including a storage location therein, wherein the storage location is configured to accept the liner therein, and wherein the dispenser device limits access to the storage location to authorized users;

c) accessing the interior area of the dispenser device; and d) installing the stocked liner in the storage location.

43. A method comprising the steps of:

a) stocking a liner in a stocking location with a first type of medical item;

b) transporting the stocked liner from the stocking location to a dispenser device remote from the stocking location, wherein the dispenser device has an interior area including a storage location therein, wherein the storage location is configured to accept the liner therein, wherein the dispenser device is in operative connection with a data store, and wherein the data store includes data representative of a user authorized to access the interior area of the dispenser device;

c) accessing the interior area of the dispenser device, wherein the accessing step includes inputting with an input device data corresponding to a user, comparing the input data to the authorized user data stored in the data store, and enabling access to the interior area when the input data corresponds to the data for the authorized user; and d) installing the stocked liner in the storage location.

44. The method according to claim 43 and further comprising e) removing medical items from the liner when the dispenser is accessed by an authorized user.

45. The method according to claim 43 and subsequent to step (c) performing step (d).

* * * * *